(12) United States Patent
Wender et al.

(10) Patent No.: US 11,746,105 B2
(45) Date of Patent: Sep. 5, 2023

(54) BRYOSTATIN COMPOUNDS AND METHODS OF PREPARING THE SAME

(71) Applicant: The Board of Trustees of the Leland Stanford Junior University, Stanford, CA (US)

(72) Inventors: Paul Wender, Stanford, CA (US); Ryan Quiroz, Boston, MA (US); Stephen Ho, Stanford, CA (US); Akira Shimizu, Stanford, CA (US); Steven Ryckbosch, Albany, CA (US); Matthew C. Stevens, Atherton, CA (US); Matthew S. Jeffreys, King of Prussia, PA (US); Clayton Hardman, Stanford, CA (US); Jack Sloane, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 190 days.

(21) Appl. No.: 17/162,554

(22) Filed: Jan. 29, 2021

(65) Prior Publication Data
US 2021/0292309 A1    Sep. 23, 2021

Related U.S. Application Data

(62) Division of application No. 16/337,221, filed as application No. PCT/US2017/054158 on Sep. 28, 2017, now Pat. No. 10,947,221.

(60) Provisional application No. 62/404,687, filed on Oct. 5, 2016.

(51) Int. Cl.
| | | |
|---|---|---|
| C07D 407/14 | (2006.01) |
| A61K 31/351 | (2006.01) |
| A61P 25/28 | (2006.01) |
| A61P 31/18 | (2006.01) |
| C07D 493/22 | (2006.01) |
| A61P 35/00 | (2006.01) |
| A61K 31/365 | (2006.01) |

(52) U.S. Cl.
CPC .......... *C07D 407/14* (2013.01); *A61K 31/351* (2013.01); *A61K 31/365* (2013.01); *A61P 25/28* (2018.01); *A61P 31/18* (2018.01); *A61P 35/00* (2018.01); *C07D 493/22* (2013.01)

(58) Field of Classification Search
CPC .................................................. C07D 407/14
See application file for complete search history.

(56) References Cited

U.S. PATENT DOCUMENTS

| | | | |
|---|---|---|---|
| 5,750,709 A | 5/1998 | Castor | |
| 7,256,286 B2 | 8/2007 | Wender et al. | |
| 8,497,385 B2 | 7/2013 | Wender | |
| 8,735,609 B2 | 5/2014 | Wender | |
| 8,816,122 B2 | 8/2014 | Wender et al. | |
| 9,096,550 B2 | 8/2015 | Keck et al. | |
| 10,947,221 B2* | 3/2021 | Wender | A61K 31/365 |
| 2003/0233000 A1 | 12/2003 | Lindquist et al. | |
| 2011/0269713 A1 | 11/2011 | Keck et al. | |
| 2015/0087609 A1 | 3/2015 | Spiegel et al. | |
| 2018/0201901 A1 | 7/2018 | Cellectis | |
| 2022/0193029 A1* | 6/2022 | Wender | A61K 31/365 |

FOREIGN PATENT DOCUMENTS

| | | |
|---|---|---|
| CN | 1178793 A | 4/1998 |
| WO | WO 2001/040214 | 6/2001 |
| WO | 2016025363 | 2/2016 |
| WO | WO 2016025363 | 2/2016 |
| WO | WO 2018067382 | 4/2018 |
| WO | WO 2018178378 | 10/2018 |
| WO | WO 2020/014482 | 1/2020 |

OTHER PUBLICATIONS

Dechristopher et al., (2012) "Designed, Synthetically Accessible Bryostatin Analogues Potently Induce Activation of Latent HIV Reservoirs in vitro", Nat Chem. 4(9):705-710.
Loy et al., (2015) "Toward a Biorelevant Structure of Protein Kinase C Bound Modulators: Design, Synthesis, and Evaluation of Labeled Bryostatin Analogs for Analysis with REDOR NMR Spectroscopy", JACS 137:3678-3685.
Ramakrishna et al., (2019) "Modulation of Target Antigen Density Improves CAR T-cell Functionality and Persistence," Clin Cancer Res, 25-17: 5329- 5341.
Yang-Hua et al., "Studies on antineoplastic constituents from marine organisms in south China sea"; Academic Journal of Second Military Medical University. 2002 ;23(3):236-239.
Wender et al. (2002) "The Practical Synthesis of a Novel and Highly Potent Analogue of Bryostain," J. Am. Chem. Soc. 124(46) 13648-13649.
Wender et al. (2011) "Design, synthesis, and evaluation of potent bryostatin analogs that modulate PKC translocation selectivity," PNAS 108(17) 6721-6726.
Wender et al. (2017) "Scalable synthesis of bryostatin 1 and analogs, adjuvant leads against latent HIV" Science 358 218-223.

(Continued)

*Primary Examiner* — Daniel R Carcanague
(74) *Attorney, Agent, or Firm* — Rudy J. Ng; Bozicevic, Field & Francis LLP

(57) ABSTRACT

Methods for preparing a variety of bryostatin compounds are provided. The subject methods provide for preparation of bryostatin 1 in multi-gram quantities in a low and unprecedented number of convergent synthetic steps from commercially available materials. The subject methods are scalable with low estimated material costs and can provide enough material to meet clinical needs. Also provided are a variety of bryostatin analog compounds, and prodrug forms thereof, which are synthetically accessible via the subject methods and pharmaceutical compositions including the same.

3 Claims, 16 Drawing Sheets

(56) References Cited

OTHER PUBLICATIONS

Keck et al., (2011) "Total Synthesis of Bryostatin 1", J. Am. Chem. Soc, 133(4): 744-747.
Hardman et al., (2020) "Synthesis and Evaluation of Designed PKC Modulators for Enhanced Cancer Immunotherapy", Nature Communications, vol. 11(1879): 11 pages.
Ramakrishna et al., (2017), "Modulation of CD22 Antigen Density Improves Efficacy of CD22 Chimeric Antigen Receptor (CAR) T Cells Against $CD22^{10}$ B-Lineage Leukemia and Lymphoma", Blood, vol. 130(3894): 3 pages.
Shimizu (2019) "Supply Impacting Synthesis of Bryostatin 1 and The Design, Synthesis, and Evaluation of Bryostatin 1 Analogs", A Dissertation Submitted to the Department of Chemistry and The Committee on Graduate Studies of Stanford University In Partial Fulfillment of the Requirement for the Degree of Doctor of Philosophy, 348 pages.

\* cited by examiner

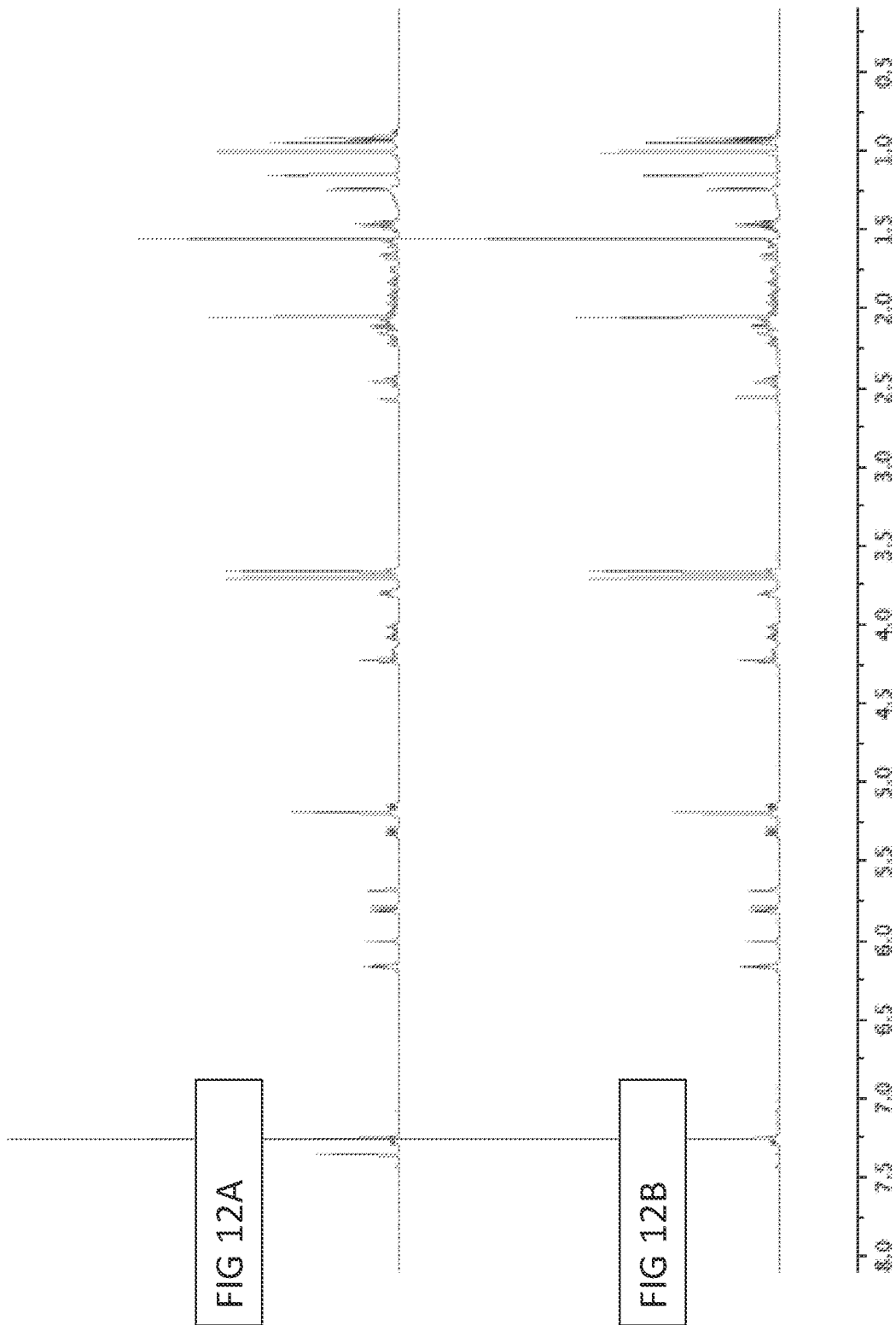

BRYOSTATIN COMPOUNDS AND METHODS OF PREPARING THE SAME

CROSS-REFERENCE

This application is a divisional of U.S. application Ser. No. 16/337,221, filed Mar. 27, 2019, now U.S. Pat. No. 10,947,221, which is a U.S. national stage entry of International Application No. PCT/US2017/054158, filed Sep. 28, 2017, which claims the benefit of U.S. Provisional Patent Application No. 62/404,687, filed Oct. 5, 2016, which applications are incorporated herein by reference in their entirety.

STATEMENT REGARDING FEDERALLY SPONSORED RESEARCH

This invention was made with Government support under contracts CA031841 and CA031845 awarded by the National Institutes of Health. The Government has certain rights in the invention.

INTRODUCTION

Bryostatin 1 is a marine natural product that is a potent protein kinase C (PKC) modulator currently in clinical trials for cancer, HIV/AIDS, and Alzheimer's disease. For HIV, there are 38 million people globally infected and 1.2 million deaths annually. There are 5.4 million patients with Alzheimer's disease in America alone where it is the third leading cause of death.

Bryostatin can be isolated (e.g., in 0.00014% yield) from the marine organism *Bugula neritina*, produced in minor amounts through biosynthesis, or prepared in minor amounts by total chemical synthesis. To date, chemical syntheses of various natural bryostatin compounds have required about 37-90 synthetic steps. The only published synthesis of clinical candidate bryostatin 1 requires 57 steps and proceeds in low overall yield (e.g., 1.1% overall) (Keck et al., *J. Am. Chem. Soc.*, 2011, 133 (4), pp 744-747).

SUMMARY

Methods for preparing a variety of bryostatin compounds are provided. The subject methods provide for preparation of bryostatin 1 in multi-gram quantities in a low and unprecedented number of convergent synthetic steps from commercially available materials. The subject methods are scalable with low estimated material costs and can provide enough material to meet clinical needs. Also provided are a variety of bryostatin analog compounds, and prodrug forms thereof, which are synthetically accessible via the subject methods and pharmaceutical compositions including the same.

BRIEF DESCRIPTION OF THE FIGURES

The invention is best understood from the following detailed description when read in conjunction with the accompanying drawings. The patent or application file contains at least one drawing executed in color. It is emphasized that, according to common practice, the various features of the drawings are not to-scale. On the contrary, the dimensions of the various features are arbitrarily expanded or reduced for clarity. Included in the drawings are the following figures. It is understood that the drawings, described below, are for illustration purposes only. The drawings are not intended to limit the scope of the present teachings in any way.

FIG. 12A shows an $^1$H NMR trace for a natural sample of bryostatin 1 (3 mg in 1 mL CDCl$_3$); and FIG. 12B shows an $^1$H NMR trace for synthetic bryostatin 1, prepared by the subject methods (3 mg in 1 mL CDCl$_3$).

DEFINITIONS

Figure 1:
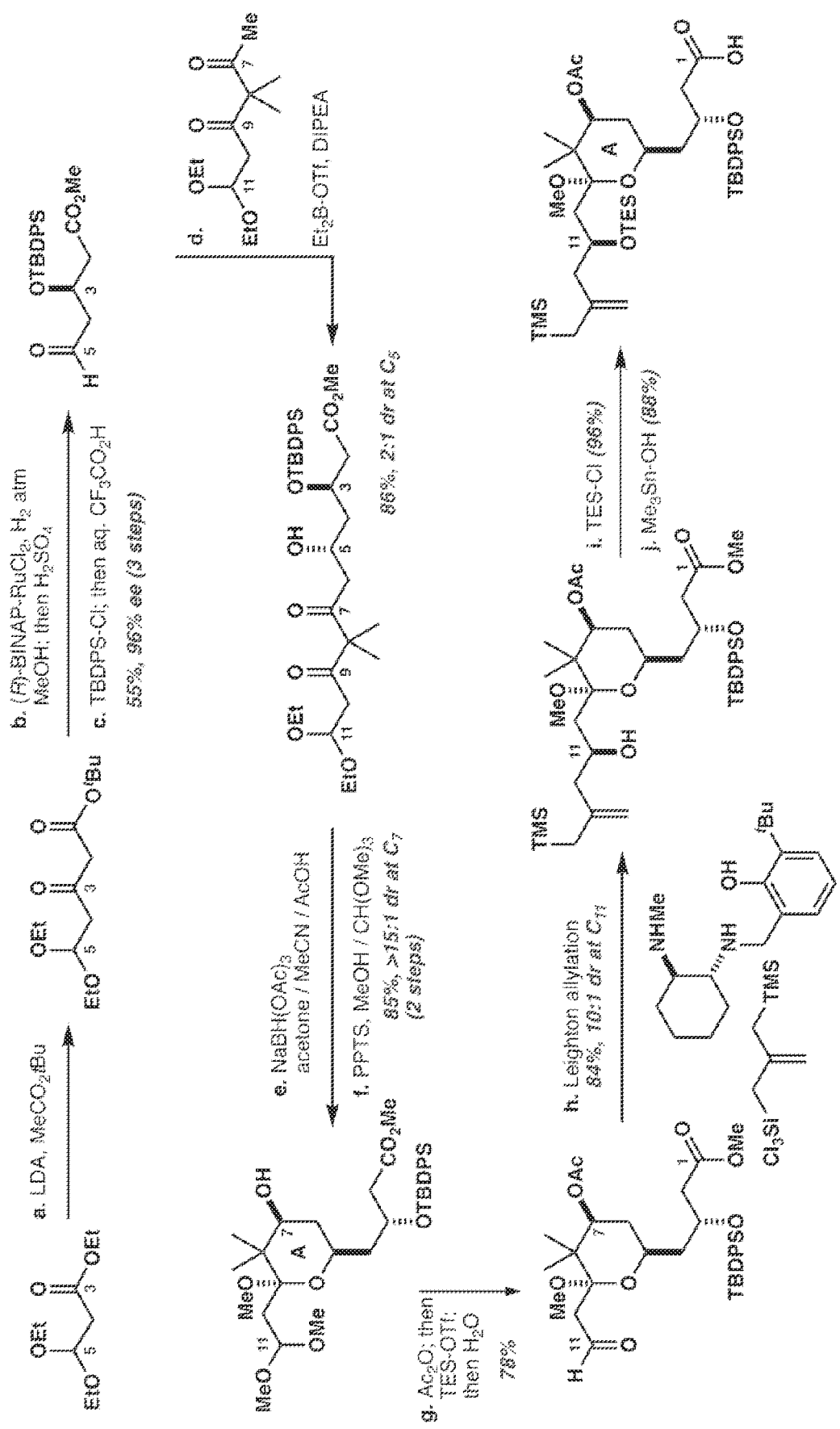
FIG. 1 depicts an exemplary reaction scheme for the preparation of the Northern Hemisphere fragment of bryostatin compounds.

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

Numeric ranges are inclusive of the numbers defining the range.

The methods described herein include multiple steps. Each step may be performed after a predetermined amount of time has elapsed between steps, as desired. As such, the time between performing each step may be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step may be performed after an incubation or waiting time after completion of the previous step, e.g., a few minutes to an overnight waiting time. In certain cases, a step may be performed using materials (e.g., intermediate materials that have been previously prepared using any convenient methods) that have been stored for any convenient period of time.

"Alkyl" refers to monovalent saturated aliphatic hydrocarbyl groups having from 1 to 20 carbon atoms and such as 1 to 10 carbon atoms, or 1 to 6, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups having from 1 to 20 and in some cases, 1 to 10, or 1 to 6, or 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—$C(CH_3)_2CH_2C(O)$—), (—$C(CH_3)_2CH_2C(O)NH$—), (—$CH(CH_3)CH_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"—where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 20 carbon atoms and in some cases 2 to 10 carbon atoms, such as 2 to 7 carbon atoms, and having at least 1 and in some cases from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Allenyl" refers to straight chain or branched hydrocarbyl groups having from 2 to 20 carbon atoms and in some cases 2 to 10 carbon atoms, such as 2 to 7 carbon atoms and having a carbon atom having double bond unsaturation to each of its two adjacent carbon atoms. Included within this term are the stereo isomers or mixtures of these isomers.

The term "substituted allenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 20 carbon atoms and in some cases 2 to 10 carbon atoms, such as 2 to 7 carbon atoms, and having at least 1 and in some cases from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O)NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —$NH_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —$N_3$.

"Carboxyl," "carboxy" or "carboxylate" refers to —$CO_2H$ or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

"Cycloalkenyl" refers to non-aromatic cyclic alkyl groups of from 3 to 10 carbon atoms having single or multiple rings and having at least one double bond and in some cases from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, A-pyrrolidinyl, A-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}$ $(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})$ $NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)$ $R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C$ $(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2$ $O^-M^+$, —$S(O)_2OR^{70}$, —$OS(O)_2R^{70}$, —$OS(O)_2O^-M^+$, —$OS(O)_2OR^{70}$, —$P(O)(O)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})$ $R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)$ $OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)$ $NR^{80}R^{80}$, —$NR^{70}C(NR^{70})R^{70}$ and —$NR^{70}C(NR^{70})$ $NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "synthetic equivalent" or "reactive equivalent" is well understood by those skilled in the art, especially in the art of retrosynthesis, as a reference to a compound (or compounds) corresponding with a given "synthon" (E. J. Corey, Pure App. Chem., 1967, 14: 30-37). Any given synthon may have a plurality of synthetic equivalents. The term "synthon" refers to a compound that includes a core constituent part of a target molecule to be synthesized that is regarded as the basis of a synthetic procedure. For example, a synthon can refer to a fragment identified by retrosynthetic analysis or a synthetic building block related to a possible synthetic procedure. The term "synthetic equivalent" refers to a compound that can be utilized as an alternative to a target intermediate or starting material in a synthetic strategy without need for substantively changing the strategy and procedure. It is understood that a synthetic equivalent can be related to the target intermediate or starting material by including the same arrangement of functional groups or precursors thereof, or protected versions thereof, on a fragment of the underlying target scaffold of interest. Synthetic equivalents can refer to different functional groups having similar chemistry. A synthon can refer to a fragment resulting from retrosynthetic analysis e.g. disconnections of carbon-carbon bonds of the target molecule. A synthetic equivalent can refer to the actual substrates used in the synthetic procedure towards the target molecule. In some cases, the terms synthon and synthetic equivalent refer to the same molecule. In some cases, the term synthon refers to a synthetic fragment that allows for a plurality of synthetic equivalents. The definition of synthetic equivalent includes compounds, where a moiety of a compound of interest that would be labile or reactive under the conditions to be used in a said chemical reaction is protected or masked by an appropriate protecting group that can be cleaved off after said chemical reaction. In some cases, the definition includes compounds where a moiety of a compound of interest is protected or masked with a protecting group that is designed to be cleaved off during a said chemical reaction to provide a labile or reactive group in situ.

"Promoiety" refers to a form of protecting group that, when used to mask a functional group within an active agent, converts the active agent into a prodrug.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate (e.g., 3-hexyne-1,6-dioate), benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, (3-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

Other definitions of terms may appear throughout the specification.

DETAILED DESCRIPTION

As summarized above, methods for preparing a variety of bryostatin compounds are provided. The subject methods provide for preparation of bryostatin 1 in multi-gram quantities in a low and unprecedented number of convergent synthetic steps from commercially available materials. The subject methods are scalable with low estimated material costs and can provide enough material to meet clinical needs. Also provided are a variety of bryostatin analog compounds and prodrug forms thereof which are synthetically accessible via the subject methods and pharmaceutical compositions including the same.

Before the various embodiments are described in greater detail, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

In further describing the subject invention, synthetic methods for preparing a variety of bryostatin compounds are described first in greater detail. Next, bryostatin analog compounds of interest are described. Then, methods of interest in which the bryostatin compounds find use are reviewed. Pharmaceutical compositions that find use in the subject methods are also described.

Methods of Preparation

As summarized above, the present disclosure provides methods for preparing a variety of bryostatin compounds, including lead therapeutic compound bryostatin 1. The current supply of bryostatin 1 is nearly or completely exhausted and its future supply based on conventional approaches is uncertain. The subject methods provide a scalable synthesis of bryostatin 1 and a variety of bryostatin analog compounds. The synthetic approach used in the subject methods provides the first gram and multi-gram total chemical synthesis of bryostatin 1, and synthetic access to a variety of analog compounds that exhibit unique and therapeutically significant properties and functions. One exemplary synthetic route to bryostatin 1 provided by the subject methods includes 33 total steps or fewer, roughly half of the 57 steps required in the conventional synthesis. One exemplary convergent synthesis to bryostatin 1 provided by the subject methods includes 29 steps, with a longest linear sequence of 19 steps and 4.8% overall yield (>80% average yield per step). The synthetic routes provided by the subject methods involve conceptually novel retrosynthetic bond disconnections, and combinations of particular reaction intermediates, particular synthetic methods, particular protecting group chemistries and strategies, and/or particular purification strategies, examples of which are described in length herein. The particular nature and unique sequence of steps with which these bond disconnections are addressed in the subject methods provides for a dramatic reduction in synthetic steps over conventional methods.

As used herein, the term "bryostatin compound" refers to compounds having an underlying bryostatin pharmacophore, which is based on the bryostatin natural products and in some cases has a scaffold that is characterized by a macrocyclic lactone-containing ring including three embedded six-membered rings (e.g., tetrahydropyran rings designated A, B and C rings), and an arrangement of numbered C1 to C26 carbon atoms, as exemplified in the bryostatin 1 structure shown below. The lactone of the scaffold is defined by a bond between a C1 carbonyl and the oxygen of a C25 hydroxyl group.

Bryostatin 1

The bryostatin scaffold can include an alkene between C16 and C17 and an exocyclic alkene at positions C13 and C21. The bryostatin scaffold can include a particular arrangement of stereocenters, e.g. at C3, C5, C7, C9, C11, C15, C19, C20 and C23, C25 and/or C26. A variety of substituent groups and derivative groups (e.g., esters or ether groups) can be included in the subject bryostatin compounds (e.g., as described herein). Naturally occurring bryostatins originally isolated from the marine bryozoan include a family of about 21 known compounds. The term "bryostatin compound" is meant to include both the naturally occurring bryostatin compounds, such as bryostatin 1, and as well as "bryostatin analog compounds", which include non-naturally occurring bryostatin analogs and derivative compounds of interest that retain functionality required for biological activity.

Figure 10:
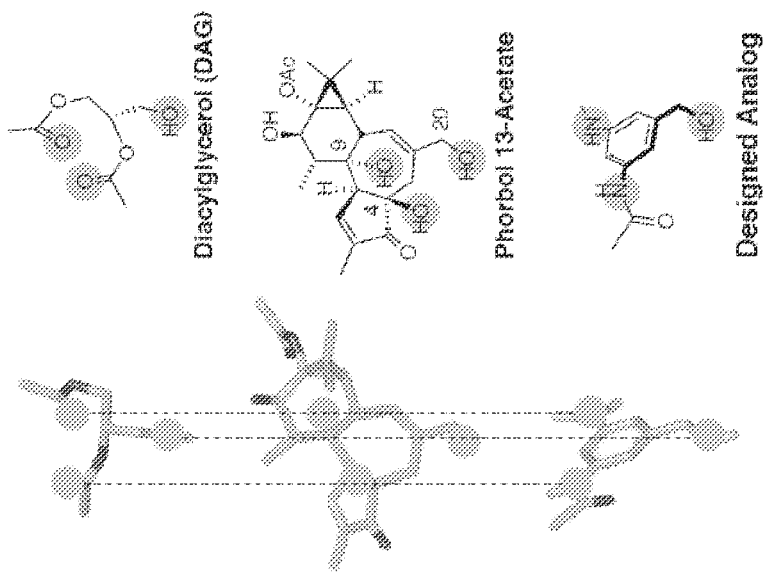
FIG. 10 shows an alignment of three structures having a spatial arrangement of hydrogen bond donors and acceptors, which illustrates the bryostatin pharmacophore.

The term "bryostatin compound" is meant to include a compound having the same underlying bryostatin pharmacophore, namely a three dimensional spatial arrangement of three hydrogen bond donors and acceptors that provides its binding function along with a lipid domain that provides for its association with a membrane and for its function derived thereof. This bryostatin pharmacophore or PKC pharmacophore model was introduced by the Wender group in 1986 (see e.g., Wender, PNAS, 1986, 83, 4214-4218), and extended to Bryostatin in 1988 (see e.g., Wender, PNAS, 1988, 85, 7197-7201), leading to the design of the first Bryostatin analogs (e.g., Wender, JACS, 1998, 120, 4534-4535; and Wender, PNAS, 1998, 95, 6624-6629 the disclosures of which are herein incorporated by reference in their entirety). The pharmacophore model is described in U.S. Pat. No. 8,735,609, the disclosure of which is herein incorporated by reference in its entirety. The bryostatin compounds can be broadly described as having two main regions that are referred to herein as a "recognition domain" (or pharmacophoric region) and a relatively lipophilic "spacer domain" (or linker region). The recognition domain contains structural features that are analogous to those spanning C17 through C26 to C1, including the C ring formed in part by atoms C19 through C23, and the lactone linkage between C1 and C25 of the native bryostatin macrocycle. The spacer domain, on the other hand, joins the atoms corresponding to C1 through C17 of the native bryostatin macrocycle to substantially maintain the relative distance between the C1 and C17 atoms and the directionality of the C1C2 and C16C17 bonds. In addition to its function of maintaining the recognition domain in an active conformation, the spacer domain provides a moiety that can be readily derivatized according to any convenient synthetic techniques to provide analogues having improved in vivo stability and pharmacological properties (e.g., by modulating side effect profiles) while retaining biological activity. The linker region of the bryostatin family can be varied significantly to provide analogs that retain bryostatin-like pan-PKC isoform binding selectivities and affinities and other analogs that exhibit selectivities and affinities for only one or more PKC isoforms. Thus, a wide variety of linkers can be used to retain the PKC-binding activities of bryostatin 1 or to produce complementary PKC selectivities. Such selectivities influence translocation of PKC and its therapeutic activity as well as off target effects. In some cases, the bryostatin compounds include a linker moiety L, which is a linear, cyclic, or polycyclic linker moiety containing a continuous chain of from 6 to 14 chain atoms, one embodiment of which defines the shortest path from C25 via C1 to C17. Distance "d" should be about 2.5 to 5.0 angstroms, preferably about 3.5 to 4.5 angstroms and most preferably about 4.0 angstroms, such as about 3.92 angstroms (as experimentally determined, for example, by NMR spectroscopy). Thus, L may consist solely of a linear chain of atoms that links C17 via C1 to C25, or alternatively, may contain one or more ring structures which help link C17 via C1 to C25. In certain instances, the linker region includes a lactone group (—C(=O)O—), or a lactam group (—C(=O)NH—), which is linked to C25 of the recognition region, by analogy to the C1 lactone moiety that is present in the naturally occurring bryostatins. In addition, the linker can include a hydroxyl group analogous to the C3 hydroxyl found in naturally occurring bryostatins, to permit formation of an intramolecular hydrogen bond between the C3 hydroxyl of the linker and the C19 hydroxyl group of the recognition region (and optionally with the oxygen of the native B ring). In some embodiments, the linker terminates with —CH(OH)CH$_2$C(=O)O—, for joining to C25 of the recognition region via an ester (or when cyclized, a lactone) linkage. Exemplary structures illustrating the bryostatin pharmacophore are shown in FIG. 10 and below where the linker domain is illustrated:

It is understood that for any of the bryostatin compounds described herein, and their synthetic precursors, a numbering scheme can be used to refer to the atoms which correspond to those of the macrocyclic ring and attached substituents as described above for the underlying bryostatin scaffold. Bryostatin compounds of interest include, but are not limited to, any one of the naturally occurring bryostatins, e.g., bryostatin 1, bryostatin 2 and bryostatin 3, and bryostatin analogs, such as those described in U.S. Pat. Nos. 8,735,609, 7,256,286, 8,816,122 and 9,096,550, the disclosures of which are incorporated by reference herein.

In general terms, the subject methods provide several significant methodological innovations including, but not limited to:

(a) first-in-kind asymmetric allylation reactions for setting the C11 stereocenter of the bryostatin scaffold in a way that is compatible with existing functionality;

(b) a general, one-step method for synthesizing chiral pyranyl motifs from 1,5-ketoaldehydes; and (c) first-in-kind protecting groups for masking sensitive functionalities, including but not limited to, the C20 dienoate ester of bryostatin 1 in a way that is compatible with existing functionality.

Any convenient bryostatin compounds, and precursors or derivatives thereof, can be targeted for synthesis using the subject methods of preparation. In some embodiments, the method is a method of making a bryostatin compound of Formula (XXIV):

(XXIV)

wherein:

W$^1$ is an alkenyl, a substituted alkenyl, an alkynyl, a substituted alkynyl, an allenyl, a substituted allenyl, an aryl, a substituted aryl, a heteroaryl, a substituted heteroaryl, an alkyl, a substituted alkyl, or a carbon chain containing oxygen or nitrogen atoms, and/or rings and substituted rings included cycloalkyl, cycloalkenyl and the like (e.g., a PEG or modified PEG group);

Z$^2$ is =O, =CR$^5$R$^6$ or =NR$^7$ when the covalent bond designated "b" is a double bond;

Z$^2$ is —OR$^8$ or —N(R$^7$)$_2$ when the covalent bond designated "b" is a single bond;

X$^1$ is H or OR$^{11}$;

Y$^1$ is H or OR$^{12}$;

R$^5$, R$^6$, R$^7$ and R$^8$ are each independently H, halogen (e.g., F), alkyloxycarbonyl (e.g., —CO$_2$Me), substituted alkyloxycarbonyl, alkyl or substituted alkyl;

R$^{11}$ is H, an acyl, a substituted acyl, an alkyl, a substituted alkyl, or CO-aryl, or CO-heteroaryl and substituted versions thereof;

R$^{12}$ is H, an alkyl or a substituted alkyl;

R$^{13}$ is H, an alkyl or a substituted alkyl;

R$^{14}$ and R$^{15}$ are independently H, a hydroxyl protecting group or a promoiety; and R$^{16}$ is H, an alkyl, a substituted alkyl, or CO-aryl, or CO-heteroaryl and substituted versions thereof.

In certain embodiments of formula (XXIV), the covalent bond designated "b" is a double bond and Z$^2$ is CR$^5$R$^6$ (e.g., $CHCO_2Me$) or $NR^7$. In certain instances, $Z^2$ is $CR^5R^6$. In certain cases, $Z^2$ is $CHCO_2R'$ where R' is alkyl (e.g., methyl). In certain instances, $Z^2$ is $CR^5R^6$. In certain cases, $Z^2$ is $CFCO_2R'$ where R' is alkyl (e.g., methyl). In certain instances, $Z^2$ is $NR^7$. In certain instances, $Z^2$ is NH. In certain instances, $Z^2$ is N-alkyl. In certain cases, C13 is connected to two groups representing $Z^2$, such as two —OR groups where R=alkyl, aryl, heteroalkyl, or heteroaryl, substituted or unsubstituted.

In certain embodiments of formula (XXIV), the covalent bond designated "b" is a single bond and $Z^2$ is $OR^8$ or $N(R^7)_2$. In certain instances, $Z^2$ is $OR^8$. In certain cases, $Z^2$ is OH. In certain cases, $Z^2$ is O-acyl or O-(substituted acyl). In certain instances, $Z^2$ is $N(R^7)_2$. In certain cases, $Z^2$ is $NH_2$. In certain cases, $Z^2$ is $N(alkyl)_2$.

In certain embodiments of formula (XXIV), $X^1$ is $OR^{11}$. In certain embodiments of formula (XXIV), $X^1$ is $OR^{11}$, where $R^{11}$ is acyl or substituted acyl. In some cases, $R^{11}$ is acetyl. In certain embodiments of formula (XXIV), $X^1$ is H. In certain embodiments of formula (XXIV), $Y^1$ is $OR^{12}$. In certain embodiments of formula (XXIV), $Y^1$ is $OR^{12}$, where $R^{12}$ is alkyl or substituted alkyl. In certain instances, $R^{12}$ is methyl. In certain embodiments of formula (XXIV), $Y^1$ is H. In certain embodiments of formula (XXIV), $R^{16}$ is alkyl or substituted alkyl. In certain embodiments of formula (XXIV), $R^{16}$ is methyl.

In certain embodiments of formula (XXIV), $W^1$ is an alkenyl, a substituted alkenyl, an alkynyl, a substituted alkynyl, an alkyl or a substituted alkyl. In certain embodiments of formula (XXIV), $W^1$ is a carbon chain containing oxygen or nitrogen atoms, and/or rings and substituted rings included cycloalkyl, cycloalkenyl and the like (e.g., a PEG or modified PEG group) In certain embodiments of formula (XXIV), $W^1$ is alkenyl or a substituted alkenyl. In certain embodiments of formula (XXIV), $W^1$ is —CH═CHCH═CHR$^4$, wherein $R^4$ is alkyl or substituted alkyl. In certain instances, $W^1$ is —CH═CHCH═CH—$C_3H_7$.

The bryostatin compounds can be prepared via a synthetic strategy involving parallel synthesis of a Northern Hemisphere fragment (see e.g., FIG. 1) and a Southern Hemisphere fragment (see e.g., FIG. 2), followed by a fragment coupling (see e.g., FIG. 3) step, and in some cases an ozonolysis step.

Figure 2:
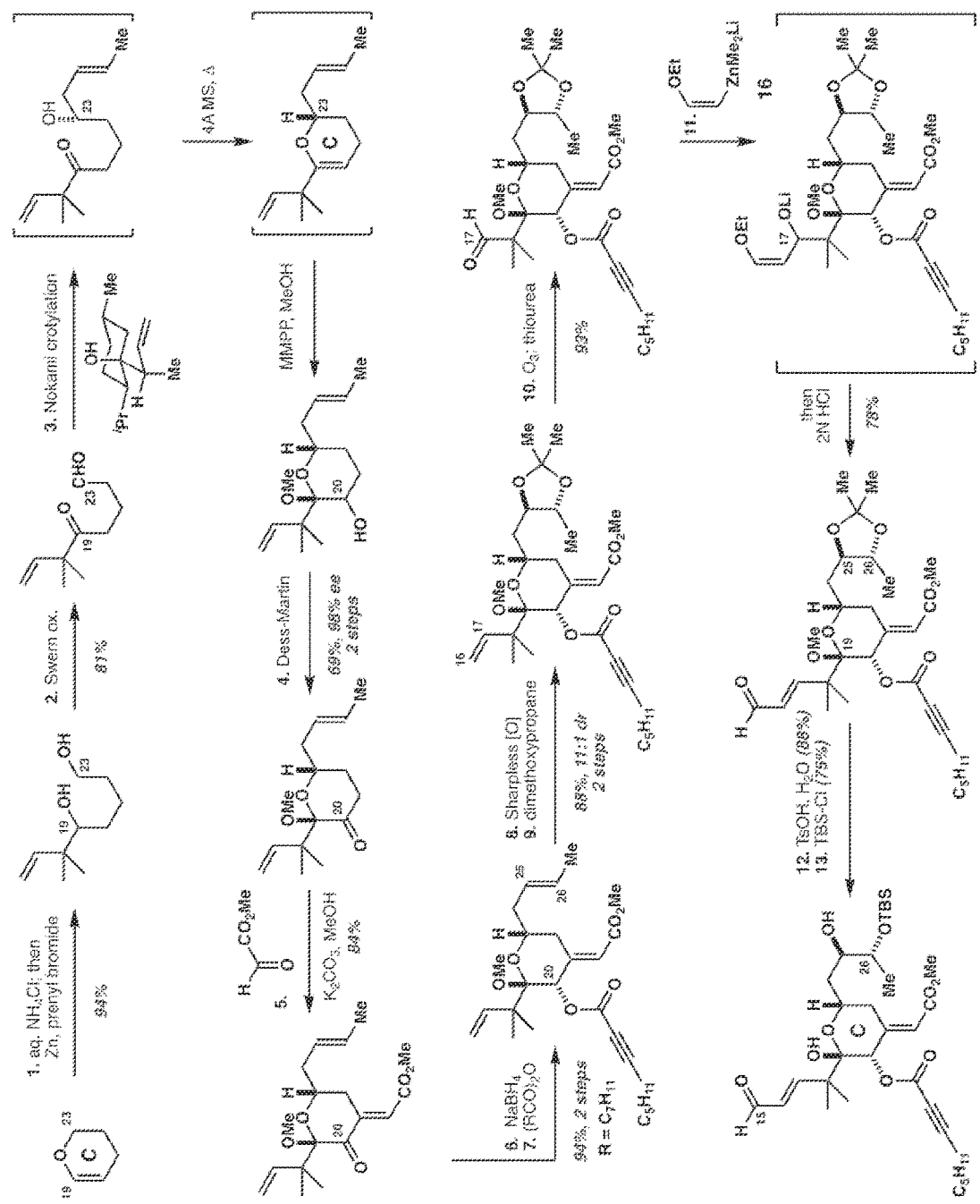
FIG. 2 depicts an exemplary reaction scheme for the preparation of the Southern Hemisphere fragment of bryostatin compounds.

It is understood that the fragment synthesis methods described herein can also be performed by entering the syntheses at any convenient point in the depicted sequence of steps, e.g., at Step 2, Step 3, Step 4, Step 5, Step 6, Step 7, Step 8, Step 9, Step 10, Step 11, Step 12 or Step 13 (e.g., of FIG. 1 or FIG. 2) and progressing to the end of the sequence, thereby bypassing one or more of the earlier steps described. In such cases, any convenient alternative conventional methods can be utilized in preparing as an alternative starting material, one of the intermediate compounds, e.g., one of the intermediate compounds (or an analog thereof) as depicted in FIG. 1 or FIG. 2. The subject methods are meant to encompass any sequences and combinations of the subject synthetic steps that lead to the Northern and Southern fragments of the subject Bryostatin compounds.

In some cases, the Southern fragment can be prepared according to the subject methods of FIG. 2 beginning at step 2. In some cases, the southern fragment can be prepared according to the subject methods beginning at step 3. In some cases, the southern fragment can be prepared according to the subject methods beginning at step 4. In some cases, the southern fragment can be prepared according to the subject methods beginning at step 5. In some cases, the southern fragment can be prepared according to the subject methods beginning at step 6. In some cases, the southern fragment can be prepared according to the subject methods beginning at step 7. In some cases, the southern fragment can be prepared according to the subject methods beginning at step 8. In some cases, the southern fragment can be prepared according to the subject methods beginning at step 9. In some cases, the southern fragment can be prepared according to the subject methods beginning at step 10. In some cases, the southern fragment can be prepared according to the subject methods beginning at step 11. In some cases, the southern fragment can be prepared according to the subject methods beginning at step 12/13.

In some cases, the Northern fragment can be prepared according to the subject methods as depicted in FIG. 1 beginning at step 2. In some cases, the Northern fragment can be prepared according to the subject methods beginning at step 3. In some cases, the Northern fragment can be prepared according to the subject methods beginning at step 4. In some cases, the Northern fragment can be prepared according to the subject methods beginning at step 5. In some cases, the Northern fragment can be prepared according to the subject methods beginning at step 6. In some cases, the Northern fragment can be prepared according to the subject methods beginning at step 7. In some cases, the Northern fragment can be prepared according to the subject methods beginning at step 8. In some cases, the Northern fragment can be prepared according to the subject methods beginning at step 9. In some cases, the Northern fragment can be prepared according to the subject methods beginning at step 10.

A variety of compounds can be utilized as a starting material in the preparation of the Northern Hemisphere fragment according to the subject methods. It is understood that the methods and procedures described herein can be adapted to utilize any convenient compound as a starting materials. The subject methods are meant to include methods of preparing the Northern and/or Southern fragments where one or more (e.g., 1, 2, 3, 4, 5, 6, 7, 8, 9, 10 or more) of the individual steps described herein (e.g., one or more of the steps represented in FIGS. 1 and 2) are adapted and combined to produce the fragments. In some cases, while the strategy allows for variation in protecting groups, the subject method provides an integration of protecting steps and functionalities such that, for example, a change in the acylation of C20 in step 7 of the southern fragment synthesis would preclude the isomerization used in the final stages of the synthesis; in other words, the selection of the C20 group in the early part of the synthesis influences the reactions at the end of the synthesis and all steps in between. As such, also included are methods of preparing the Northern and Southern fragments where any one of the intermediate compounds described herein can be utilized as a starting material, and which can be prepared via any convenient alternative methods. In some cases, the Northern Hemisphere fragment is prepared from commercially available starting materials, such as ethyl 3,3-diethoxypropionate and t-butyl acetate. In some cases, the total synthetic step count to complete the northern fragment is 15 steps or fewer from these reagents, such as 14 steps or fewer, 13 steps or fewer, 12 steps or fewer, 11 steps or fewer, 10 steps or fewer, 9 steps or fewer, or even fewer. In some cases, the total synthetic step count to complete the northern fragment is 10 steps or fewer from these reagents, such as 10 steps, 9 steps, etc.

In some embodiments, the method comprises preparing a compound of formula (Xa) from a starting material of formula (I), or a synthetic equivalent or synthon thereof:

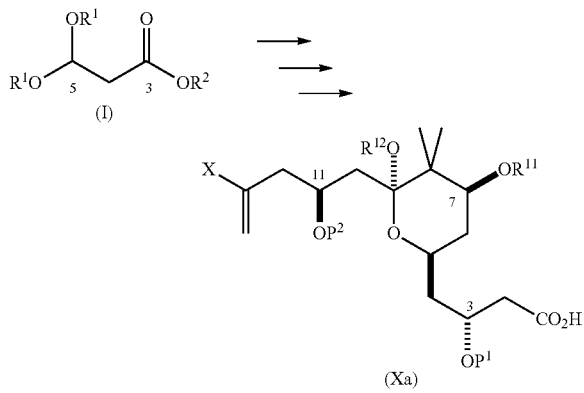

wherein:

$P^1$ and $P^2$ are independently H or a hydroxyl protecting group;

X is H, alkyl, substituted alkyl (e.g., —$CH_2SiR_3$), alkoxy, substituted alkoxy, amino, substituted amino (e.g., —$NR_2$ where R is alkyl, substituted alkyl, or H) or halogen (e.g., F, Br, Cl or I);

$R^1$-$R^3$ is independently H, an alkyl or a substituted alkyl;

$R^{12}$ is an alkyl or a substituted alkyl; and $R^{11}$ is an acyl, a substituted acyl, an alkyl or a substituted alkyl. In some cases, the compound of formula (Xa) is of formula (X).

In some embodiments, the method comprises preparing a compound of formula (X) from a starting material of formula (I):

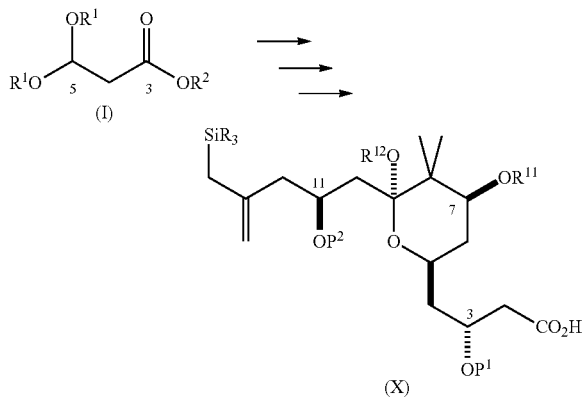

wherein:

$P^1$ and $P^2$ are independently H or a hydroxyl protecting group;

each R and $R^1$-$R^3$ is independently H, an alkyl or a substituted alkyl;

$R^{12}$ is an alkyl or a substituted alkyl; and $R^{11}$ is an acyl, a substituted acyl, an alkyl or a substituted alkyl.

In certain embodiments of formula (I), each $R^1$ and $R^2$ is an alkyl. In certain instances of formula (I), each $R^1$ and $R^2$ is ethyl. In certain embodiments of formula (X), $R^{11}$ is an acyl or a substituted acyl. In certain cases of formula (X), $R^{11}$ is acetyl. In certain cases of formula (X), each R is alkyl. In certain cases of formula (X), each R is methyl. In certain cases of formula (X), $P^1$ and $P^2$ are each independently a silyl ether protecting group. In certain cases, $P^1$ is t-butyldiphenylsilyl (TBDPS). In certain cases, $P^2$ is triethylsilyl (TES).

Any convenient number of steps can be performed in order to prepare a compound of formula (X) from a starting material of formula (I). In some instances, 20 synthetic steps or are utilized, such as 15 synthetic steps or less, 14 synthetic steps or less, 13 synthetic steps or less, 12 synthetic steps or less, 11 synthetic steps or less, 10 synthetic steps or less, or even less. As used here, a "synthetic step" refers to a one-pot synthetic procedure from a starting material(s) to produce a product which is isolated at the end of the procedure (e.g., after a workup procedure to remove reagents and impurities) and optionally purified (e.g., via chromatography) and characterized. In certain instances, a single synthetic step can include preparation of an intermediate in situ which is not itself isolated. It is understood that in the synthetic schemes described herein that the arrow indicating starting materials and products can refer to a single synthetic step or multiple synthetic steps.

In some instances, a compound of formula (X) can be referred to as a Northern Hemisphere fragment of a target bryostatin compound. FIG. 1 illustrates one possible sequence of steps (e.g., steps 1 to 10) that can be used. In certain instances, the method includes preparing a compound of formula (X) from a starting material of formula (I) via ten synthetic steps of the type exemplified in FIG. 1. It is understood that based on the present disclosure, variations of the synthetic strategy, the protecting groups, the reagents and reaction conditions depicted in the figures are possible.

In some embodiments, the method of preparing the Northern Hemisphere fragment includes preparing a compound of formula (II) from a compound of formula (I), e.g., via a Claisen condensation with $MeCO_2R^4$:

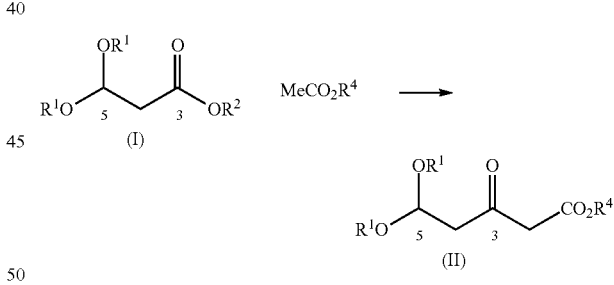

where each $R^1$ and $R^4$ is independently an alkyl or a substituted alkyl; and $R^2$ is H, an alkyl or a substituted alkyl. In some cases, the method step includes a crossed-Claisen condensation reaction of (I) with $MeCO_2R^4$ in the presence of a base. In some cases, this structure is accessed in a single step, as opposed to 2-3 steps used for conventional procedures. In some cases, each $R^1$ is an alkyl or a substituted alkyl, such as ethyl. In some cases, $R^2$ is an alkyl or a substituted alkyl, such as ethyl. In some cases, $R^4$ is an alkyl or a substituted alkyl, such as tert-butyl. In certain instances, both $R^1$ and $R^4$ are selected to provide for suppression of enolate exchange. In general terms, relatively sterically large $R^1$ and $R^4$ groups are used, e.g., ethyl, propyl, isopropyl, or tert-butyl. In certain instances of the method, during workup, an acid wash of the crude product is performed to remove contaminating basic impurities.

In some embodiments, the method of preparing the Northern Hemisphere fragment includes preparing a compound of formula (III) from a compound of formula (II):

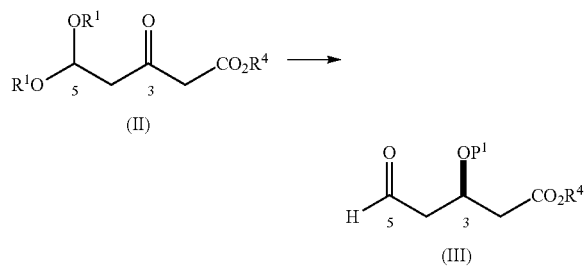

where each $R^1$ and $R^4$ is independently H, an alkyl or a substituted alkyl and $P^1$ is a hydroxyl protecting group. In some cases, the method includes a first step of stereoselective Noyori reduction of the C3 ketone using low catalyst loadings and a second step including C3 hydroxyl protection followed by acidic hydrolysis of the C5 acetal. In certain cases of formula (III), $P^1$ is a silyl ether protecting group. In certain cases, $P^1$ is t-butyldiphenylsilyl (TBDPS). In some cases, each $R^1$ is an alkyl or a substituted alkyl, such as ethyl. In some cases, $R^4$ is an alkyl or a substituted alkyl, such as methyl or tert-butyl. The aldehyde (III) can be prepared via any convenient alternative methods.

In some embodiments, the method comprises preparing a compound of formula (X) from a compound of formula (III):

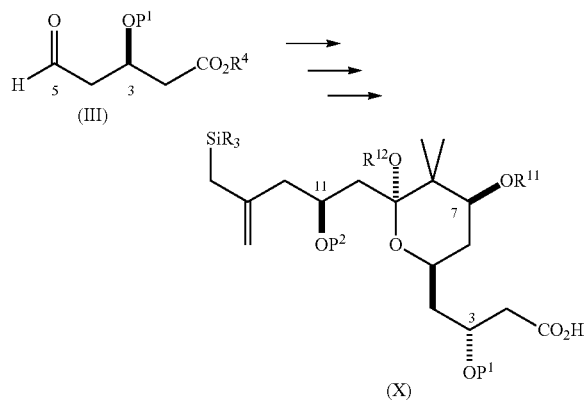

wherein:

$P^1$ and $P^2$ are independently H or a hydroxyl protecting group;

each R and $R^4$ is independently H, an alkyl or a substituted alkyl;

$R^{12}$ is an alkyl or a substituted alkyl; and $R^{11}$ is an acyl, a substituted acyl, an alkyl or a substituted alkyl.

In certain cases of formula (III), $P^1$ is a silyl ether protecting group. In certain cases, $P^1$ is t-butyldiphenylsilyl (TBDPS). In some cases, $R^4$ is an alkyl or a substituted alkyl, such as methyl or tert-butyl. It is understood that in certain embodiments of the subject methods, the compound of formula (III), or a synthetic precursor or equivalent synthon can be prepared via any convenient methods (e.g., by adapting the methods described in Tet. Lett. 2009, 50, 2094-2096; J. Nat. Prod. 2012, 75, 181-188; Bulletin of the Chemical Society of Japan 1989, 62, 3513-3517; Tet. Lett. 1998, 39, 249-252; and/or J. Org. Chem. 2007, 72, 9736-9745), and utilized as a starting material for the preparation of the Northern fragment.

In some embodiments, the method of preparing the Northern Hemisphere fragment includes preparing a compound of formula (V) from compounds of formulae (III) and (IV), e.g., via a stereoselective aldol reaction:

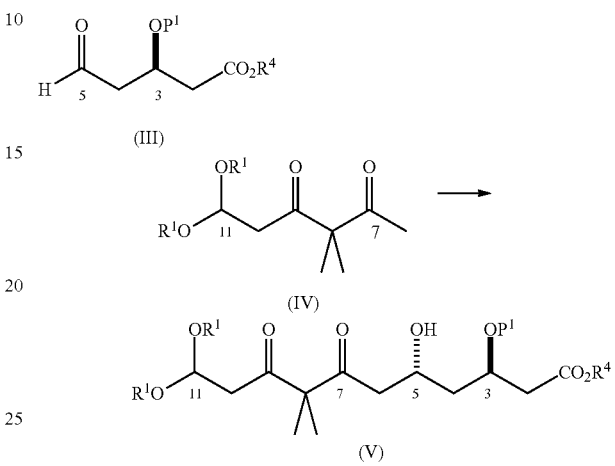

where each $R^1$ and $R^4$ is independently H, an alkyl or a substituted alkyl and $P^1$ is a hydroxyl protecting group. In certain cases of formulae (III) and (V), $P^1$ is a silyl ether protecting group. In certain cases, $P^1$ is t-butyldiphenylsilyl (TBDPS). In some cases, each $R^1$ is an alkyl or a substituted alkyl, such as ethyl. In some cases, $R^4$ is an alkyl or a substituted alkyl, such as methyl or tert-butyl. In some instances, compound of formula (V) can be prepared with at least a 2:1 diastereomeric ratio (dr) at C5, such as 3:1, 4:1, 5:1, 9:1, 19:1 or greater dr at C5. In some instances, compound of formula (V) can be prepared under conditions sufficient to achieve a 70% yield or more by molarity, such as 80% or more, 85% or more, or 90% or more, from the compound of formula (III). In some instances, compound of formula (V) can be prepared under conditions sufficient to achieve an 86% yield with a 2:1 dr at C5. In some instances, the compound of formula (V) is in equilibrium with its hemiketal isomer. Reaction conditions of interest include, but are not limited to, contacting the starting materials with reagents $Et_2B$-OTf/DIPEA (diisopropylethylamine) in a suitable solvent, such as a mixture of diethyl ether in a hydrocarbon solvent (e.g., approximately 20% diethyl ether/hydrocarbon). In some instances, the reaction procedure includes a particular order of addition of reagents, for example, firstly addition of the $Et_2B$-OTf to compound (IV), and after stirring for approximately 10 minutes, addition of DIPEA. After that, the mixture is stirred and compound (III) can be added. The reaction can be performed using a mixture of diethyl ether in a hydrocarbon solvent (e.g., approximately 20% v/v) at cold temperature, e.g., −78 C or −98 C. In some cases, the reaction can be quenched with MeOH at temperatures below −60° C. In some cases, the progress of the reaction can be followed by particular color changes. For example, after addition of the $Et_2B$-OTf to compound (IV) the reaction mixture turned pale yellow, after the subsequent addition of DIPEA the reaction mixture gradually turned orange-red, and after the addition of compound (III), the reaction mixture turned dark yellow. In certain instances of the method, a stereoselective aldol reaction is performed under reaction conditions that are not conventional Paterson aldol or Mukaiyama conditions. In certain instances, conventional Paterson aldol conditions led to reduction of the C9 carbonyl group of a compound of formula (IV). In some instances, conventional Mukaiyama and metal-enolate conditions led to complex mixtures with poor dr. However, the complex aldol reaction described herein rapidly brings together a majority of the Northern fragment in a single step, which provides an overall low step count and allows for throughput on multigram scales. The compound of formula (IV) can be prepared from commercially available starting materials via any convenient methods.

In some embodiments, the method of preparing the Northern Hemisphere fragment includes preparing a compound of formula (VI) from a compound of formula (V):

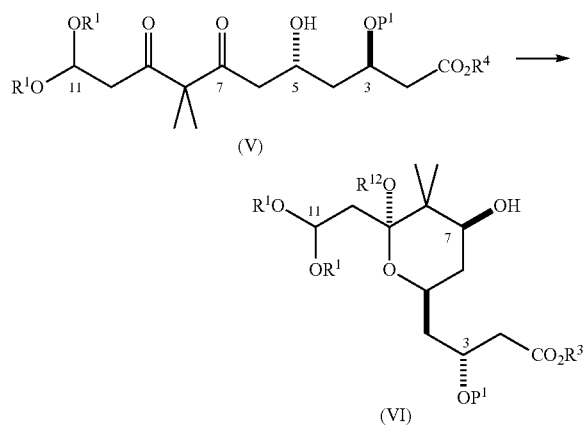

where each $R^1$, $R^3$, $R^4$ and $R^{12}$ $P^1$ are independently H, an alkyl or a substituted alkyl; and $P^1$ is a hydroxyl protecting group. This conversion can be performed in two steps via a highly diastereoselective (Evans-Saksena) ketone reduction (e.g., using a reducing agent such as sodium triacetoxyborohydride, in a mixed solvent system, such as of acetone, acetonitrile, and acetic acid), followed by a pyran forming cyclization to the bryostatin A ring (e.g., using a dehydrating agent, such as trimethylorthoformate). In certain instances, compound of formula (VI) can be prepared with at least a 15:1 diastereomeric ratio (dr) at C7. In certain instances of formula (VI), $R^{12}$ is alkyl or substituted alkyl, such as methyl. In certain cases of formulae (V) and (VI), $P^1$ is a silyl ether protecting group. In certain cases, $P^1$ is t-butyldiphenylsilyl (TBDPS). In some cases, each $R^1$ is an alkyl or a substituted alkyl, such as ethyl. In some cases, $R^4$ is an alkyl or a substituted alkyl, such as methyl or tert-butyl.

In some embodiments, the method of preparing the Northern Hemisphere fragment includes preparing a compound of formula (VII) from a compound of formula (VI):

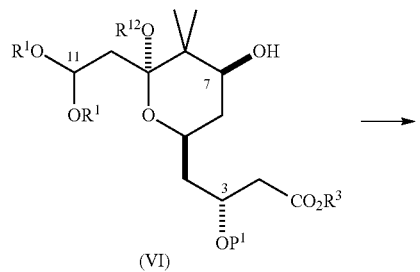

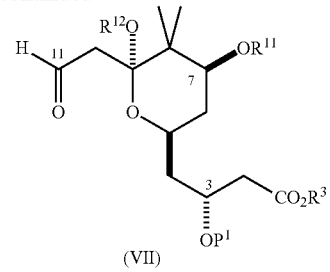

wherein $P^1$ is H or a hydroxyl protecting group; $R^{12}$ is alkyl or substituted alkyl; $R^{11}$ is acyl, substituted acyl, alkyl or substituted alkyl; and each $R^1$ and $R^3$ is independently H, alkyl or substituted alkyl. In certain instances of formulae (VI) and (VII), each $R^1$ and $R^3$ is methyl. In certain cases of formulae (VI) and (VII), $P^1$ is a silyl ether protecting group. In certain cases, $P^1$ is t-butyldiphenylsilyl (TBDPS). In some cases, this conversion is performed via a one-flask C7 alcohol acetylation and chemoselective C11 acetal hydrolysis to produce the compound of formula (VII). In certain cases, the reaction conditions of the subject method provides for the selective hydrolysis of the less substituted C11 acetal in the presence of C9 ketal.

It is understood that a number of synthetic equivalents for a compound of formula (VI) and (VII) are possible. For example, synthetic equivalents for the C11 acetal include, but are not limited to, cyclic acetals, 1,3-dithianes, 1,3-dithiolanes, thiacetals, oximes and imines. Any group that acts to protect the aldehyde at C11 in formula (VII) is possible.

In some embodiments of formula (VII), $R^3$ and $R^{12}$ are independently an alkyl, $R^{11}$ is an acyl and $P^1$ is silyl ether protecting group. In some embodiments of formula (VII), $R^3$ and $R^{12}$ are each methyl, $R^{11}$ is acetyl and $P^1$ is t-butyldiphenylsilyl (TBDPS).

In some embodiments, the method of preparing the Northern Hemisphere fragment includes reacting a compound of formula (VII) with a compound of formula (VIII) to stereoselectively produce a compound of formula (IX):

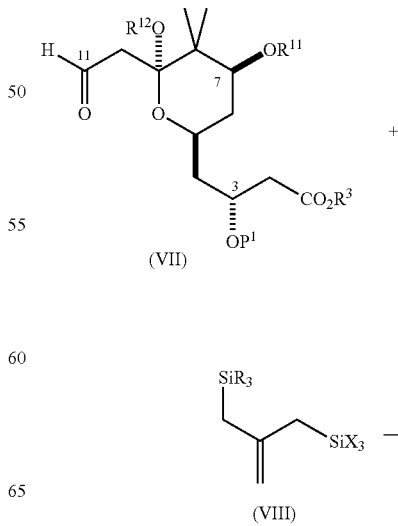

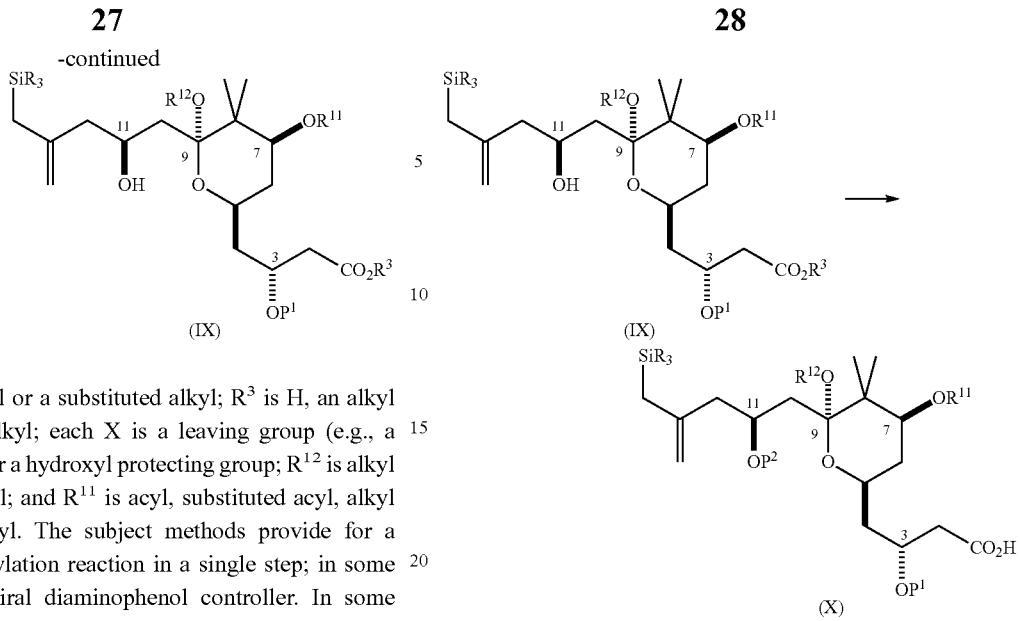

wherein: R is alkyl or a substituted alkyl; R³ is H, an alkyl or a substituted alkyl; each X is a leaving group (e.g., a halogen); P¹ is H or a hydroxyl protecting group; R¹² is alkyl or substituted alkyl; and R¹¹ is acyl, substituted acyl, alkyl or substituted alkyl. The subject methods provide for a stereoselective allylation reaction in a single step; in some cases, using a chiral diaminophenol controller. In some cases, the diaminophenol controller is Leighton's chiral diamine controller. In certain instances of formulae (VII)-(IX), each R and R³ is methyl. In certain cases of formulae (VII)-(IX), P¹ is a silyl ether protecting group. In certain cases, P¹ is t-butyldiphenylsilyl (TBDPS). In some instances of formulae (VIII) and (IX), each X is chloro.

In some embodiments of formula (IX), each R, R³ and R¹² are independently an alkyl, R¹¹ is an acyl and P¹ is silyl ether protecting group. In some embodiments of formula (IX), each R, R³ and R¹² are methyl, R¹¹ is acetyl and P¹ is t-butyldiphenylsilyl (TBDPS).

The compound of formula (IX) can be prepared using the subject methods under conditions sufficient to produce a 9:1 or greater ratio of (11S)- to (11R)-diastereoisomer of the compound of formula (IX), such as 19:1 or greater, 49:1 or greater, 99:1 or greater, or even greater. Any convenient methods can be used to assess the ratio of diastereoisomers present in a composition, such as ¹H NMR spectroscopic methods.

The compound of formula (IX) can be prepared using the subject methods under conditions sufficient to obtain a 70% or greater yield (by molarity) from the compound of formula (VII), such as 75% or greater, 80% or greater, 85% or greater, 90% or greater, 95% or greater yield, or even greater. In some instances, the compound of formula (IX) can be prepared using the subject methods under conditions sufficient to obtain 84% yield and 10:1 dr at C11. The compound of formula (IX) can be prepared using the subject methods under conditions sufficient to: (a) avoid oligomerizing the compound of formula (VIII); (b) avoid ionizing the C9 ketal; and/or (c) avoid proto-desilylating the newly-formed allylsilane during workup. For example, exemplary reaction conditions are described herein in the examples section.

In some embodiments, the method of preparing the Northern Hemisphere fragment includes preparing a compound of formula (X) from a compound of formula (IX):

wherein: each R is alkyl or a substituted alkyl; R³ is H, an alkyl or a substituted alkyl; P¹ and P² are independently a hydroxyl protecting group; R¹² is alkyl or substituted alkyl; and R¹¹ is acyl, substituted acyl, alkyl or substituted alkyl. This conversion can be performed via a C11 hydroxyl group protection method, followed by a chemoselective C1 ester hydrolysis, or vice versa. In some instances, a C11 hydroxyl group protection (e.g., silylation) and a C1 ester hydrolysis are conducted in either order. In some cases, the C11 silylation and a C1 ester hydrolysis are telescoped in a one-flask step. In certain cases of formulae (X), P² is a silyl ether protecting group. In certain cases, P² is triethylsilyl (TES). In certain cases of formula (X), P¹ is a silyl ether protecting group. In certain cases, P¹ is t-butyldiphenylsilyl (TBDPS). In some cases, a compound of formula (X) is prepared from a compound of formula (I) in 10 steps. In some cases, a compound of formula (X) is prepared from a compound of formula (I) in 13% or greater overall yield, such as 14% or greater, such as 15% or greater, 16% or greater, or even greater.

It is understood that the compound of formula (X) could be a synthetic equivalent thereof. For example, the C1 acid in the compound of formula (X) could be a protected derivative. In some cases, the C1 acid is protected with a labile protecting group, such that the free acid at C1 is generated in situ during the subsequent coupling of the compound of formula (X) and the compound of formula (XX).

In some cases, the preparation of the compound of formula (X) is performed using particular reaction and/or workup conditions. In some cases, compound X (bearing the C1 carboxylic acid) can be prone to decomposition under acidic conditions as well as when stored neat (i.e. not in solution). It has been found that the C9 methyl ketal is particularly prone to hydrolysis (i.e. R¹² is converted from Me to H) after the C1 ester is hydrolyzed. In some instances, the workup of this reaction includes neutralization, e.g., under mild conditions. In addition, chromatography with buffered (e.g., pH 7.0) silica gel can be performed. Under certain conditions, it has been found that the C7 acyl group is particularly prone to hydrolysis (i.e. R¹¹ C(O)Me group is converted to H). In some cases, the reaction is performed with trimethyltin hydroxide, and only run to partial conversion to minimize concomitant cleavage of the C7 acetate. In some cases, the reaction is performed with trimethyltin hydroxide, and after full conversion to the C1 carboxylic acid, an acetylation reaction (e.g. with acetic anhydride and DMAP) is carried out in the same reaction flask to re-esterify C7 and provide the compound of formula (X).

The Southern Hemisphere fragment can be prepared from commercially available starting materials, such as 3,4-dihydro-2H-pyran and prenyl bromide. In some cases, the total synthetic step count to complete the southern fragment is 20 steps or less from these reagents, such as 19 steps or less, 18 steps or less, 17 steps or less, 16 steps or less, 15 steps or less, 14 steps or less, 13 steps or less, or even less. In some cases, the total synthetic step count to complete the southern fragment is 13 steps or less from these reagents. In some cases, the total synthetic step count to complete the southern fragment is 12 steps from these reagents. A variety of compounds can be utilized as a starting material in the preparation of the Southern Hemisphere fragment according to the subject methods. Starting materials of interest include, but are not limited to, one of the following compounds, or a synthetic precursor or synthon thereof:

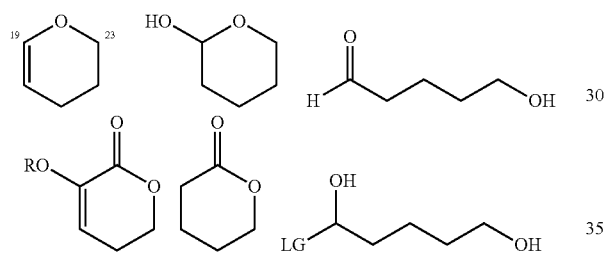

wherein R is H, or any convenient hydroxyl substituent (e.g., an alkyl or a substituted alkyl) and LG is any convenient leaving group (i.e. bisulfite adduct). It is understood that the methods and procedures described herein can be adapted to utilize any one of the starting materials. The subject methods are meant to include methods of preparing the Northern and/or Southern fragments where one or more (e.g., 1, 2, 3, 4, 5, 6, 7, 8, 9, 10 or more) of the individual steps described herein (e.g., one or more of the steps represented in FIGS. 1 and 2) are adapted and combined to produce the fragments. As such, also included are methods of preparing the Northern and Southern fragments where any one of the intermediate compounds described herein can be utilized as a starting material, and which can be prepared via any convenient alternative methods.

In some embodiments, the method comprises preparing a compound of formula (XX) from a starting material of formula (XI):

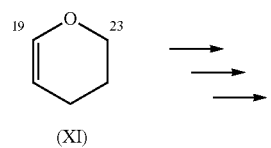

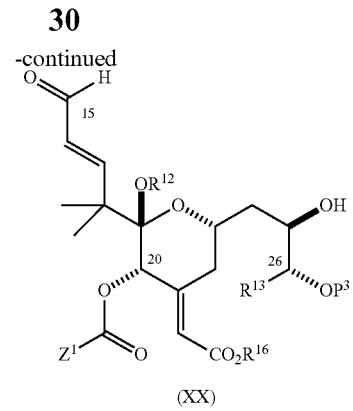

wherein:
Z$^1$ is an alkynyl or an allenyl;
R$^{12}$ and R$^{16}$ are independently H, an alkyl or a substituted alkyl;
R$^{13}$ is an alkyl or a substituted alkyl; and
P$^3$ is H or a hydroxyl protecting group.

In some embodiments, the method comprises preparing a compound of formula (XX) from a starting material of formula (XI):

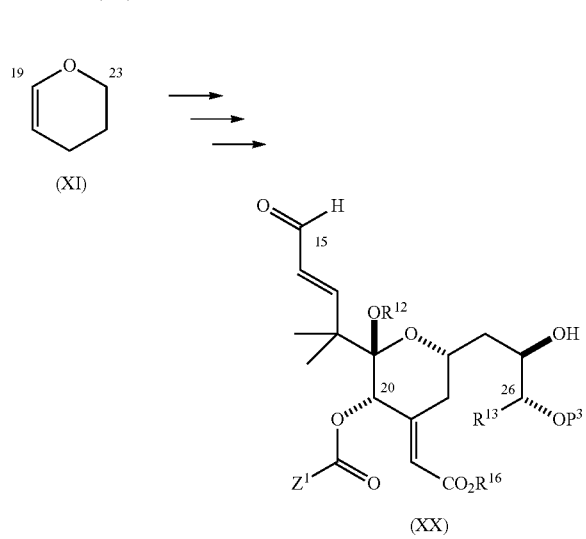

wherein:
Z$^1$ is an alkenyl, a substituted alkenyl, an alkynyl, a substituted alkynyl, an allenyl, a substituted allenyl, an aryl, a substituted aryl, a heteroaryl, a substituted heteroaryl, an alkyl, a substituted alkyl, or a carbon chain containing oxygen or nitrogen atoms, and/or rings and substituted rings included cycloalkyl, cycloalkenyl and the like (e.g., a PEG or modified PEG group);
R$^{12}$ and R$^{16}$ are independently H, an alkyl or a substituted alkyl;
R$^{13}$ is an alkyl or a substituted alkyl; and
P$^3$ is H or a hydroxyl protecting group. In some embodiments, Z$^1$ is W$^1$ as defined herein.

It is understood that the compound of formula (XX) could be a synthetic equivalent thereof. For example, the C25 free alcohol in the compound of formula (XX) could be a protected derivative. In some cases, the C25 alcohol is protected with a labile protecting group, such that the free alcohol at C25 is generated in situ during the subsequent coupling of the compound of formula (XX) and the compound of formula (X).

In some embodiments of Formula (XX), $Z^1$ is an alkynyl. In certain instances of Formula (XX), $Z^1$ is an α-β-alkyne or a substituted α-β-alkyne. In certain cases of Formula (XX), $Z^1$ is a β-γ-alkyne or a substituted β-γ-alkyne. In some embodiments of Formula (XX), $Z^1$ is an allenyl. In certain instances of Formula (XX), $Z^1$ is an α-β-γ-allene or a substituted α-β-γ-allene. In some embodiments of Formula (XX), $Z^1$ comprises 4-10 carbons, such as 4, 5, 6, 7, 8, 9 or 10 carbon atoms. In some embodiments of Formula (XX), $Z^1$ is:

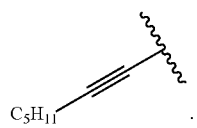

In some embodiments of Formula (XX), $R^{12}$ is H. In some instances of Formula (XX), $R^{13}$ is an alkyl. In some cases of Formula (XX), $R^{13}$ is methyl. In some instances of Formula (XX), $R^{16}$ is an alkyl. In some cases of Formula (XX), $R^{16}$ is methyl. In certain cases of formula (XX), $P^3$ is a silyl ether protecting group. In certain cases, $P^3$ is t-butyldiphenylsilyl (TBDPS). In certain cases, $P^3$ is t-butyldimethylsilyl (TBS).

Any convenient number of steps can be performed in order to prepare a compound of formula (XX) from a starting material of formula (XI). In some instances, 20 synthetic steps or less can be utilized, such as 15 synthetic steps or less, 14 synthetic steps or less, 13 synthetic steps or less, 12 synthetic steps or less, or even less. In some instances, a compound of formula (XX) can be referred to as a Southern Hemisphere fragment of a target bryostatin compound. FIG. 2 illustrates one possible sequence of steps (e.g., steps 1 to 13) that can be used. In certain instances, the method includes preparing a compound of formula (XX) from a starting material of formula (XI) via 13 synthetic steps of the type exemplified in FIG. 2. In some cases, a compound of formula (XX) is prepared from a compound of formula (XI) in 13 steps. In some cases, a compound of formula (XX) is prepared from a compound of formula (XI) in 16% or greater overall yield, such as 17% or greater, such as 18% or greater, 20% or greater, or even greater. It is understood that based on the present disclosure, variations of the synthetic strategy, the protecting groups, the reagents and reaction conditions depicted in the figures are possible.

In some embodiments, the method of preparing the Southern Hemisphere fragment includes preparing a compound of formula (XII) from a compound of formula (XI):

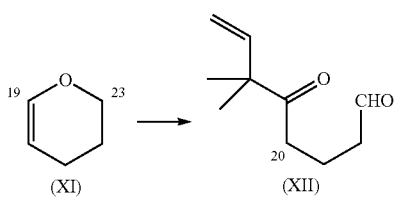

In some cases, the subject methods provide for prenylation of 3,4-dihydro-2H-pyran with prenyl bromide to afford a linear octenyl diol, followed by a double-oxidation of the diol to form an octenyl keto-aldehyde (XII). In some cases, the subject method provides for hydrolysis of 3,4-dihydro-2H-pyran (e.g., at a mild pH), followed by in situ prenylation, e.g., with prenyl bromide. In certain instances, the method includes prenylation performed at a mild pH of between about 3 and 5, such as between about pH 3 and 4, or between about 3.5 and 4. In certain instances, the reaction yield obtained is better than what can be achieved using conventional methods, and the material can be used in the next step without purification. In some cases, any convenient oxidation agent can be utilized in the double-oxidation step that has comparable oxidation rates for primary and secondary alcohols to avoid oxidative lactonization. In certain instances, the product (XII) is purified before further use. In certain cases, the double-oxidation reaction is carried out on greater than 25 g of starting material and proceeds in greater than 80% yield.

In certain embodiments, the method of preparing the Southern Hemisphere fragment includes preparing a compound of formula (XIV) from compounds of formula (XII):

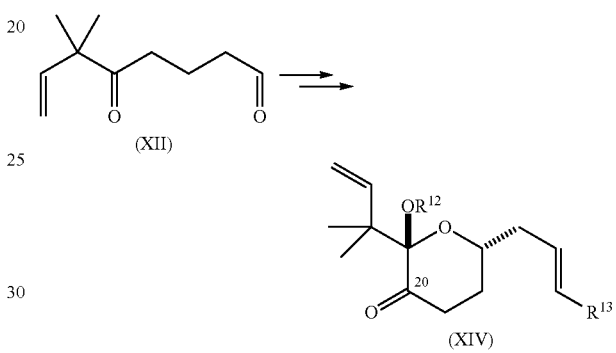

where $R^{12}$ is H, an alkyl or a substituted alkyl; and $R^{13}$ is an alkyl (e.g., as alkyl comprising at least two carbons) or a substituted alkyl. In certain instances, $R^{12}$ is alkyl or a substituted alkyl, such as methyl. Any convenient methods can be utilized to prepare a compound of formula (XIV) from formula (XII). In some embodiments, a method is used that includes a non-selective linear crotylation, followed by oxidation of the resulting alcohol, and stereoselective reduction to set the C23 stereocenter of the compound of formula (XIV). In some instances the C23 stereocenter is set with high chemo- and enantioselectivity (e.g. greater than 98% ee). In certain instances, a metathesis reaction can be used to incorporate an $R^{13}$ group of interest.

In certain embodiments, the method of preparing the Southern Hemisphere fragment includes preparing a compound of formula (XIVb) from compounds of formula (XII) and (XIII) via intermediate (XIVa):

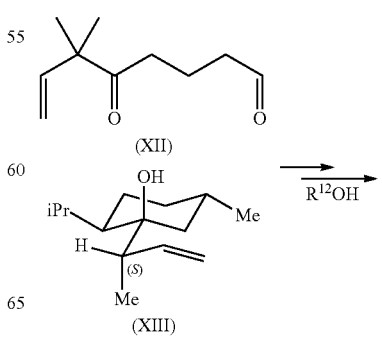

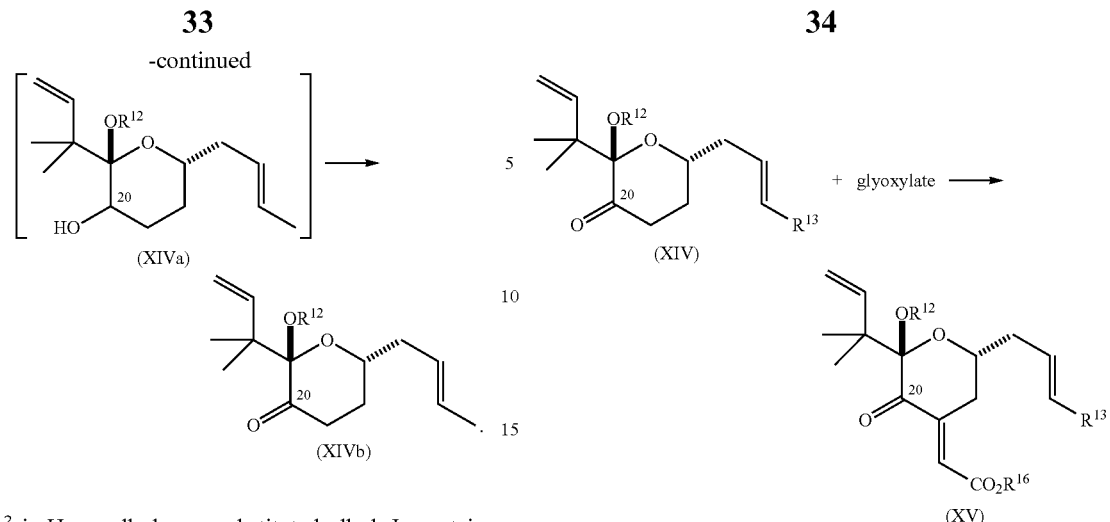

where $R^{12}$ is H, an alkyl or a substituted alkyl. In certain instances, $R^{12}$ is alkyl or a substituted alkyl. In certain instances, $R^{12}$ is methyl. The preparation of the compound of formula (XIVb) can be performed via a multi-reaction sequence, e.g., involving a stereoselective crotylation of the aldehyde, a pyran-forming cyclization using the same acid and solvent used as in previous reaction, and oxygenation of the pyran through an epoxidation/methanolysis sequence. The subject methods provide for combining these reactions together in a single flask, thus reducing the overall step count and minimizing waste and loss of material in workups and transfers. In certain instances, crude compound of formula (XIVa) may be oxidized to a compound of formula (XIVb). In some cases, mild oxidation reagents may be employed, e.g. Dess-Martin periodinane. In some cases, a compound of formula (XIV) is prepared in 4 Steps from a compound of formula (XI) and is the first intermediate in the sequence that requires chromatographic purification.

In certain instances, the method of preparing the Southern Hemisphere fragment includes preparing a compound of formula (XIV) from a compound of formula (XIVb) via a metathesis reaction:

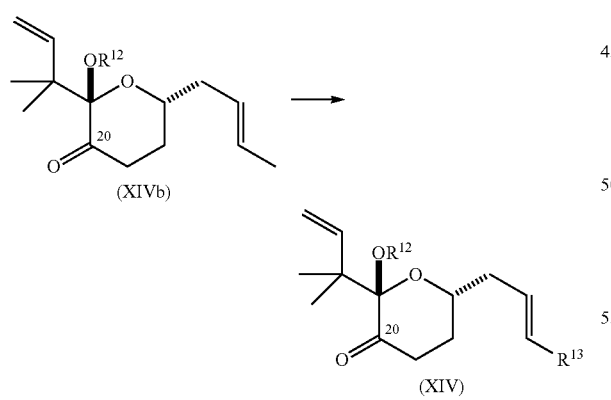

wherein $R^{12}$ is H, an alkyl or a substituted alkyl; and $R^{13}$ is an alkyl (e.g., as alkyl comprising at least two carbons) or a substituted alkyl. In certain instances, $R^{12}$ is alkyl or a substituted alkyl, such as methyl.

In certain instances, the method of preparing the Southern Hemisphere fragment includes preparing a compound of formula (XV) from a compound of formula (XIV):

wherein $R^{12}$ is H, an alkyl or a substituted alkyl; $R^{13}$ is an alkyl (e.g., methyl or an alkyl comprising at least two carbons) or a substituted alkyl; and $R^{16}$ is H, an alkyl or a substituted alkyl. The conversion can be achieved via an aldol reaction with glyoxylate, hemi-acetal of glyoxylate, and/or glyoxylate acetals to install an exocyclic enoate of formula (XV). In some instances, the E-isomer was exclusively formed. In some instances of the method, low amounts of methanol are used in the aldol reaction, and the glyoxylate is freshly distilled before use to eliminate polymer materials. In certain instances of formulae (XIV) and (XV), $R^{13}$ is methyl. In certain instances of formulae (XIV) and (XV), $R^{13}$ is an alkyl comprising at least two carbons or a substituted alkyl. In certain instances of formulae (XIV) and (XV), $R^{12}$ is alkyl or a substituted alkyl. In certain instances, $R^{12}$ is methyl. In certain instances, $R^{16}$ is alkyl or a substituted alkyl. In certain instances, $R^{16}$ is methyl.

In certain instances, the method of preparing the Southern Hemisphere fragment includes preparing a compound of formula (XVI) from a compound of formula (XV):

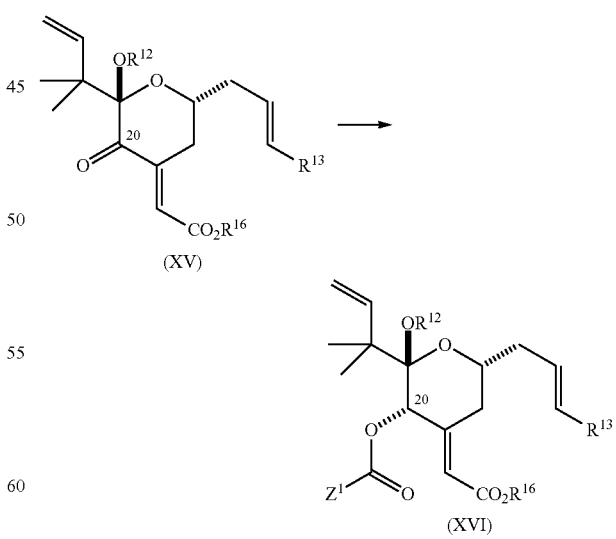

where $Z^1$ is an alkynyl or an allenyl; $R^{12}$ is an alkyl or a substituted alkyl; $R^{13}$ is an alkyl (e.g., methyl or an alkyl comprising at least two carbons) or a substituted alkyl; and $R^{16}$ is H, an alkyl or a substituted alkyl. The preparation of the compound of formula (XVI) can be performed via a stereoselective Luche reduction of the pyranyl ketone to an alcohol, followed by an esterification of the resulting pyranyl alcohol with a $Z^1$ anhydride of interest. In certain instances, the anhydride is octynoic anhydride. The anhydride can be purified prior to utilization in the reaction to provide an improved yield. In some instances, the alkynoate is a "masked dienoate" that provides for subsequent oxidative transformations of interest. As used herein, a masked dienoate is a synthetic precursor of a dienoate. Any convenient groups can be utilized as a masked dienoate. In some cases, careful temperature control of the esterification reaction (e.g., −20° C.) as well as rate of DMAP addition can be utilized to prevent decomposition of the reactive anhydride/DMAP adduct. In certain instances of formulae (XV) and (XVI), $R^{13}$ is methyl. In certain instances of formulae (XV) and (XVI), $R^{13}$ is an alkyl comprising at least two carbons or a substituted alkyl. In certain instances of formulae (XV) and (XVI), $R^{12}$ is alkyl or a substituted alkyl. In certain instances, $R^{12}$ is methyl. In certain instances of formulae (XV) and (XVI), $R^{16}$ is alkyl or a substituted alkyl. In certain instances, $R^{16}$ is methyl. In some embodiments of Formula (XVI), $Z^1$ is an alkynyl. In certain instances of Formula (XVI), $Z^1$ is an α-β-alkyne or a substituted α-β-alkyne. In certain cases of Formula (XVI), $Z^1$ is a β-γ-alkyne or a substituted β-γ-alkyne. In some embodiments of Formula (XVI), $Z^1$ is an allenyl. In certain instances of Formula (XVI), $Z^1$ is an α-β-γ-allene or a substituted α-β-γ-allene. In some embodiments of Formula (XVI), $Z^1$ comprises 4-10 carbons, such as 4, 5, 6, 7, 8, 9 or 10 carbon atoms. In some embodiments of Formula (XVI), $Z^1$ is:

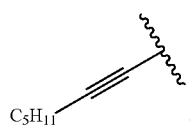

In certain instances, the method of preparing the Southern Hemisphere fragment includes preparing a compound of formula (XVII) from a compound of formula (XVI)

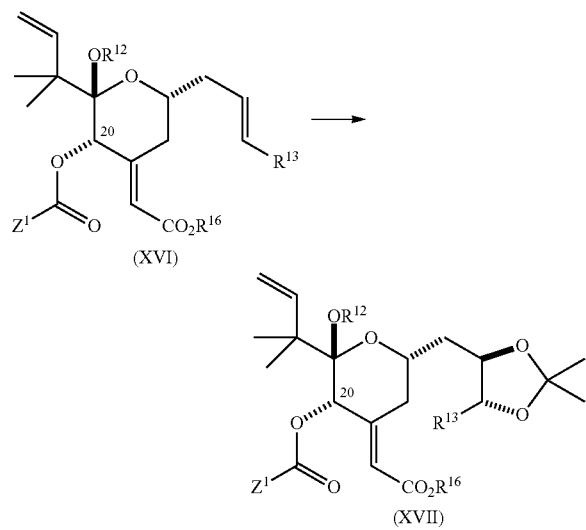

where $Z^1$ is an alkynyl or an allenyl; $R^{12}$ is an alkyl or a substituted alkyl; $R^{13}$ is an alkyl (e.g., methyl or an alkyl comprising at least two carbons) or a substituted alkyl; and $R^{16}$ is H, an alkyl or a substituted alkyl. The subject methods can provide for preparation of the compound of formula (XVI) via a stereo-, regio-, and chemoselective olefin (C25-C26) dihydroxylation to afford a diol intermediate, which is then protected, e.g., as an acetonide (formula XVII). In some cases, the diol is utilized without column purification. It is understood that a variety of protecting groups can be adapted for use in the subject methods to protect the diol intermediate. The subject method step provides for selective reaction of one out of four pi systems in the molecule to give the desired product in a high diastereomeric ratio (e.g., ~11:1 or higher).

In certain instances, the method of preparing the Southern Hemisphere fragment includes preparing a compound of formula (XVIII) from a compound of formula (XVII), e.g., via ozonolosis:

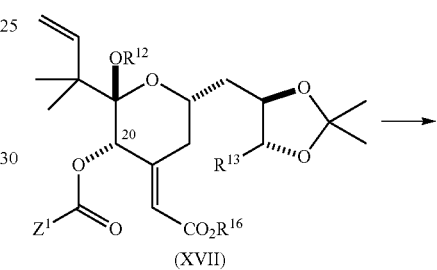

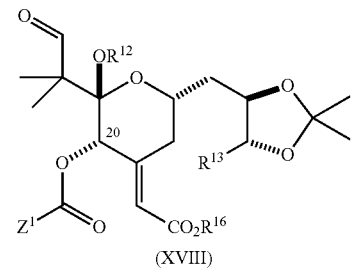

where $Z^1$ is an alkynyl or an allenyl; $R^{12}$ is an alkyl or a substituted alkyl; $R^{13}$ is an alkyl (e.g., methyl or an alkyl comprising at least two carbons) or a substituted alkyl; and $R^{16}$ is H, an alkyl or a substituted alkyl. The subject method step provides for an ozonolysis that proceeds with selective cleavage of the terminal alkene without noticeably affecting the other pi systems in the molecule. In some cases, the subject methods provide a 60% or more yield by molarity of the compound of formula (XVIII), such as 70% or more, 75% or more, 80% or more, 85% or more, 90% or more, or even more yield. In some cases, the subject methods provide a 93% yield by molarity of the compound of formula (XVIII).

In certain instances, the method of preparing the Southern Hemisphere fragment includes preparing a compound of formula (XIX) from a compound of formula (XVIII), e.g., via aldehyde homologation and C25/26 diol deprotection:

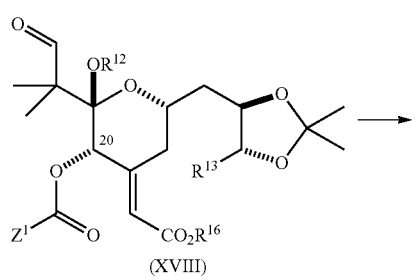

(XVIII)

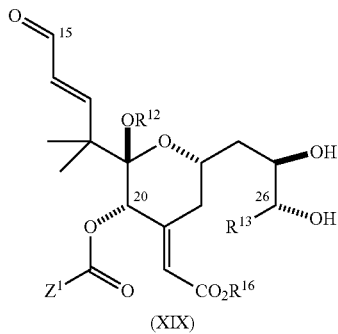

(XIX)

where $Z^1$ is an alkynyl or an allenyl; $R^{12}$ is an alkyl or a substituted alkyl; $R^{13}$ is an alkyl (e.g., methyl or an alkyl comprising at least two carbons) or a substituted alkyl; and $R^{16}$ is H, an alkyl or a substituted alkyl. The aldehyde homologation reaction can be performed using any convenient reagent, e.g., an organozinc reagent, such as EtO—CH=CH—ZnMe$_2$Li, a neutral vinyl zinc reagent or an organocerium reagent. In certain embodiments, the aldehyde homologation reaction is performed in a particular solvent mixture that provides for a high concentration of reagents. In certain instances, the reaction is performed using five equivalents or more (such as 6 or more, 7 or more, 8 or more, or 10 or more) of a zincate reagent relative to aldehyde. In certain instances, the aldehyde homologation and C25/C26 diol deprotection are performed in one flask. In certain instances, the aldehyde homologation and C25/26 diol deprotection are performed in two separate reaction flasks.

In some cases, the compound of formula (XIX) is converted to the compound of formula (XX) via a regioselective alcohol protection, e.g., to protect the C26 hydroxyl group with a silyl ether, such as TBS. In certain instances, purification of the reaction product is performed using neutralized silica to prevent decomposition. In certain embodiments, this step is optional and can be avoided, depending on when the stereoselective Prins macrocyclization (described below) is performed.

Figure 3:
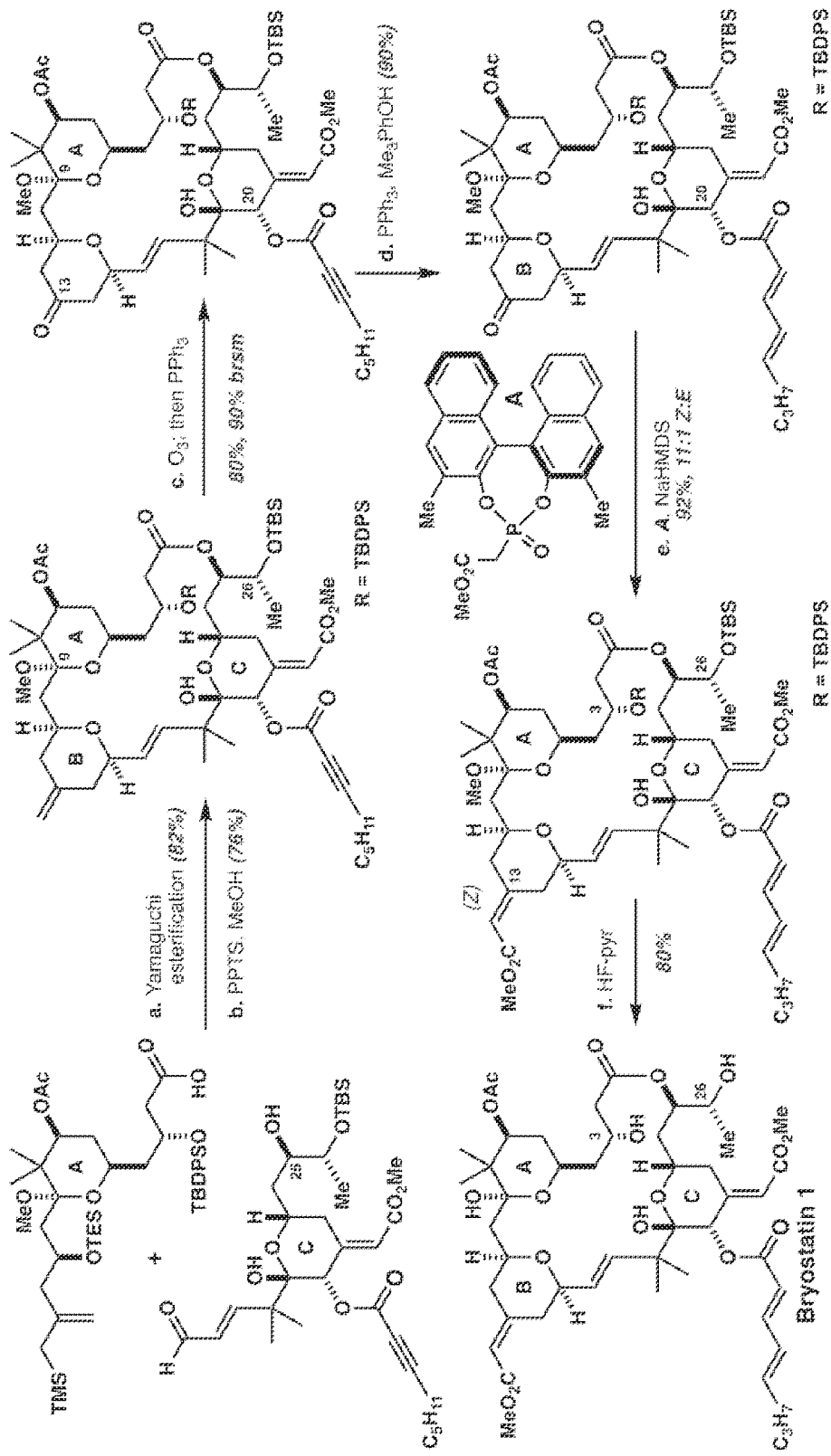
FIG. 3 depicts an exemplary reaction scheme for preparing bryostatin compounds from the Northern and Southern Hemisphere fragments.

FIG. 3 illustrates one exemplary strategy that can be applied to couple a Northern Hemisphere fragment and a Southern Hemisphere fragment of any convenient bryostatin compound. In general terms, fragments can be coupled via a Yamaguchi esterification between the C1 acid of the Northern fragment and the C25 alcohol of the Southern fragment. The macrocycle can then be cyclized via a stereoselective Prins macrocyclization. In certain instances, the coupling strategy can be reversed, e.g., performing the Prins macrocyclization first, followed by the macrolactonization. In some instances, the subject methods involve particular macrocyclization reaction conditions that are exceptionally mild and which provide for scalability of the reaction. The resulting B ring exocyclic olefin can then be converted to a ketone via a stoichiometric ozonolysis reaction, which in some cases proceeds selectively in the presence of two other pi systems. The resulting B ring exocyclic olefin can be converted to a ketone via any convenient oxidative cleavage reaction.

It is understood that the free hydroxyl at C25 of the Southern fragment could be generated in situ under the reaction conditions for the Yamaguchi esterification reaction or the stereoselective Prins macrocyclization. Thus the C25 hydroxyl could be a protected hydroxyl group. It is also understood that the C1 acid in the Northern fragment could be generated in situ under the reaction conditions for the Yamaguchi esterification reaction or the stereoselective Prins macrocyclization. Thus the C1 acid could be a protected acid e.g. an ester. In some cases, the protecting group, if present at C25 and/or C1, is a labile group that is easily removed under mild reaction conditions. In some embodiments, the method further includes: (c) coupling the Northern Hemisphere fragment and the Southern Hemisphere fragment via esterification and macrocyclization to produce a macrocyclic compound; and (d) preparing a compound of formula (XXIV) from the macrocyclic compound via an ozonolysis reaction:

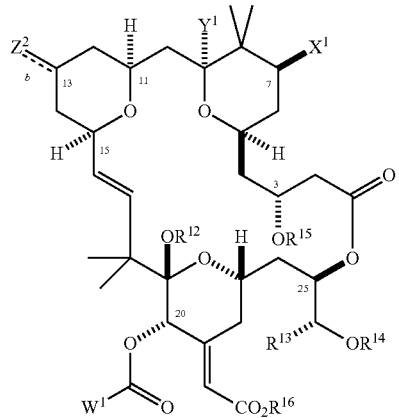

(XXIV)

wherein: $W^1$ is an alkenyl, a substituted alkenyl, an alkynyl, a substituted alkynyl, an alkyl, a substituted alkyl or a protecting group; $Z^2$ is =CR$^5$R$^6$ or =NR$^7$ when the covalent bond designated "b" is a double bond; $Z^2$ is —OR$^8$ or —N(R$^7$)$_2$ when the covalent bond designated "b" is a single bond; $X^1$ is H or OR$^{11}$; $Y^1$ is H or OR$^{12}$; $R^5$, $R^6$, $R^7$ and $R^8$ are each independently H, halogen (e.g., F), alkyloxycarbonyl (e.g., —CO$_2$Me), substituted alkyloxycarbonyl, alkyl or substituted alkyl; $R^{11}$ is an acyl, a substituted acyl, an alkyl or a substituted alkyl; $R^{12}$ is H, an alkyl or a substituted alkyl; $R^{13}$ is an alkyl or a substituted alkyl; $R^{14}$ and $R^{15}$ are independently H, a hydroxyl protecting group or a promoiety; and $R^{16}$ is H, an alkyl or a substituted alkyl.

In certain embodiments of formula (XXIV), $W^1$ is an alkynyl or a substituted alkynyl. In certain instances, where $W^1$ is an alkynyl or a substituted alkynyl, the method further includes isomerizing the alkynyl group of $W^1$ to a diene. Any convenient methods and conditions can be used to isomerize $W^1$ to a diene-containing group of interest (e.g., as described herein). In certain embodiments of formula (XXIV), $W^1$ is a protecting group which can be removed from the C20 hydroxyl group, prior to installation of a $W^1$ group of interest, such as an alkenyl or substituted alkenyl ester, e.g., a diene containing ester such as octadienoate.

In certain embodiments, the method further includes: (c) coupling the Northern Hemisphere fragment (e.g., a compound of formula (X)) and the Southern Hemisphere fragment (e.g., a compound of formula (XX)) via esterification and macrocyclization to produce a macrocyclic compound; and (d) preparing a compound of formula (XXII) from the macrocyclic compound via an ozonolysis reaction:

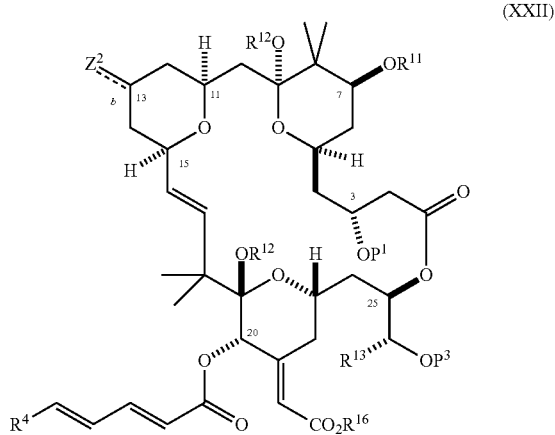

(XXII)

wherein:
R$^4$ is an alkyl or a substituted alkyl;
Z$^2$ is =CR$^5$R$^6$ or =NR$^7$ when the covalent bond designated "b" is a double bond;
Z$^2$ is —OR$^8$ or —N(R$^7$)$_2$ when the covalent bond designated "b" is a single bond;
P$^1$ and P$^3$ are independently H or a hydroxyl protecting group;
R$^5$, R$^6$, R$^7$ and R$^8$ are each independently H, halogen (e.g., F), alkyloxycarbonyl (e.g., —CO$_2$Me), substituted alkyloxycarbonyl, alkyl or substituted alkyl;
R$^{11}$ is H, an acyl, a substituted acyl, an alkyl or a substituted alkyl;
R$^{12}$ is H, an alkyl or a substituted alkyl;
R$^{13}$ is H, an alkyl or a substituted alkyl; and
R$^{16}$ is H, an alkyl or a substituted alkyl.

In certain embodiments of formula (XXII), R$^4$ is C$_3$H$_7$. In certain embodiments of formula (XXII), P$^1$ is a silyl ether protecting group. In certain cases, P$^1$ is t-butyldiphenylsilyl (TBDPS). In certain cases, P$^1$ is H. In certain embodiments of formula (XXII), P$^3$ is a silyl ether protecting group. In certain cases, P$^3$ is TBS. In certain cases, P$^3$ is TES. In certain cases, P$^3$ is H. In certain embodiments of formula (XXII), R$^{11}$ is an acyl or a substituted acyl. In certain embodiments of formula (XXII), R$^{11}$ is acetyl. In certain embodiments of formula (XXII), R$^{12}$ is an alkyl or a substituted alkyl. In certain embodiments of formula (XXII), R$^{12}$ is methyl. In certain embodiments of formula (XXII), R$^{16}$ is an alkyl or a substituted alkyl. In certain embodiments of formula (XXII), R$^{16}$ is methyl.

Figure 6A:
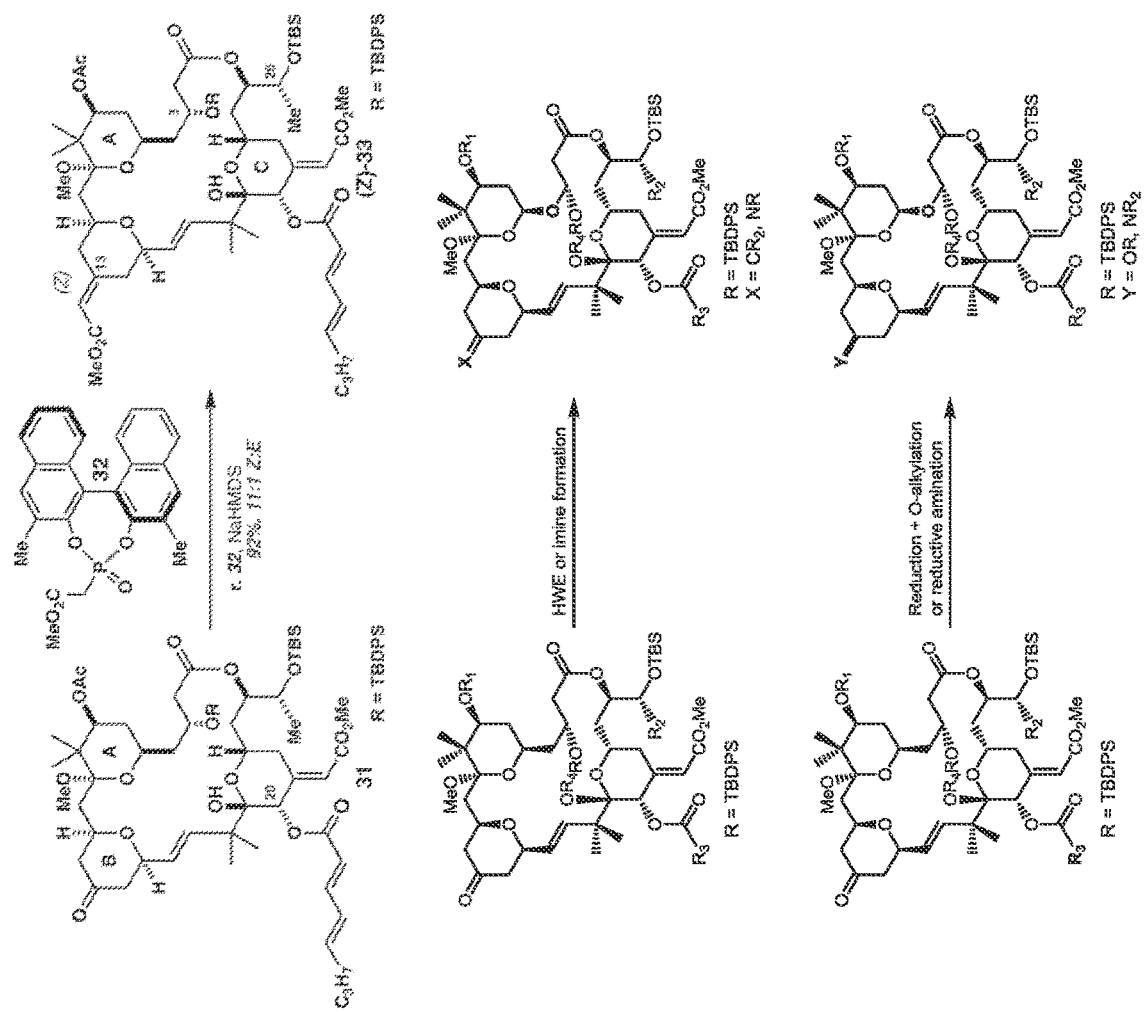
FIG. 6A to FIG. 6C illustrate exemplary synthetic schemes for preparation of C13 substituted analogs of bryostatin compounds, and C12 and C14 substituted analogs (FIG. 6C).
Figure 6B:
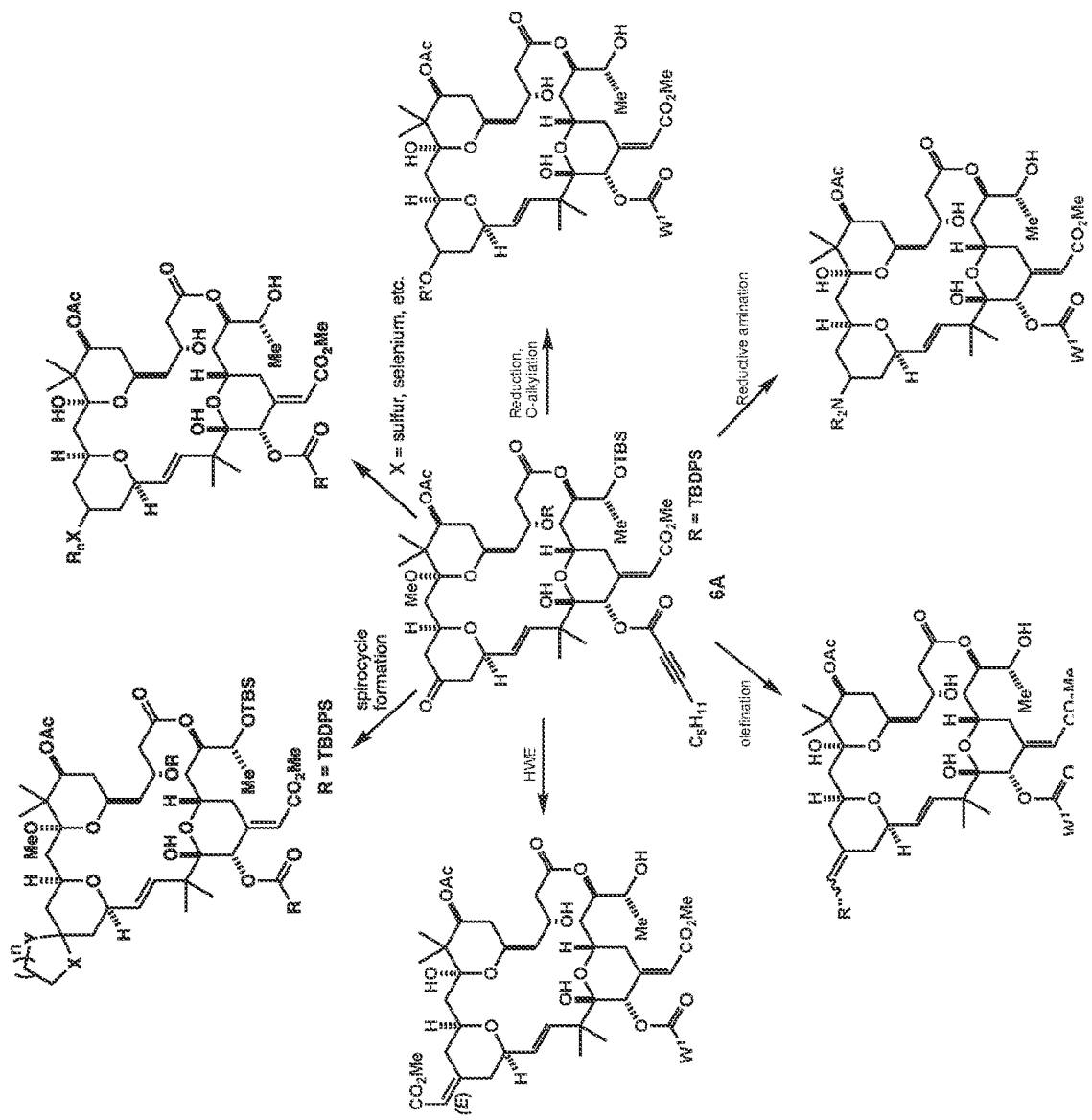
Figure 6C:
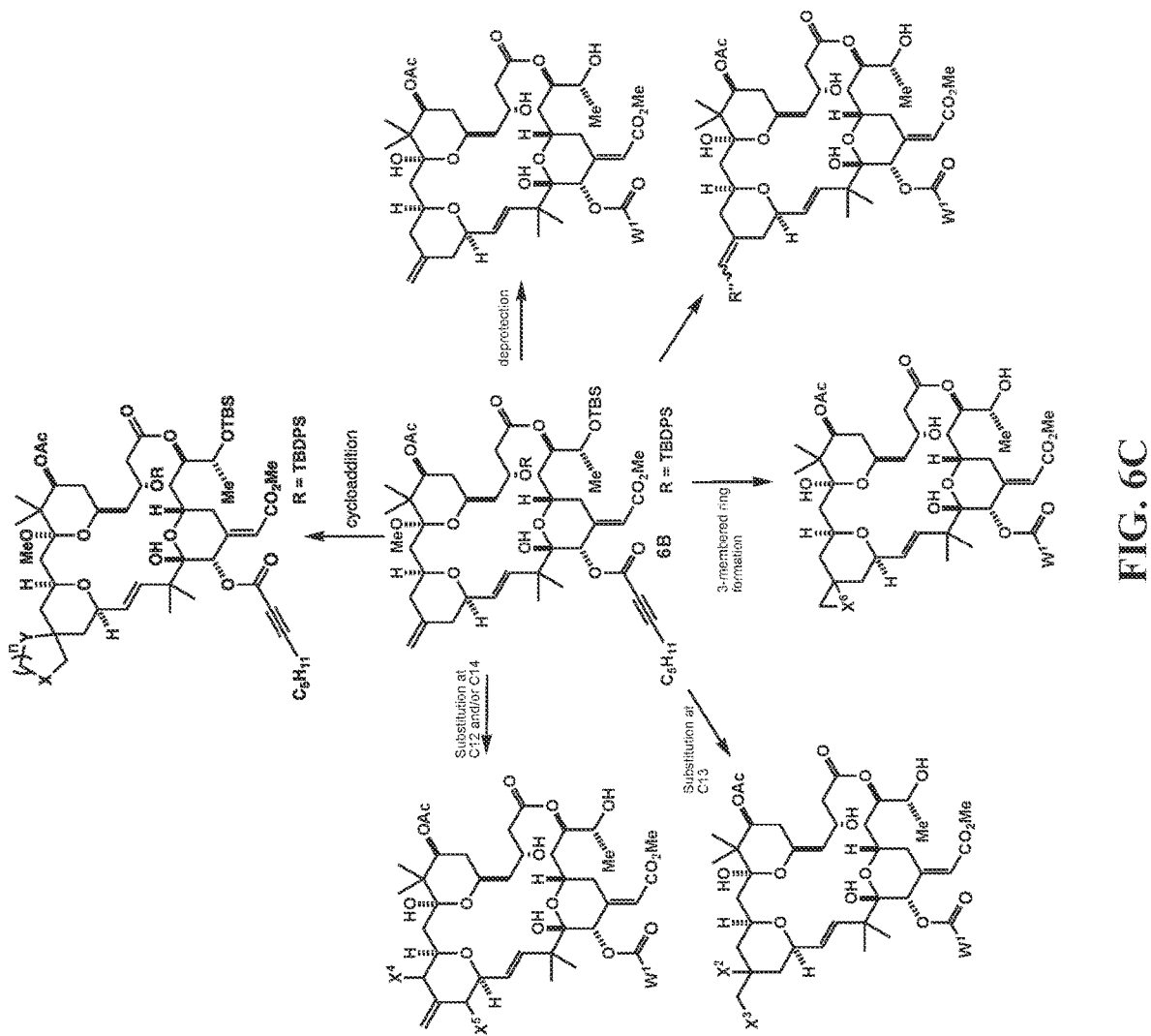

FIG. 6A to FIG. 6C illustrates some exemplary methods that can be adapted to install a variety of Z$^2$ substituents. In some cases, by altering the sequence between compounds 6 and 7 (FIG. 6A), variability at the C13 position can be readily accomplished, e.g., through olefination or imine formation. In some cases, the C13 ketone can be reduced to the alcohol and subsequently acylated or etherified. In certain instances, the C13 ketone can be modified via a reductive animation with any convenient amino reactant.

In certain embodiments of formula (XXII), the covalent bond designated "b" is a double bond and Z$^2$ is CR$^5$R$^6$ (e.g., CHCO$_2$Me) or NR$^7$. In certain instances, Z$^2$ is CR$^5$R$^6$. In certain cases, Z$^2$ is CHCO$_2$R' where R' is alkyl (e.g., methyl). In certain cases, Z$^2$ is CFCO$_2$R' where R' is alkyl (e.g., methyl). In certain instances, Z$^2$ is NR$^7$. In certain instances, Z$^2$ is NH. In certain instances, Z$^2$ is N-alkyl.

In certain embodiments of formula (XXII), the covalent bond designated "b" is a single bond and Z$^2$ is OR$^8$ or N(R$^7$)$_2$. In certain instances, Z$^2$ is OR$^8$. In certain cases, Z$^2$ is OH. In certain cases, Z$^2$ is O-acyl or O-(substituted acyl). In certain instances, Z$^2$ is N(R$^7$)$_2$. In certain cases, Z$^2$ is NH$_2$. In certain cases, Z$^2$ is N(alkyl)$_2$.

Any convenient protection and deprotection steps can be included in the subject methods to temporarily protect a functional group of interest, such as a hydroxy group or a carboxylic acid. In some instances, the subject method further comprised deprotecting a protected hydroxy group to produce a bryostatin compound having a free hydroxyl group. In certain instances, the C26 hydroxyl group is protected (e.g., using a silylether protecting group), and the method includes deprotection of the C26 hydroxyl.

In some instances, the subject method further includes installing a promoiety on the bryostatin compound to produce a prodrug version (e.g., as described herein) of the compound. "Promoiety" refers to a form of protecting group that, when used to mask a functional group within an active agent, converts the active agent into a prodrug. In some cases, the method includes protecting any convenient hydroxy group of the bryostatin compound (or a precursor thereof, e.g., as described herein) with a promoiety (i.e., —OH→—OP). In certain instances, —OP is an ether. In certain instances, —OP is a carbonate. In certain instances, —OP is a phosphate. In certain instances, —OP is an alkoxyphosphate. In certain instances, —OP is an ester. In certain embodiments, P is an acyl or a substituted acyl. In certain embodiments, P is —C(O)R$_{10}$, where R$^{10}$, R$_{20}$ and R$^{30}$ are each independently selected from hydrogen, unsubstituted or substituted C$_{1-6}$ haloalkyl, unsubstituted or substituted C$_{1-6}$ alkyl, unsubstituted or substituted C$_{3-6}$ cycloalkyl, unsubstituted or substituted C$_{2-6}$ alkenyl, unsubstituted or substituted C$_{2-6}$ alkynyl, unsubstituted or substituted C$_{6-10}$ aryl, unsubstituted or substituted 5- to 10-membered heteroaryl, unsubstituted or substituted aryl-C$_{1-4}$ alkyl, unsubstituted or substituted aryl-C$_{1-4}$ alkyl, unsubstituted or substituted aryloxy-C$_{1-4}$ alkyl, a unsubstituted or substituted polyethylene glycol. In certain cases, P is selected from one of the following groups: —COCH$_3$, —COC$_2$H$_5$, —COC(CH$_3$)$_3$, —CO$_2$CH(CH$_3$)$_2$, —CO$_2$CH$_3$ and —CO$_2$C$_2$H$_5$. In certain cases, P comprises a polyethylene glycol group. In certain cases, P comprises a lipid, such as a fatty acid or cholesterol. In some instances, P can include a peptide, a redox-labile group, a photochemically labile group, an enzymatically removable group (i.e. removable in situ by an enzyme selected from proteases, esterases, and phosphatases), or an antibody (e.g., antibody-drug conjugate).

In certain embodiments of the method, the macrocyclic compound is of formula (XXI):

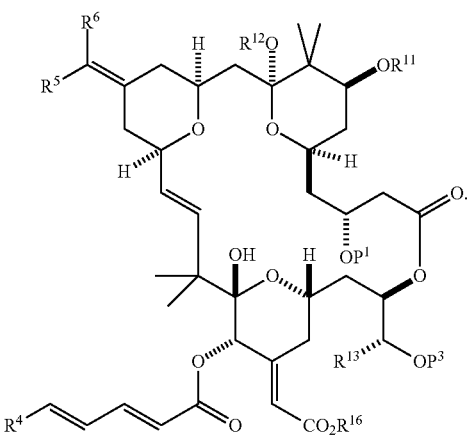

(XXI)

In certain embodiments of the method, the macrocyclic compound is of the formula:

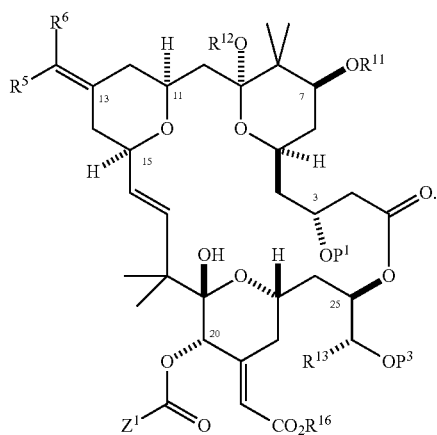

(XXIb)

In certain embodiments of the method, the bryostatin compound has the structure of formula (XXIII);

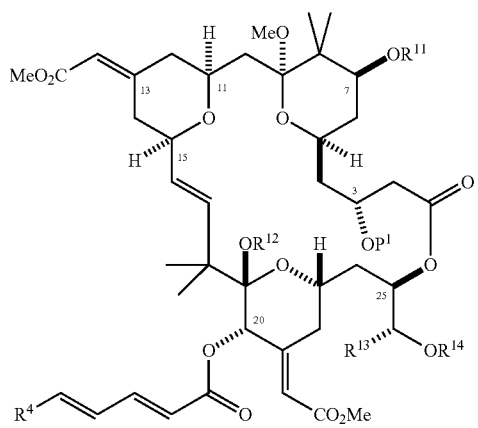

(XXIII)

wherein: $R^{13}$ is an alkyl or a substituted alkyl; and $R^{14}$ is H, a hydroxyl protecting group or a promoiety (e.g., P, as described herein).

In some instances of the formulae (I)-(XXIV), $R^{16}$ is methyl. In some instances of the formulae (I)-(XXIV), $R^{14}$ is H or a promoiety. In some instances of the formulae (I)-(XXIV), $R^{13}$ is methyl. In some instances of the formulae (I)-(XXIV), $R^{12}$ is methyl. In some instances of the formulae (I)-(XXIV), $R^{12}$ is H. In some instances of the formulae (I)-(XXIV), $R^{11}$ is acetyl. In some instances of the formulae (I)-(XXIV), $R^{4}$ is $C_3H_7$. In some instances of the formulae (I)-(XXIV), $P^{1}$ is H. In certain embodiments of the subject methods, the bryostatin compound that is produced is bryostatin 1.

Bryostatin Compounds

A variety of novel bryostatin compounds are described herein which are accessible via the subject methods. In some cases, the subject bryostatin compounds have activity as protein kinase C modulators both in vitro and in vivo. In some cases, the bryostatin compounds have PKC isoform selectivity. In certain instances, the bryostatin compounds bind to the C1 domain of PKC. In certain instances, the subject bryostatin compounds have activity as a modulator of a signaling protein target that includes a C1 domain. Any convenient C1 domain containing proteins can be targeted for modulation by the subject bryostatin compounds. Exemplary C1 domain containing proteins of interest include, but are not limited to, PKC, PKD, chimaerin, diacylglycerol kinase, Unc-13 and Munc-13, guanine nucleotide exchange factors, myotonic dystrophy kinase-related Cdc42-binding kinase, and the like.

Figure 4:
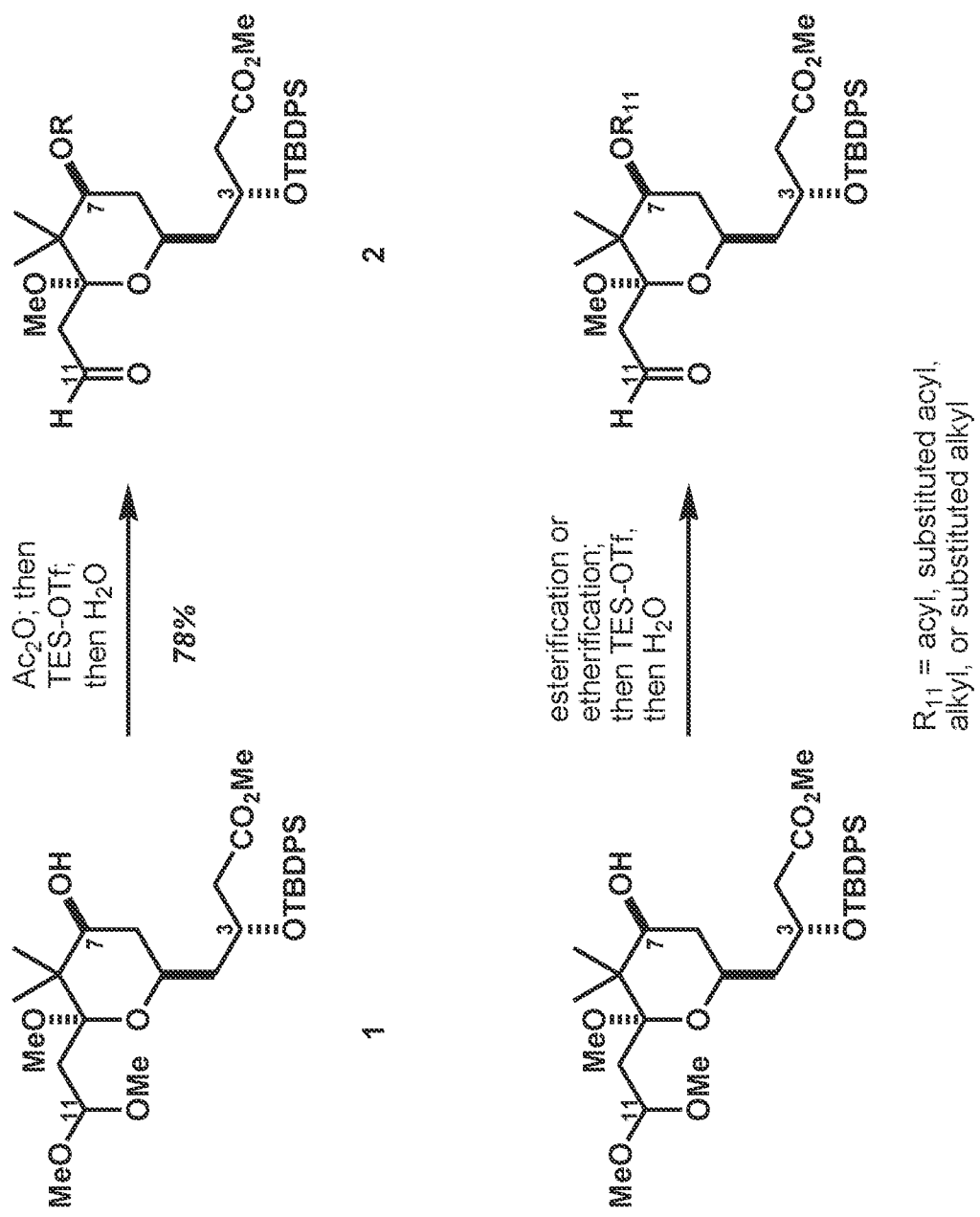
FIG. 4 illustrates an exemplary synthetic scheme for preparation of C7 ester analogs of bryostatin compounds.

Bryostatin compounds of interest include, but are not limited to, those compounds featuring variation of the C7 ester (see e.g., FIG. 4). By altering the sequence between compounds 1 and 2 (FIG. 4), any number of ester or ether substituents can be installed at the C7 position by changing the anhydride used for the esterification, or performing an etherification, e.g., with any number of alkyl bromides or other convenient etherification reagent. In some cases, the subject compounds have A-ring functionalization, e.g., at the C7 and C9 positions that is the same as a target naturally occurring bryostatin, such as bryostatin 1.

In some embodiments, the bryostatin compound has formula (XXIVb):

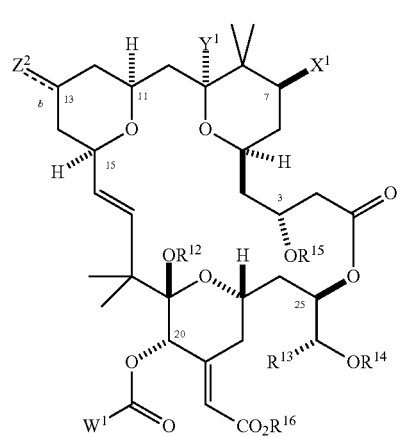

(XXIVb)

wherein:

$W^1$ is an alkenyl, a substituted alkenyl, an alkynyl, a substituted alkynyl, an alkyl or a substituted alkyl;

$Z^2$ is $=CR^5R^6$ or $=NR^7$ when the covalent bond designated "b" is a double bond; $Z^2$ is $-OR^8$ or $-N(R^7)_2$ when the covalent bond designated "b" is a single bond;

$X^1$ is H or $OR^{11}$;

$Y^1$ is H or $OR^{12}$;

$R^5$, $R^6$, $R^7$ and $R^8$ are each independently H, alkyloxycarbonyl (e.g., $-CO_2Me$), substituted alkyloxycarbonyl, alkyl or substituted alkyl;

$R^{11}$ is an acyl, a substituted acyl, an alkyl or a substituted alkyl;

$R^{12}$ is H, an alkyl or a substituted alkyl;

$R^{13}$ is an alkyl or a substituted alkyl;

$R^{14}$ and $R^{15}$ are independently H, or a promoiety; and $R^{16}$ is H, an alkyl or a substituted alkyl.

In some embodiments of formula (XXIVb), the bryostatin compound has formula (XXIIb):

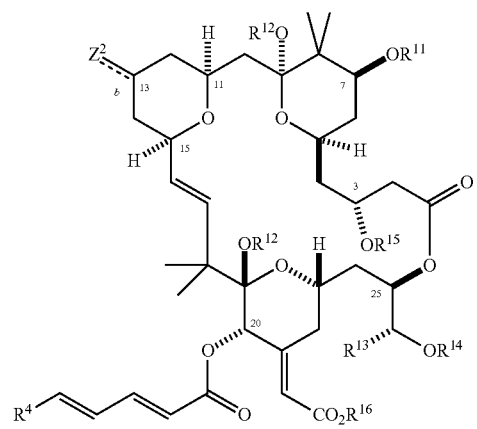

(XXIIb)

wherein:

$R^4$ is an alkyl or a substituted alkyl;

$Z^2$ is $=CR^5R^6$ or $=NR^7$ when the covalent bond designated "b" is a double bond;

$Z^2$ is $-OR^8$ or $-N(R^7)_2$ when the covalent bond designated "b" is a single bond;

$R^5$, $R^6$, $R^7$ and $R^8$ are each independently H, alkyloxycarbonyl (e.g., $-CO_2Me$), substituted alkyloxycarbonyl, alkyl or substituted alkyl;

$R^{11}$ is H, an acyl, a substituted acyl, an alkyl or a substituted alkyl;

$R^{12}$ is H, an alkyl or a substituted alkyl;

$R^{13}$ is H, an alkyl or a substituted alkyl;

$R^{14}$ and $R^{15}$ are independently H, or a promoiety; and $R^{16}$ is H, an alkyl or a substituted alkyl.

In some embodiments of formula (XXIIb), the bryostatin compound has formula (XXIIIb):

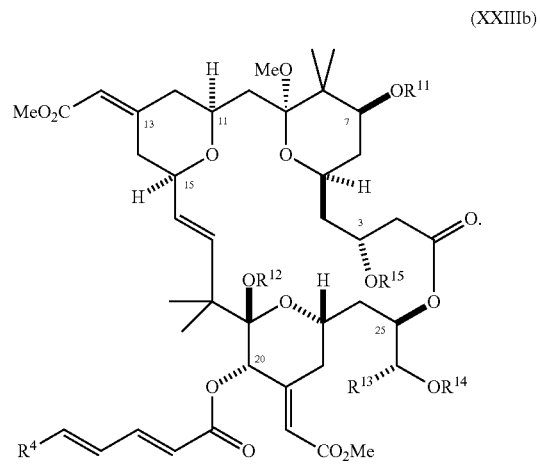

(XXIIIb)

In some instances of the formulae (XXIIb) and (XXIVb), $R^{16}$ is methyl. In some instances of the formulae (XXIIb), (XXIIIb) and (XXIVb), $R^{14}$ is H or a promoiety. In some instances of the formulae (XXIIb), (XXIIIb) and (XXIVb), $R^{13}$ is methyl. In some instances of the formulae (XXIIb) and (XXIVb), $R^{12}$ is methyl. In some instances of the formulae (XXIIb) and (XXIVb), $R^{12}$ is H. In some instances of the formulae (XXIIb), (XXIIIb) and (XXIVb), $R^{11}$ is acetyl. In some instances of the formulae (XXIIb), (XXIIIb) and (XXIVb), $R^{11}$ is H. In some instances of the formulae (XXIIb) and (XXIIIb), $R^4$ is $C_3H_7$. In some instances of the formulae (XXIIb), (XXIIIb) and (XXIVb), $R^{15}$ is H.

In some embodiments, the bryostatin compound is an analog of a naturally occurring bryostatin that has the formula (XXXI):

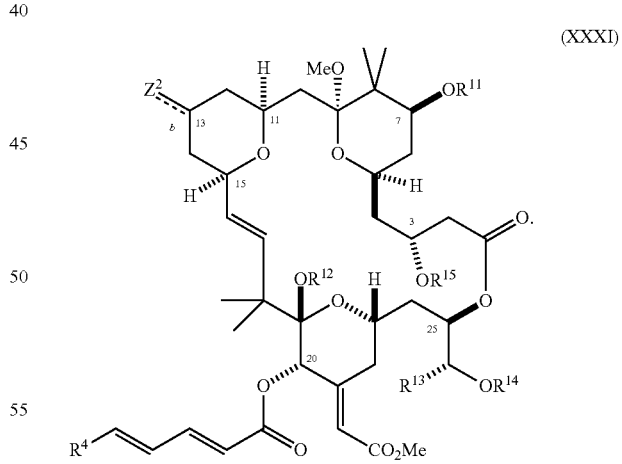

(XXXI)

wherein:

$R^4$ is an alkyl or a substituted alkyl;

$Z^2$ is $CR^5R^6$ or $NR^7$ when the covalent bond designated "b" is a double bond;

$Z^2$ is $OR^8$ or $N(R^7)_2$ when the covalent bond designated "b" is a single bond;

$R^5$, $R^6$, $R^7$ and $R^8$ are each independently H, halogen, alkyloxycarbonyl, substituted alkyloxycarbonyl, alkyl or substituted alkyl;

$R^{11}$ is an acyl, a substituted acyl, an alkyl or a substituted alkyl;

$R^{12}$ is H, an alkyl or a substituted alkyl;

$R^{13}$ is H, an alkyl or a substituted alkyl; and $R^{14}$ and $R^{15}$ are independently H, a hydroxyl protecting group or a promoiety;

or a solvate, hydrate or prodrug form thereof and/or a salt thereof.

In some instances of the formulae (XXXI), $R^4$ is propyl. In some instances of the formulae (XXXI), $R^{11}$ is an alkyl or a substituted alkyl. In some instances of the formulae (XXXI), $R^{11}$ is an acyl or a substituted acyl. In some instances of the formulae (XXXI), $R^{12}$ is an alkyl or a substituted alkyl.

In some instances of the formulae (XXXI), the covalent bond designated "b" is a double bond and $Z^2$ is $NR^7$ wherein $R^7$ is H, alkyloxycarbonyl, substituted alkyloxycarbonyl, alkyl or substituted alkyl. In certain cases, $Z^2$ is $CFCO_2R'$ where R' is alkyl (e.g., methyl). In some instances of the formulae (XXXI), the covalent bond designated "b" is a single bond and $Z^2$ is $OR^8$ or $N(R^7)_2$, wherein $R^7$ and $R^8$ are each independently H, alkyloxycarbonyl (e.g., $-CO_2Me$), substituted alkyloxycarbonyl, alkyl or substituted alkyl.

In some instances, $R^{13}$ is an alkyl comprising at least 2 carbons or a substituted alkyl. In some instances of the formulae (XXXI), $R^4$ is a substituted alkyl. In some instances of the formulae (XXXI), $R^{14}$ is a promoiety.

It is understood that any of the bryostatin analog compounds, and method of preparing the same, (e.g., as described herein) can be adapted to include an aliphatic (sp3-hybridized) carbon of the main chain (C1-C26) that is substituted with alkyl, substituted alkyl, alkoxy, substituted alkoxy, amino, substituted amino, azido or halogen (e.g., F, Cl) by means of a late-stage (e.g., near the end of the synthesis sequence of steps) C—H oxidation reaction. In some instances, the subject methods further include a late-stage C—H oxidation reaction to install a substituent of interest at one of the C1-C26 positions of the scaffold.

Figure 5:
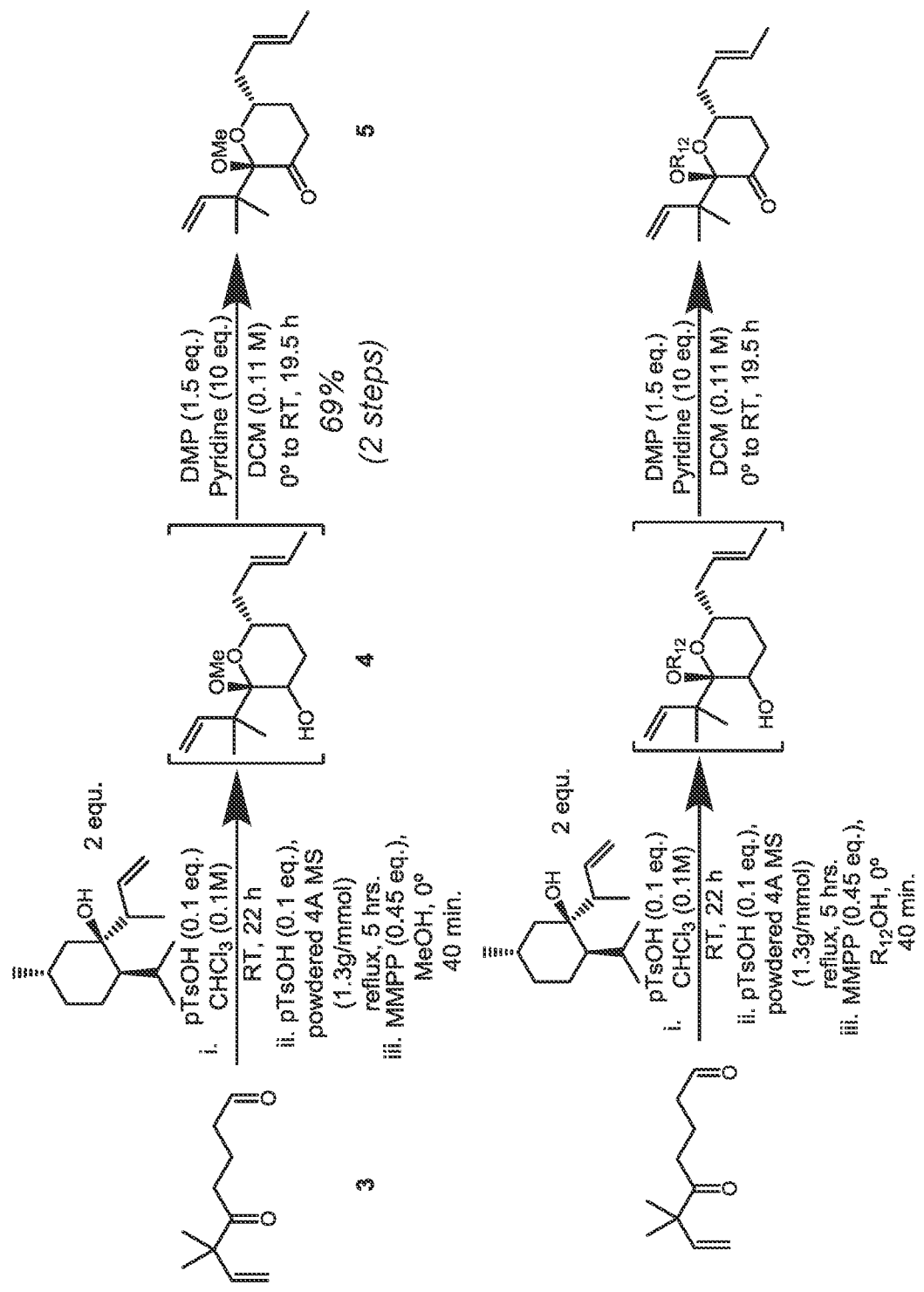
FIG. 5 illustrates an exemplary synthetic scheme for preparation of C19 ketal analogs of bryostatin compounds.

Bryostatin compounds of interest include, but are not limited to, those featuring variation of the C19 hemiketal (see e.g., FIG. 5). By altering the sequence of steps between compounds 3 and 5 (FIG. 5), any number of ketals can be installed, e.g., by changing the solvent used in the transformation from methanol to any convenient alcohol solvent.

Bryostatin compounds of interest include, but are not limited to, those featuring variation at the C13 position (see e.g., FIG. 6A and FIG. 6B). By altering the sequence of steps between compounds 6 and 7 or beginning with structure 6A (FIG. 6A and FIG. 6B), variability at the C13 position can be readily accomplished, e.g., through olefination or imine formation. In some cases, the C13 ketone can be reduced to the alcohol and subsequently acylated or etherified. In certain instances, the C13 ketone can be modified via a reductive amination with any convenient amino reactant. In some cases, the E isomer of the C13 enoate can be obtained. In certain instances, the C13 ketone is modified to form a spirocycle. In certain instances, the C13 ketone is modified to form a phosphate, a hetero group, or an organoselenium group.

In some embodiments, the bryostatin compound is an analog of a naturally occurring bryostatin that has the formula (XXXII):

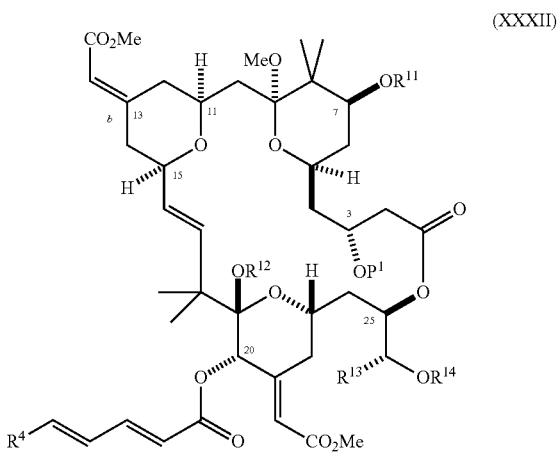

Variability at the C13 position can also be obtained by altering a C13 alkene of the structure 6B (FIG. 6C). In some cases the C13 alkene is substituted, e.g. with an alkyl or a halogen group. In some cases, the C13 alkene can be reduced and optionally further substituted e.g. with an alkyl, alkoxy, halogen group and the like. In some cases the alkene at the C13 position can be modified to form a carbocycle or a heterocycle, e.g. through an epoxidation reaction, cyclopropanation reaction, aziridine formation, thiirane formation, cycloadduct formation or spirocycle formation. In some instances, a carbocycle is formed with 3 carbons or more, such as 4 carbons or more, such as 5 carbons or more, such as 6 carbons or more, or even more. In some instances, a three membered heterocycle is formed. In some instances a larger heterocycle is formed, such as a four membered heterocycle, a five membered heterocycle, a six membered heterocycle, or an even larger heterocycle.

With reference to FIG. 6A, FIG. 6B and FIG. 6C, group "X" includes, but is not limited to the following groups and atoms: an alkyl, a substituted alkyl, a halide, a carbon atom, a heteroatom (e.g. O, N, S and the like), heteroalkyl group e.g. an amine, an alkoxy, or a thio, an organoselenium, a phosphate etc. The group "Y" includes, but is not limited to the following groups and atoms: an amine, an alkoxy, a halide, a carbon atom, a heteroatom (e.g. O, N, S and the like). The group R' includes, but is not limited to the following groups: alkyl, substituted alkyl, phosphates, heterogroups etc. The group R" includes, but is not limited to the following groups: alkyl, substituted alkyl, aryl, substituted aryl, acyl, substituted acyl, halide, hydroxyl, alkoxy. The term "n" will be understood as an integer e.g. 1, 2, 3, 4 etc.

In some embodiments, the bryostatin compound is an analog of a naturally occurring bryostatin that has the formula (XXXIII):

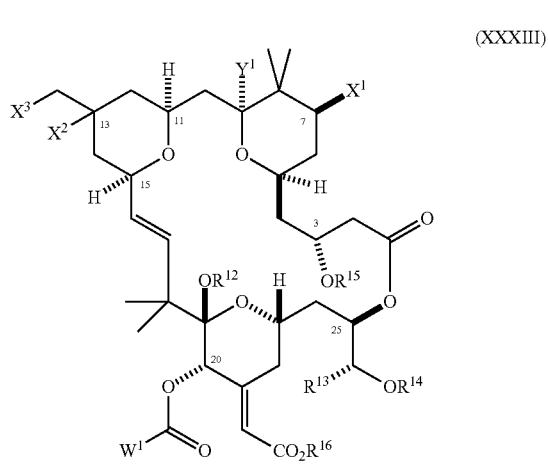

(XXXIII)

wherein:
- $W^1$ is an alkenyl, a substituted alkenyl, an alkynyl, a substituted alkynyl, an allenyl, a substituted allenyl, an alkyl, a substituted alkyl, an aryl, a substituted aryl, a heteroaryl, a substituted heteroaryl, heteroalkyl, substituted heteroalkyl, heterocycle, substituted heterocycle, or a carbon chain containing oxygen or nitrogen atoms, and/or rings and substituted rings included cycloalkyl, cycloalkenyl and the like (e.g., a PEG or modified PEG group);
- $X^1$ is H or $OR^{11}$;
- $X^2$ and $X^3$ are independently selected from H, halogen, alkyl, substituted alkyl, alkoxy, amine, substituted amine, amide, substituted amide, acyl, hydroxyl, heteroalkyl, heteroaryl, substituted heteroaryl, phosphate, organoselenium, thio, substituted thio, or $X^2$ and $X^3$ combine to form a carbocyclic ring or a heterocyclic ring e.g. a cyclopropane, an epoxide, an aziridine, a thiirane, a 4-membered spirocycle, a 5-membered spirocycle or a 6 membered spirocycle;
- $Y^1$ is H or $OR^{12}$;
- $R^{12}$ is H, an alkyl or a substituted alkyl;
- $R^{13}$ is H, an alkyl or a substituted alkyl;
- $R^{16}$ is H, an alkyl or a substituted alkyl; and
- $R^{14}$ and $R^{15}$ are independently H, a hydroxyl protecting group or a promoiety; or a solvate, hydrate or prodrug form thereof and/or a salt thereof.

Bryostatin compounds of interest include, but are not limited to, those featuring variation at the C12 or C14 position, or both the C12 and C14 positions. Variability in the B ring can be obtained by altering the C12 or the C14 carbon, or both the C12 and the C14 carbon in any of the structures 6, 6A or 6B (FIG. 6A, FIG. 6B and FIG. 6C). In some cases the C12 carbon is alkylated. In some cases, the C14 carbon is alkylated. In some cases the C12 carbon is substituted with a halogen. In some cases the C14 carbon is substituted with a halogen. In some cases the C12 or C14 position are independently substituted with a group selected from the group consisting of substituted alkyl, alkoxy, amine, substituted amine, amide, substituted amide, acyl, hydroxyl, heteroalkyl, heteroaryl, substituted heteroaryl, substituted heteroaryl, phosphate, phosphoryl, sulfate, sulfonyl, organoselenium, thio, substituted thio.

In some embodiments, the bryostatin compound is an analog of a naturally occurring bryostatin that has the formula (XXXIV):

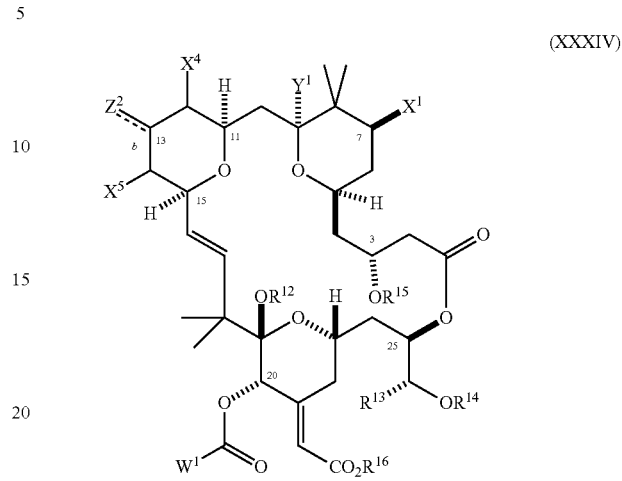

(XXXIV)

wherein:
- $W^1$ is an alkenyl, a substituted alkenyl, an alkynyl, a substituted alkynyl, an allenyl, a substituted allenyl, an alkyl, a substituted alkyl, an aryl, a substituted aryl, a heteroaryl, a substituted heteroaryl, heteroalkyl, substituted heteroalkyl, heterocycle, substituted heterocycle, or a carbon chain containing oxygen or nitrogen atoms, and/or rings and substituted rings included cycloalkyl, cycloalkenyl and the like (e.g., a PEG or modified PEG group);
- $Z^2$ is $CR^5R^6$ or $NR^7$ when the covalent bond designated "b" is a double bond;
- $Z^2$ is $OR^8$, a phosphate, a phosphoryl, a thio group, a sulfate, a sulfonyl, an organoselenium group, or $N(R^7)_2$ when the covalent bond designated "b" is a single bond;
- $R^5$, $R^6$, $R^7$ and $R^8$ are each independently H, halogen, alkyloxycarbonyl, substituted alkyloxycarbonyl, alkyl or substituted alkyl;
- $X^1$ is H or $OR^{11}$;
- $X^4$ and $X^5$ are independently selected from H, halogen, alkyl, substituted alkyl, alkoxy, amine, substituted amine, amide, substituted amide, acyl, hydroxyl, heteroalkyl, heteroaryl, substituted heteroalkyl, substituted heteroaryl, phosphate, organoselenium, thio, substituted thio;
- $Y^1$ is H or $OR^{12}$;
- $R^{12}$ is H, an alkyl or a substituted alkyl;
- $R^{13}$ is H, an alkyl or a substituted alkyl; and
- $R^{16}$ is H, an alkyl or a substituted alkyl,
- $R^{14}$ and $R^{15}$ are independently H, a hydroxyl protecting group or a promoiety;

or a solvate, hydrate or prodrug form thereof and/or a salt thereof.

Figure 7:
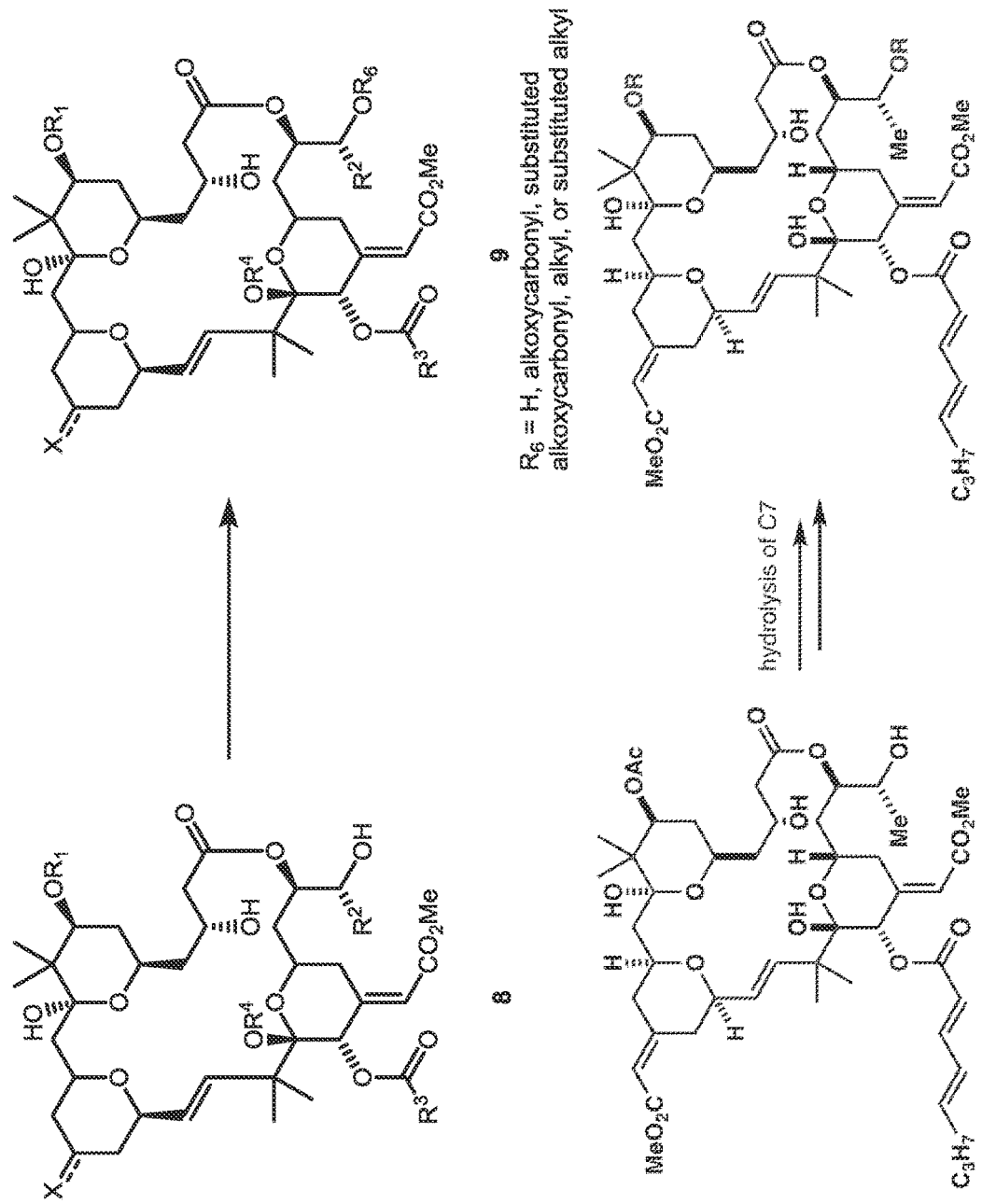
FIG. 7 illustrates an exemplary synthetic scheme for preparation of C26 ester analogs of bryostatin compounds, including prodrug compounds.
Figure 8:
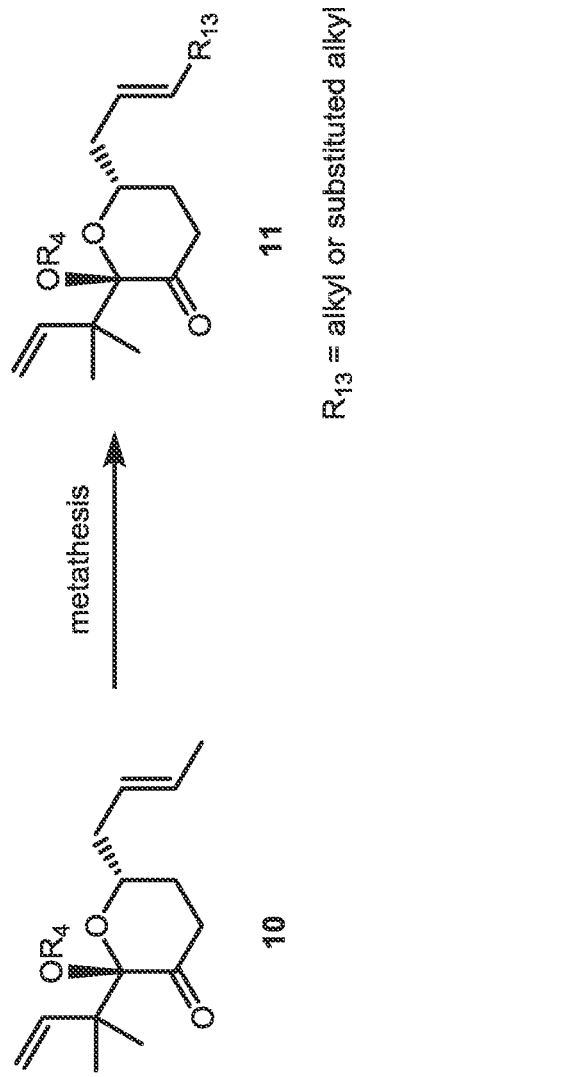
FIG. 8 illustrates an exemplary synthetic scheme for preparation of C26 alkyl analogs of bryostatin compounds.

Bryostatin compounds of interest include, but are not limited to, those featuring variation at the C26 position (see e.g., FIGS. 7 and 8). By altering the subject methods disclosed for synthesis of the southern hemisphere fragment, variation at the C26 alcohol can be introduced. In some instances of the subject bryostatin compounds, a hydroxy group at the C26 position is necessary for compound activity. In some cases, variation at the C26 position provides for a prodrug from of a bryostatin compound of interest, where the prodrug form is capable of conversion in vivo to a free C26 hydroxyl group.

In some embodiments, the subject compounds are provided in a prodrug form. "Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)).

Prodrugs of bryostatin compounds include particular bryostatin analogs at C26 (see e.g., FIG. 7, compounds 8 and 9). The subject methods of synthesis of the Southern Hemisphere fragment can provide for derivatization of the C26-alcohol, e.g., with an ester. In some instances, introduction of an ester group at the C26 position can inactivate the resulting bryostatin derivative. In certain embodiments, the C26 ester group can be cleaved, e.g., either chemically (e.g., at a particular pH, via photochemical means) or biologically (e.g. via action of an endogenous esterase) to release a bryostatin compound having a free C26 hydroxyl group. This prodrug strategy can provide for facile alteration of a bryostatin compound of interest to improve its pharmacological properties, such as PK (pharmacokinetics) and ADME (absorption, distribution, metabolism, and excretion) properties, while maintaining the activity of bryostatin, which is gradually released as the free drug after compound administration.

The cleavable linkage may include a group that can be hydrolytically, enzymatically, or otherwise cleaved in vivo. The inactive group can range from an alkyl group (e.g., selected to provide a particular cleavage rate) to an oligopeptide or lipid (e.g., to enhance cellular uptake). Modifications can include but are not limited to esters, carbonates, carbamates, and ethers all of which can contain alkyl groups, alkenyl groups, alkynyl groups, amines, hydroxyl groups, guanidinium groups, carbocycles, and heterocycles.

In some embodiments Bryostatin 1 is modified to form a structure of formula (XXXV):

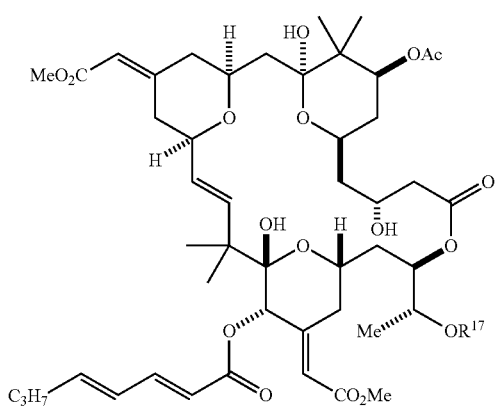

(XXXV)

Wherein $R^{17}$ is selected from an ester, a carbonate, a carbamate and an ether, all of which can be optionally substituted with one or more groups selected from, an alkyl, an alkenyl, an alkynyl, an amine, a hydroxyl, a disulfide, a guanidinium, a carbocycle, and a heterocycle. In some instances, the acetate group at C7 is replaced with a H atom, an ester, a carbonate, a carbamate or an ether, all of which can be optionally substituted with one or more groups selected from, an alkyl, an alkenyl, an alkynyl, an amine, a hydroxyl, a disulfide, a guanidinium, a carbocycle, and a heterocycle (e.g. see FIG. 7, where "R" as depicted in FIG. 7 is as defined herein for $R^{17}$).

Bryostatin compounds of interest include, but are not limited to, those featuring variation at the C26 methyl position. The subject methods of preparing the southern hemisphere fragment can be adapted to prepare analogs that possess any convenient C26 substituents at the C26 methyl position. FIG. 8 illustrates an exemplary strategy for introducing a variety of $R_2$ groups at the C26 methyl position via a metathesis reaction converting intermediate 10 to 11. Any convenient cross metathesis procedures can be adapted for use in the subject methods to introduce an $R_2$ group at the C26 methyl position of a synthetic intermediate of interest (e.g., intermediate 10, FIG. 8).

Figure 9:
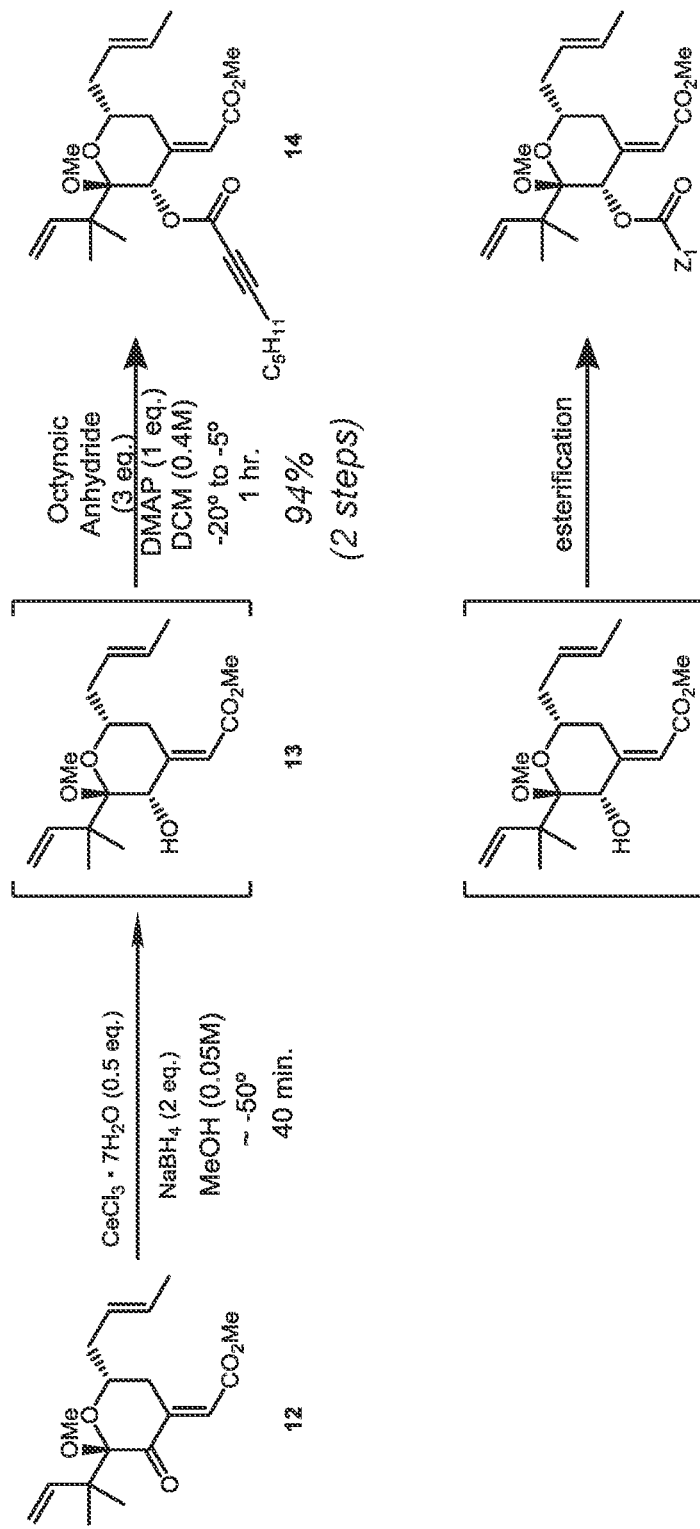
FIG. 9 illustrates an exemplary synthetic scheme for preparation of C20 ester analogs of bryostatin compounds.

Bryostatin compounds of interest include, but are not limited to, those featuring variation at the C20 ester position. Any convenient ester groups can be installed on the C20 hydroxyl group (e.g., as described herein). FIG. 9 illustrates an exemplary synthetic strategy. In some instances, the ester group is a alkyne containing precursor of an octadienoate group, such as the octadienoate present at the C20 ester position of bryostatin 1. By altering the southern hemisphere sequence from 12 to 14, analogs can be prepared through esterification of 13 with a wide variety of ester groups (FIG. 9). It is understood that in some cases, any of the ester groups described herein can be referred to as a corresponding acyl or substituted acyl substituent of the C20 hydroxyl. In some cases, the ester group is an alkyl or a substituted alkyl ester. In some cases, the ester group is an aryl or a substituted aryl ester. In some cases, the ester group is an alkenyl or a substituted alkenyl. In some cases, the ester group is an alkynyl or a substituted alkynyl ester.

Bryostatin compounds of interest include, but are not limited to, those featuring variation at the C21 enoate ester position. Any convenient ester groups can be installed on the C20 hydroxyl group (e.g., as described herein). For example, in FIG. 2 step 5, a variety of reactants could be used instead of methyl glyoxylate to install a variety of groups at the C21 position. Any convenient glyoxylate esters can be used in the subject methods, including but not limited to, a glyoxylate alkyl ester, such as ethyl glyoxylate.

Aspects of the present disclosure include bryostatin compounds, salts thereof (e.g., pharmaceutically acceptable salts), and/or solvate, hydrate and/or prodrug forms thereof. In addition, it is understood that, in any compound described herein having one or more chiral centers, if an absolute stereochemistry is not expressly indicated, then each center may independently be of R-configuration or S-configuration or a mixture thereof. It will be appreciated that all permutations of salts, solvates, hydrates, prodrugs and stereoisomers are meant to be encompassed by the present disclosure.

In some embodiments, the subject bryostatin compounds, or a prodrug form thereof, are provided in the form of pharmaceutically acceptable salts. Compounds containing an amine, imine or nitrogen containing group may be basic in nature and accordingly may react with any number of inorganic and organic acids to form pharmaceutically acceptable acid addition salts.

In some embodiments, the subject compounds, prodrugs, stereoisomers or salts thereof are provided in the form of a solvate (e.g., a hydrate). The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

Utility

The bryostatin compounds as described herein and methods of preparing the same may find use in a variety of applications, including therapeutic, diagnostic and research applications, in which the modulation of a C1 domain containing protein of interest is desirable.

Bryostatin 1 finds use in the treatment of diseases for which there are no effective therapies, including the eradication of HIV/AIDS and Alzheimer's disease. A 150 patient Phase 2B clinical trial for the treatment of Alzheimer's disease with Bryostatin 1 was recently completed. The subject methods of total synthesis provide a sustainable, scalable, reproducible, and economical way to replenish the world supply of bryostatin for continued clinical use.

Specifically, applications of interest, but not limited to:

1) Supplying bryostatin as a first-in-class small molecule therapeutic for the eradication of HIV/AIDS. Over 37 million men, women, and children are infected with HIV and must take daily medication for life to stop progression of the disease. Eradication would have a transformative impact on their lives, allowing them to avoid the cost and health problems associated with chronic chemotherapy. Moreover, because most infected individuals and especially those in emerging countries do not have reliable access to medications or are noncompliant, eradication becomes the major strategy to addressing this global problem. Bryostatin has been shown to flush out latent HIV from infected cells, both as a single agent and in combination with other latency reversing agents. The latent nature of the virus is the reason why patients require lifelong treatment with all known current therapies, which only target the active virus. Bryostatin is the lead compound in targeting the genomically encoded latent virus, the root cause of chronic infection. Thus, bryostatin could eliminate the latent virus due to its novel mode of action. This, in combination with current highly active anti-retroviral therapy (HAART), is one of the most promising strategies for the eradication of HIV. Due to this activity, bryostatin was recently in a Phase I clinical trial for HIV latency reversal treatment.

2) Supplying bryostatin as a first-in-class small molecule therapeutic for the treatment of Alzheimer's disease (AD), currently the third leading cause of death in the United States when under-reporting is considered. Bryostatin's unique activity involves induction of synaptogenesis in the brain, as well as reduction in amyloid plaques and tau tangles associated with AD. Mouse models indicate that these actions significantly enhance learning and memory, restoring normal function in animal models of disease. These pre-clinical results were sufficiently compelling to lead to entry of bryostatin in an Alzheimer's clinical trial, followed by a Phase 2B clinical trial for the treatment of AD.

3) Supplying bryostatin as a first-in-class small molecule for cancer immunotherapy, a rapidly developing and transformative approach toward long-lasting, cancer-specific cures. Specifically, bryostatin makes cancer cells more immunogenic, thereby enhancing the ability of immune cells to recognize and kill cancer cells. This holds the potential for a transformative approach toward cancer treatment in which a small non-toxic molecule converts cancer cells into cells that could be eliminated by the specificity, selectivity, and power of one's own immune system. Cancer is the leading cause of death in developed countries and a rapidly rising problem in others. Cancer immunotherapy is one of the most promising approaches to addressing this global problem. PKC modulators offer the potential to enhance immunotherapy efficacy by making cancer cells more immunogenic through induction of antigen expression and externalization. As a result, these cancer cells become more susceptible to clearance by our native immune system or monoclonal antibodies. Small molecule enhanced immunotherapy can be a non-toxic way to clear cancer cells. PKC modulators exhibit immunostimulatory activity in human cancer cell lines and ex vivo in cells from patients. Molecules like bryostatin that convert cancer cells into immune stimulator cells can improve immunotherapies and even use our native immune system, often degraded by cytotoxic therapy, for cancer cell clearance. The present studies on this clinical opportunity complement our HIV eradication studies as both involve induction of CD69.

4) Supplying bryostatin as a first-in-class small molecule therapeutic for neurodegenerative orphan diseases including but not limited to Niemann-Pick disease, Fragile X disease and Charcot-Marie Tooth syndrome.

5) Stroke is the leading cause of long-term disability in the U.S. The only acute therapies are thrombolytics (i.e. tissue plasminogen activator) but these treatments are limited to <4.5 h from the onset of symptoms; after that window of time, thrombolytics actually worsen survival outcomes. In mouse models of stroke, bryostatin extends that window of opportunity to up to 24 h after an ischemic event; specifically, bryostatin improved survival, reduced infarct volume and atrophy, and improved neurological function 21 days after stroke. Again, a sustainable supply of bryostatin is critical to continue research of this important but unmet medical need.

6) Supplying bryostatin as a therapeutic for any indication where its binding protein, a C1 domain-containing target protein (e.g., as described herein), such as PKC, is implicated. Because bryostatin is among the most potent and biologically active PKC modulators, either as an activator or an inhibitor, it is a lead compound for such indications. For example, PKC pathways are implicated in the orphan disease Charcot-Marie-Tooth. For example, C1 domain-containing target proteins are implicated in a variety of signaling processes of interest, e.g., diacylglycerol (DAG) signaling pathways. For example, C1 domain-containing target proteins are implicated in the chikingunya virus.

7) Providing the most time and cost-effective synthesis of bryostatin analogs. While the natural product is of therapeutic interest, a variety of bryostatin analogs can recapitulate and even improve upon the biological activity of bryostatin. A variety of analogs display improved toxicity profiles, PKC isoform selectivity, and more positive readouts in HIV latency reversal studies (including but not limited to humanized mice models and ex vivo samples taken from HIV-positive patients). Due to the structural similarity of such analogs with bryostatin 1, the subject methods provide a platform for the rapid and scalable synthesis of analogs. In some cases, the subject bryostatin compounds exhibit selectivity for a particular PKC isoform. In certain cases, the selectivity is for a conventional PKC isoform. In certain cases, the selectivity is for a novel PKC isoform. In certain cases, the selectivity is for an alpha PKC isoform. In certain cases, the selectivity is for a beta I PKC isoform. In certain cases, the selectivity is for a beta II PKC isoform. In certain cases, the selectivity is for a gamma PKC isoform. In some embodiments, structural features that can influence the PKC isoform selectivity of the subject compounds include but are not limited to, features in the northern hemisphere of the bryostatin analogs (e.g. corresponding to the region inhabited from C-1 to C-17 in bryostatin 1), and the presence or absence of the C-26 methyl group. These features are consistent with the pharmacophore model (e.g., as described herein) wherein variations in functionality at C1, C19 and C26 influence PKC binding affinity as well as selective affinity to different PKC isoforms of interest. In some cases, while the southern fragment region of the compound is proposed to contact PKC, the northern fragment serves to conformationally control the binding elements in the southern fragment while at the same time influencing the depth and orientation of the PKC-ligand complex in the cell membrane.

The terms "specific binding" or "selective binding" refers to the ability of a compound to preferentially bind to a particular target protein (e.g., PKC isoform) that is present in a homogeneous mixture of different non-target proteins. In general terms, a specific binding interaction will discriminate between target and non-target proteins in a sample, typically more than about 10 to 100-fold or more (e.g., more than about 1000-fold). Typically, the affinity between a capture agent and analyte when they are specifically bound in a capture agent/analyte complex is at least $10^{-8}$ M, at least $10^{-9}$ M, in some cases at least $10^{-10}$ M.

8) Bryostatin and its analogs are sought-after research tools for life science research. They are exceptionally expensive and available only in microgram quantities from conventional sources. The subject methods provide these compounds as research tools available in quantity and at greatly reduced cost.

Methods of Use

Also provided are methods of treatment using the subject bryostatin compounds and pharmaceutical preparations. Hosts, including mammals and particularly humans, suffering from any of the disorders described herein, including abnormal cell proliferation and other disorders in which a C1 domain containing protein is implicated, such as PKC related disorders, can be treated by administering to the host an effective amount of a bryostatin compound as described herein, or a pharmaceutically acceptable prodrug, ester, solvate, hydrate and/or salt thereof, optionally in the presence of a pharmaceutically acceptable carrier or diluent. The active materials can be administered by any appropriate route, for example, orally, parenterally, intramuscularly, intravenously, intradermally, subcutaneously, transdermally, bronchially, pharyngolaryngeally, intranasally, topically, rectally, intracisternally, intravaginally, intraperitoneally, bucally, intrathecally, or as an oral or nasal spray.

The active compound is included in the pharmaceutically acceptable carrier or diluent in an amount sufficient to deliver to the host a therapeutically effective amount of compound to treat, for example, abnormal cell proliferation in vivo, without causing serious toxic effects in the host treated. It is to be understood that for any particular subject, specific dosage regimens can be adjusted over time according to the individual need and the professional judgment of the person administering or supervising the administration of the compositions. The active ingredient may be administered at once, or may be divided into a number of smaller doses to be administered at varying intervals of time.

A pharmaceutically acceptable prodrug or salt thereof, as used herein, represents those prodrugs of the compounds of the present disclosure which are, within the scope of sound medical judgment, suitable for use in contact with the tissues of hosts, such as humans and mammals without undue toxicity, irritation, allergic response, and the like, commensurate with a reasonable benefit/risk ratio, and effective for their intended use. Prodrugs of the present disclosure may be rapidly transformed in vivo to an active parent compound, for example, by hydrolysis in blood.

Bryostatin compounds of interest are thought to act by modulating the activity and cellular localization of various C1 domain-containing proteins such as protein kinase C (PKC). The PKC family is divided into three subclasses: the conventional ($\alpha$, $\beta$I, $\beta$II, $\gamma$), novel ($\delta$, $\epsilon$, $\eta$, $\theta$), and atypical isozymes. The subclasses are categorized on the basis of the factors needed for their activation. Members of the conventional family (cPKCs), consisting of PKC$\alpha$, PKC$\beta$I, PKC$\beta$II, and PKC$\gamma$, are activated by the combination of calcium and diacylglycerol (DAG). The novel family (nPKCs), consisting of PKC$\delta$, PKC$\epsilon$, PKC$\theta$, and PKC$\theta$, does not require calcium for activation but does respond to DAG. Members of the atypical family (aPKCs) do not respond to either calcium or DAG. Of these three, bryostatin compounds of interest can bind to the C1 domains of conventional and novel subclasses (eight isozymes in total).

The conventional and novel PKCs incorporate both a regulatory domain and a catalytic domain. The regulatory domain is responsible for controlling the activity-state of the kinase. The catalytic domain contains the ATP and substrate binding sites and catalyzes the transfer of phosphate groups. When PKC is inactive, it exists in a closed conformation in which a pseudosubstrate sequence occupies the substrate-binding site preventing access by downstream targets. Additionally, the inactive form of PKC is localized to a different cellular compartment than the active form of the enzyme, keeping it spatially removed from its relevant target proteins. Bryostatin compounds are believed to activate PKC by binding to one of the C1 domains of the protein. This binding can result in translocation of PKC from the cytosol to cellular membranes and exposure of the substrate-binding site of the protein. Membrane association and translocation are further influenced by interaction of the active kinase with isoform-specific receptor proteins (RACKs). In contrast to molecules that target the ATP binding site of PKC and function only as inhibitors, molecules that target the C1 domain can be designed to inhibit or activate enzyme activity. In some cases, bryostatin compounds can selectively regulate one or a subset of these eight isozymes and provide select modulatory activity, offering a greater range of efficacy in therapeutic interventions of many types, and greater selectivity in function, since C1 domains are not present in every member of the kinase family.

Protein kinase C mediates one arm of the signal transduction pathway proceeding through inositol phospholipid breakdown. This pathway is involved in the action of a broad range of cellular effectors, including growth factors and oncogenes, and indirectly affects other transduction pathways such as that of the cyclic AMP second messenger system. Therefore, modulating PKC activity using the subject bryostatin compounds can provide approaches for pharmaceutical intervention in many therapeutic areas. PKC$\delta$ is a critical player in various apoptotic pathways and can influence the metastatic potential of cancer cells, and PKC$\epsilon$ has also been shown to be involved in cancer development.

PKCβ1 is also an essential participant in the apoptotic pathway. Analogs are disclosed herein which can modulate specific classes of PKC isozymes selectively.

In one aspect, the compounds of the present disclosure find use as anticancer agents in mammalian subjects. For example, representative cancer conditions and cell types against which the compounds of the present disclosure may be useful include melanoma, myeloma, chronic lymphocytic leukemia (CLL), AIDS-related lymphoma, non-Hodgkin's lymphoma, colorectal cancer, renal cancer, prostate cancer, cancers of the head, neck, stomach, esophagus, anus, or cervix, ovarian cancer, breast cancer, peritoneal cancer, and non-small cell lung cancer. The subject bryostatin compounds appear to operate by a mechanism distinct from the mechanisms of other anticancer compounds, and thus can be used synergistically in combination with other anticancer drugs and therapies to treat cancers via a multimechanistic approach.

In some aspects, the compounds of the present disclosure can be used to strengthen the immune system of a mammalian subject, wherein a compound of the present disclosure is administered to the subject in an amount effective to increase one or more components of the immune system for which modulation of PKC pathways is required, by inhibition or activation. For example, strengthening of the immune system can be evidenced by increased levels of T cells, antibody-producing cells, tumor necrosis factors, interleukins, interferons, and the like. Effective dosages may be comparable to those for anticancer uses, and can be optimized with the aid of various immune response assay protocols (e.g., see U.S. Pat. No. 5,358,711). The subject compounds can be administered prophylactically, e.g., for subjects who are about to undergo anticancer therapies, as well as therapeutically, e.g., for subjects suffering from microbial infection, burn victims, subjects with neuroendocrine disorders, diabetes, anemia, radiation treatment, or anticancer chemotherapy. The immunostimulatory activity of the compounds of the present disclosure is unusual among anticancer compounds and provides a dual benefit for anticancer applications. First, the immunostimulatory activity allows the compounds of the present disclosure to be used in greater doses and for longer periods of time than would be possible for compounds of similar anticancer activity but lacking immunostimulatory activity. Second, the compounds of the present disclosure can offset the immunosuppressive effects of other drugs or treatment regimens when used in combination therapies.

In some embodiments, the disorders of abnormal cell proliferation are tumors and cancers, psoriasis, autoimmune disorders, disorders brought about by abnormal proliferation of mesangial cells (including human renal diseases, such as glomerulonephritis, diabetic nephropathy, malignant nephrosclerosis, thrombotic micro-angiopathy syndromes, transplant rejection, and glomerulopathies), rheumatoid arthritis, Behcet's syndrome, acute respiratory distress syndrome (ARDS), ischemic heart disease, post-dialysis syndrome, leukemia, vasculitis, restenosis, neuropathic pain, chronic hypoxic pulmonary hypertension, lipid histiocytosis, acute and chronic nephropathies, atheroma, arterial restenosis, autoimmune diseases, or ocular diseases with retinal vessel proliferation (for example, diabetic retinopathy).

Other areas of application for which the compounds of the present disclosure can be useful include disorders of associative memory storage. PKC signaling pathways have been observed to regulate points in the neurodegenerative pathophysiology of Alzheimer's disease (AD). Bryostatin-1 has been studied preclinically and has demonstrated to have cognitive restorative and antidepressant effects. This may be due to reduction of neurotoxic amyloid production and accumulation, activation of select PKC isoforms, induction of synthesis of proteins involved in long term memory, and restoration of stress induced inhibition of PKC activity. The compounds of the present disclosure may have more selective activities in modulating specific PKC isoforms involved and decreased toxicity relative to the natural product, and a lack of tumor promoting ability (unlike other classes of PKC modulator compounds) thus providing utility as therapeutics to treat AD, depression and other cognitive and memory disorders.

The compounds of the present disclosure may be useful in antiviral and antiproliferative therapies by activating PKC to render a diseased cell susceptible to killing by a second therapeutic agent, for example, ganclicovir and/or radiation, in the case of Epstein Barr Virus associated nasopharyngeal carcinoma (NPC). This can also be a fruitful approach for combination therapies for other viral infections such as HIV and HSV.

Combination Therapy

Bryostatin compounds of the present disclosure can be used in combination with other chemotherapeutic agents to treat cancer. In some embodiments, the combination may provide a synergistic therapeutic effect. The synergy is believed to arise from the effect of using two therapeutic agents which act through different mechanistic pathways. For example, Taxol and a bryostatin analog compound, when administered together, either in the same composition or separately, to a subject, may prevent neoplastic cells from mounting resistance as readily as is possible using only a single agent acting through a single mechanistic pathway or binding only at one site on the neoplastic cells. Synergy may be then provided in interactions between the compounds of the present invention and Taxol, for example, or with chemotherapeutic agents of other classes used to treat cancer and other proliferative and immune related disorders.

Compounds of the present disclosure can be used in combination or alternation with radiation and chemotherapy treatment, including induction chemotherapy, primary (neoadjuvant) chemotherapy, and both adjuvant radiation therapy and adjuvant chemotherapy. In addition, radiation and chemotherapy are frequently indicated as adjuvants to surgery in the treatment of cancer. The goal of radiation and chemotherapy in the adjuvant setting is to reduce the risk of recurrence and enhance disease-free survival when the primary tumor has been controlled. Chemotherapy is utilized as a treatment adjuvant for lung and breast cancer, frequently when the disease is metastatic. Adjuvant radiation therapy is indicated in several diseases including lung and breast cancers. Compounds of the present disclosure also are useful following surgery in the treatment of cancer in combination with radio- and/or chemotherapy. Compounds of the present disclosure may be administered before, concomitantly, in the same composition, or after administering one or more additional active agents.

Active agents that can be used in combination with a protein kinase C modulator of the present disclosure include, but are not limited to, alkylating agents, antimetabolites, hormones and antagonists, protein kinase C modulators of other classes, microtubule stabilizers, radioisotopes, antibodies, as well as natural products, and combinations thereof. For example, a compound of the present disclosure can be administered with antibiotics, such as doxorubicin and other anthracycline analogs, nitrogen mustards, such as cyclophosphamide, pyrimidine analogs such as 5-fluorouracil, cisplatin, hydroxyurea, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH) Other antineoplastic protocols include the use of a compound of the present disclosure with another treatment modality, e.g., surgery or radiation, also referred to herein as "adjunct anti-neoplastic modalities."

More specific examples of active agents useful for combination with compounds of the present disclosure, in both compositions and the methods of the present disclosure, include but are not limited to, alkylating agents, such as nitrogen mustards (e.g., mechlorethanmine, cyclophosphamide, ifosfamide, melphalan, and chlorambucil); nitrosureas, alkyl sulfonates, such as busulfan; triazines, such as dacarbazine (DTIC); antimetabolites; folic acid analogs, such as methotrexate and trimetrexate; pyrimidine analogs, such as 5-fluorouracil, fluorodeoxyuridine, gemcitabin, cytosine arabinoside (AraC, cytarabine), 5-azacytidine, and 2,2'-difluorodeoxycytidine; purine analogs, such as 6-mercaptopurine, 6-thioguanine, azathioprine, 2'-deoxycoformycin (pentostatin), erythrohydroxynonyladenine (EHNA), fludarabine phosphate, and 2 chlorodeoxy-adenosine (cladribine, 2-CdA); natural products, including antimitotic drugs such as paclitaxel (Taxol®), vinca alkaloids (e.g., vinblastine (VLB), vincristine, and vinorelbine), Taxotere® (docetaxel), camptothecin, estramustine, estramustine phosphate, colchicine, bryostatin, combretastatin (e.g., combretastatin A-4 phosphate, combretastatin A-1 and combretastatin A-3, and their phosphates), dolastatins 10-15, podophyllotoxin, and epipodophylotoxins (e.g., etoposide and teniposide); antibiotics, such as actimomycin D, daunomycin (rubidomycin), doxorubicin (adriamycin), mitoxantrone, idarubicin, bleomycins, plicamycin (mithramycin), mitomycinC, dactinomycin, and tobramycin; enzymes, such as L-asparaginase; antibodies, such as HERCEPTIN® (Trastruzumab), RITUXAN® (Rituximab), PANOREX® (edrecolomab), ZEVALIN® (ibritumomab yiuxetan), MYLOTARGT® (gemtuzumab ozogamicin), and CAMPATH® (alemtuzumab); biological response modifiers, such as interferon-alpha, IL-2, G-CSF, and GM-CSF; differentiation agents; retinoic acid derivatives; radiosensitizers, such as metronidazole, misonidazole, desmethylmisonidazole, pimonidazole, etanidazole, nimorazole, RSU 1069, E09, RB 6145, SR4233, nicotinamide, 5-bromodeozyuridine, 5-iododeoxyuridine, and bromodeoxycytidine; platinum coordination complexes such as cisplatin and carboplatin; anthracenedione; mitoxantrone; substituted ureas, such as hydroxyurea; methylhydrazine derivatives, such as N-methylhydrazine (MIH) and procarbazine; adrenalcortical suppressants, such as mitotane (o,p'-DDD), aminoglutethimide; cytokines, such as interferon alpha, beta, and gamma and Interleukin 2 (IL-2); hormones and hormone antagonists, including adreno-corticosteroids/antagonists such as prednisone and its equivalents, dexamethasone, and aminoglutethimide; progestins, such as hydroxyprogesterone, caproate, medroxyprogesterone acetate, and megesterol acetate; estrogens, such as diethylstilbestrol, ethynyl estradiol, and their equivalents; antiestrogens, such as tamoxifen; androgens, such as testosterone propionate and fluoxymesterone, as well as their equivalents; antiandrogens, such as flutamide; gonadotropin-releasing hormone analogs, such as leuprolide; nonsteroidal antiandrogens, such as flutamide, and photosensitizers, such as hematoporphyrin and its derivatives, Photofrin®, benzoporphyrin and its derivatives, Npe6, tin etioporphyrin (SnET2), pheoboride-α, bacteriochlorophyll-α, naphthalocyanines, phthalocyanines, and zinc phthalocyanines.

In certain embodiments, the compounds of the present disclosure are administered in combination or alternation with a second agent selected from the group such as vincristine, cisplatin, ara-C, taxanes, edatrexate, L-buthionine sulfoxide, tiazofurin, gallium nitrate, doxorubicin, etoposide, podophyllotoxins, cyclophosphamide, camptothecins, dolastatin, and auristatin-PE, for example, and may also be used in combination with radiation therapy. In some embodiments, the combination therapy entails co-administration of an agent selected from: ara-C, taxol, cisplatin and vincristine In certain embodiments, the compound of the present disclosure is administered in combination or alternation with taxol. In another embodiment, the compound is administered in combination or alternation with cisplatin. In yet another embodiment, the compound of the present disclosure is administered in combination or alternation with vincristine. In a further embodiment, the compound of the invention is administered in combination or alternation with ara-C.

In some embodiments, a second agent having therapeutic activity via an immunosuppressive mechanism distinct from that of the compound of the present disclosure is administered in combination or alternation with the compound of the present disclosure. In other embodiments, a second agent having therapeutic activity via an immunosuppressive mechanism is administered in combination or in alternation with the compound of the present disclosure. In some embodiments, said administration of the second agent is before, after, or concomitantly with the administration of the compound of the present disclosure In some embodiments, administration of the compound of the invention is via an oral, intravenous, intraarterial, intramuscular, local, intraperitoneal, parenteral, transdermal, ocular, or intrathecal route. In some embodiments, the second agent is administered via the same route of administration as the compound of the present disclosure. In some embodiments of the subject methods, the administration of the second therapeutic agent is via a different route of administration from the compound of the present disclosure. Administration of the second therapeutic agent may be performed prior, conjointly, in the same composition, or subsequent to administration of the compound of the present disclosure.

For HIV/AIDS, operating through the protein kinase C (PKC)-NF-kB signaling pathway and selectively inducing transcriptional activation of reservoir cells, bryostatin is the most promising of all latency reversing agents (LRAs), including HDAC and bromodomain inhibitors ((a) Bullen, C. K.; Laird, G. M.; Durand, C. M.; Siliciano, J. D.; Siliciano, R. F. "New ex vivo approaches distinguish effective single agents for reversing FHV-1 latency in vivo" Nature Medicine 2014, 20(4), 425-429. (b) Archin, N.; Marsh Sung, J.; Garrido, C.; Soriano-Sarabia, N.; Margolis, D. "Eradicating FHV-1 infection: seeking to clear a persistent pathogen." Nat. Rev. Microbiol. 2014, 12, 750-764. (c) Barouch, D.; Deeks, S. "Immunologic strategies for HIV-1 remission and eradication." Science 2014, 345, 169-174; (d) Siliciano, J.; Siliciano, R. "Recent developments in the search for a cure for HIV-1 infection: Targeting the latent reservoir for HIV-1." J. Allergy Clin Immunol. 2014, 134, 12-19; (e) Chan, C. N.; Dietrich, I.; Hosie, M.; Willet, B. "Recent developments in human immunodeficiency virus-1 latency research." J. Gen. Virol. 2013, 94, 917-932). It also downregulates expression of HIV receptors CD4 and CXCR4, suppressing new infection. Bryostatin has shown to exhibit synergistic effects with HD AC inhibitors and bromodomain inhibitors (e.g. disulfiram, JQ1, panobinostat, romidepsin, vorinostat, bryostatin, prostratin, acetritin) to enhance the latency reversal effects ex vivo (Siliciano, J. Clin. Invest., 2015, 125, 1901, J Clin Invest. 2015; 125(5): 1901-1912. doi:10.1172/JCI80142. Nature Medicine 22, 807-811 (2016) doi:10.1038/nm.4124).

Pharmaceutical Preparations

Also provided are pharmaceutical preparations. Pharmaceutical preparations are compositions that include a bryostatin compound (for example one or more of the subject compounds, either alone or in the presence of one or more additional active agents) present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the present disclosure is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used.

When administered to a mammal, the bryostatin compounds and compositions of the present disclosure and pharmaceutically acceptable vehicles, excipients, or diluents may be sterile. In some instances, an aqueous medium is employed as a vehicle when the subject compound is administered intravenously, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference. The choice of excipient will be determined in part by the particular compound, as well as by the particular method used to administer the composition. Accordingly, there is a wide variety of suitable formulations of the subject pharmaceutical compositions.

Administration of the subject compounds may be systemic or local. In certain embodiments administration to a mammal will result in systemic release of a bryostatin compound of the present disclosure (for example, into the bloodstream). Methods of administration may include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, the bryostatin compounds and compositions of the present disclosure are administered subcutaneously. In certain embodiments, the bryostatin compounds and compositions of the present disclosure are administered orally. In certain embodiments, it may be desirable to administer one or more compounds of the present disclosure locally to the area in need of treatment. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

For the treatment of eye disorders, the pharmaceutical formulations of the present disclosure may be administered, e.g., by eye drops, subconjunctival injection, subconjunctival implant, intravitreal injection, intravitreal implant, sub-Tenon's injection or sub-Tenon's implant.

The bryostatin compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject bryostatin compound may also be formulated for oral administration. For an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, in some cases water or normal saline. If desired, the composition may also contain minor amounts of non-toxic auxiliary substances such as wetting agents, emulsifying agents, or buffers. In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freezedried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are appropriate. In some embodiments the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (e.g., sunblocking agents), etc.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of bryostatin compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host. In pharmaceutical dosage forms, the compounds may be administered in the form of a free base, their pharmaceutically acceptable salts, or they may also be used alone or in appropriate association, as well as in combination, with other pharmaceutically active compounds.

Dose levels can vary as a function of the specific bryostatin compound, the nature of the delivery vehicle, and the like. Desired dosages for a given compound are readily determinable by a variety of means. The dose administered to an animal, particularly a human, in the context of the present disclosure should be sufficient to effect a prophylactic or therapeutic response in the animal over a reasonable time frame, e.g., as described in greater detail herein. Dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1: Synthetic Strategy

Bryostatin is a macrocyclic lactone with 3 embedded pyranyl rings, 11 chiral centers, and 5 double bonds. The total synthesis of bryostatin described herein is accomplished through the joining of two comparably complex precursors that make up the "northern fragment" (containing the A ring of bryostatin) and the "southern fragment" (containing the C ring of bryostatin), using an esterification/macro-Prins cyclization strategy that concomitantly forms bryostatin's B ring. Each of the fragments is independently assembled, thereby providing a parallel time-saving synthesis. The southern fragment is produced in 13 or less, such as 12 or less, synthetic operations (steps) and the northern fragment is produced in 10 or less steps, such as 9 or less. Fragment coupling and completion of the synthesis includes a further 6 steps. The longest linear sequence is thus 19 steps, making the overall effort well within the capability of modern industrial scale synthesis.

The chemical starting reagents for the synthesis of the southern fragment are the commercially available 3,4-dihydro-2H-pyran and prenyl bromide. The total step count to complete the southern fragment is 13 steps from these reagents (overall yield about 16%). The synthetic sequence of the southern fragment is as follows (See FIG. 2 for depiction of the following steps):

Step 1) prenylation of 3,4-dihydro-2H-pyran with prenyl bromide to afford a linear octenyl diol. While this reaction has been reported in various forms, we have improved upon the best-reported yield by eliminating side-product formation by maintaining strict control over the pH of the initial hydrolysis reaction (3.5-4), optimizing the number of equivalents of allylic bromide used, and performing an acidic workup which serves to further eliminate side-products. Critically, the crude material produced from this reaction sequence can be used directly in the next operation without further purification.

Step 2) a double-oxidation of the diol to form an octenyl keto-aldehyde. Reaction conditions were developed to provide simultaneous oxidation of both the primary and secondary alcohols without any significant competing lactone formation.

Step 3) a one-flask, multi-reaction sequence involving the stereoselective crotylation of the aldehyde, a stereoselective pyran-forming cyclization to form the C ring (e.g., using the same acid and solvent as the crotylation), and oxygenation of the pyran through an epoxidation/methanolysis sequence. While the general sequence of cyclization/epoxidation is common in several bryostatin family syntheses, this three operation sequence is the first time that these reactions (in particular the menthone-mediated enantioselective crotylation with >99% ee) have been coupled together in a single flask, thus reducing the overall step count and minimizing waste and loss of material in workups and transfers. This is the shortest path reported (three steps) for accessing a strategically-functionalized precursor of the natural bryostatin C ring.

Step 4) an oxidation of a secondary pyranyl alcohol to a ketone was successfully achieved through the use of a mild oxidant that oxidizes both C20 alcohol diastereomers.

Step 5) an aldol reaction with methyl glyoxylate to install an exocyclic enoate. The best results are obtained when using freshly-distilled glyoxylate.

Step 6) a stereoselective Luche reduction of the pyranyl ketone to an alcohol.

Step 7) an esterification of the resulting pyranyl alcohol with octynoic anhydride (approx. 90% over 2 steps). This is a good point for diversification into analog structures, as the C20 ester is not necessary for high PKC binding affinity but can play a role in isoform selectivity, membrane association, sub-cellular localization, and/or other pharmacologic properties. The alkynoate provides a key intermediate that serves as a "masked" dienoate, allowing for subsequent oxidative reactions without affecting the side chain. Reaction concentration, time, and temperature were optimized to afford high yield of product. Conventional esterification strategies (e.g. carbodiimides, uronium/phosphonium reagents, mixed anhydrides) did not cleanly or efficiently deliver product.

Step 8) a stereo-, regio-, and chemoselective olefin dihydroxylation to afford a cis-diol. The Wender group is the only group to perform a late-stage Sharpless dihydroxylation to install the C25 and C26 diol, and this particular substrate is unique in that only one out of four pi systems in the molecule reacts in a short period of time to give the desired product in a high diastereomeric ratio (~11:1), with no detectable over-oxidation products.

Step 9) an acetonide protection of the resulting crude diol.

Step 10) an ozonolysis to convert an olefin to an aldehyde. Analogous ozonolysis reactions have been reported, but our yield is substantially improved (>90% vs. 46%). The ozonolysis proceeds with selective cleavage of the desired terminal alkene without affecting the other pi systems. This is one of several key transformations whose outcome and selectivity could not have been predicted.

Step 11/12) aldehyde homologation and C25/26 acetonide deprotection. No other group besides our own has reported being successful with this homologation strategy. This is a major challenge due to the steric encumbrance around the aldehyde. The reaction concentration and number of equivalents of zincate were optimized to achieve high yields.

Step 13) a regioselective alcohol protection. The route can be performed where steps 11-13 are run with just one column purification at the end, which is advantageous due to the fact that these intermediates are acid labile, and the final compound can be purified using neutralized (pH 7 buffered) silica. The final intermediate contains an aldehyde and alcohol that are used in subsequent manipulations to complete the total synthesis of bryostatin.

It is understood that that method described above can be performed by entering the synthesis at any convenient point in the sequence of steps, e.g., at Step 2, Step 3, Step 4, Step 5, Step 6, Step 7, Step 8, Step 9, Step 10, Step 11, Step 12 or Step 13 and progressing to the end of the sequence, thereby bypassing one or more of the first steps described. In such cases, any convenient alternative conventional methods can be utilized in preparing as a starting material, one of the intermediate compounds, e.g., one of the intermediate compounds (or an analog thereof) depicted in FIG. 2. In some cases, the southern fragment can be prepared according to the subject methods beginning at step 2. In some cases, the southern fragment can be prepared according to the subject methods beginning at step 3. In some cases, the southern fragment can be prepared according to the subject methods beginning at step 4. In some cases, the southern fragment can be prepared according to the subject methods beginning at step 5. In some cases, the southern fragment can be prepared according to the subject methods beginning at step 6. In some cases, the southern fragment can be prepared according to the subject methods beginning at step 7. In some cases, the southern fragment can be prepared according to the subject methods beginning at step 8. In some cases, the southern fragment can be prepared according to the subject methods beginning at step 9. In some cases, the southern fragment can be prepared according to the subject methods beginning at step 10. In some cases, the southern fragment can be prepared according to the subject methods beginning at step 11. In some cases, the southern fragment can be prepared according to the subject methods beginning at step 12/13.

The chemical starting reagents for the synthesis of the northern fragment are the commercially available ethyl 3,3-diethoxypropionate and t-butyl acetate. The total step count to complete the northern fragment is 10 steps from these reagents (overall yield about 13%). The synthetic sequence of the northern fragment is as follows (see FIG. 1 which depicts the following steps):

Step 1) a Claisen condensation to afford a ketoester. While Claisen condensations are well documented in the literature, crossed-Claisen condensations between two enolizable coupling partners are rare. Specifically, we found that sterically large substituents on both the electrophile (i.e. 3,3-diethoxy groups) and the nucleophile (t-butyl group) can suppress enolate exchange. Further, using excess enolate and warming the reaction mixture to room temperature provided for a high-yielding reaction. Lastly, we found that an acid wash of the crude material eliminated any basic impurities that are detrimental to the subsequent catalytic reduction. In some cases, an alternative conventional method can be utilized to arrive at the product of step 1).

Step 2) a stereoselective Noyori reduction of the C3 ketone. In some cases, an alternative conventional method can be utilized to arrive at the product of step 2).

Step 3) a silyl protection of the C3 alcohol, followed by an acidic workup to hydrolyze the C5 acetal. Of note, steps 1-3 of this sequence can be performed on 30 g scale by a single chemist in one week, requiring only a single chromatographic purification at the end of the sequence; this sequence is also 2-4 steps shorter than conventional processes previously reported in the literature.

Step 4) a stereoselective aldol reaction that couples two fragments of comparable complexity. We found that conventional Paterson aldol and Mukaiyama conditions were ineffective in efficiently delivering the desired 1,3-anti product. For the former, C9 carbonyl reduction occurred, and for the latter a variety of Lewis acids tested led to complex mixtures that were at best 1:1 d.r. Other metal-mediated reactions (Li, Zn, Sm) led to acyl rearrangements, again with poor selectivity. Thus, we developed a substrate-controlled reaction in which (a) the solvent composition (~20% diethyl ether in a hydrocarbon) and (b) the alkyl substituents on the boron triflate (i.e. diethyl) were important for obtaining high yields of the desired diastereomer. This high complexity-increasing reaction was vital to reducing overall step count and putting together a majority of the northern fragment in a single step.

Step 5) a highly diastereoselective (Evans-Saksena) ketone reduction using sodium triacetoxyborohydride, in a mixed solvent system of acetone, acetonitrile, and acetic acid. Of note, using the conventional conditions of acetonitrile and acetic acid only resulted in moderate selectivities. The addition of acetone as co-solvent reduced intermolecular reduction events to greatly enhance d.r. Further, we found that we could substitute tetrabutylammonium triacetoxyborohydride with the bench-stable, less-costly alternative, sodium triacetoxyborohydride. Therefore, our newly developed reaction conditions represent a significant methodological advance in achieving high diastereoselectivities and practicality on structurally complex, cyclic substrates.

Step 6) a pyran forming cyclization to form the A ring of bryostatin. Trimethylorthoformate was used as a dehydrating agent to drive the cyclization to completion.

Step 7) a one-flask C7 alcohol acetylation and chemoselective C9 acetal hydrolysis. We applied conditions to provide for the selective hydrolysis of the less substituted C9 acetal in the presence of C7 ketal.

Step 8) a highly stereoselective allylation reaction using a chiral diaminophenol controller. We are the first group to achieve the installation of this challenging allylsilane moiety in a single step; in contrast, conventional methods take up to three steps to perform the same transformation. Conventional allylation methodologies (Brown's, Keck's, Yamamoto's) failed to deliver the product.

Step 9) a silyl protection of the C11 alcohol.

Step 10) a chemoselective ester hydrolysis to the C1 carboxylic acid. In some cases, trimethyltin hydroxide is the preferred choice for this chemoselective cleavage between the C1 and C7 esters, The overall yield for the northern fragment is greater than 10% (e.g. 13%). The final intermediate contains an allyl silane and carboxylic acid that are used in subsequent reactions to complete bryostatin.

It is understood that the method described above can be performed by entering the synthesis at any convenient point in the sequence of steps, e.g., at Step 2, Step 3, Step 4, Step 5, Step 6, Step 7, Step 8, Step 9, or Step 10 and progressing to the end of the sequence, thereby bypassing one or more of the first steps described. In such cases, any convenient alternative conventional methods can be utilized in preparing as a starting material, one of the intermediate compounds, e.g., one of the intermediate compounds (or an analog thereof) depicted in FIG. 1. In some cases, the Northern fragment can be prepared according to the subject methods beginning at step 2. In some cases, the Northern fragment can be prepared according to the subject methods beginning at step 3. In some cases, the Northern fragment can be prepared according to the subject methods beginning at step 4. In some cases, the Northern fragment can be prepared according to the subject methods beginning at step 5. In some cases, the Northern fragment can be prepared according to the subject methods beginning at step 6. In some cases, the Northern fragment can be prepared according to the subject methods beginning at step 7. In some cases, the Northern fragment can be prepared according to the subject methods beginning at step 8. In some cases, the Northern fragment can be prepared according to the subject methods beginning at step 9. In some cases, the Northern fragment can be prepared according to the subject methods beginning at step 10.

It is understood that that method steps described above can be referred to as Step a, Step b, Step c, etc. and as such, will be understood as being equivalent to Step 1, Step 2, Step 3 etc. For example, the synthesis outlined in FIG. 1 is depicted as Steps a-Step j. It will be understood that Steps a-Step j are equivalent and in the same sequential order as Steps 1-Step 10 discussed above with reference to FIG. 1.

End Game:

To complete the synthesis of bryostatin 1, the northern and southern fragments are united via a Yamaguchi esterification between the C1 acid and C25 alcohol (FIG. 3). The macrocycle is then formed via a stereoselective Prins macrocyclization. Of note, our group has developed exceptionally mild conditions for effecting this transformation, which lends to the practicality and scalability of our route. The resulting B ring exocyclic olefin is then converted to a ketone via a stoichiometric ozonolysis reaction, which proceeds selectively in the presence of two other II systems.

The C20 octadienoate ester of bryostatin is synthesized through a facile octynoate isomerization reaction, using triphenylphosphine and phenol or 2,4,6-trimethylphenol in a suitable solvent (e.g., benzene) at room temperature (FIG. 3). In effect, the alkynoate moiety represents a novel protecting group for masking the functionality of a dienoate moiety in a bryostatin synthesis, which would have otherwise interfered with several of the oxidation chemistries employed in the synthesis. The exocyclic methyl enoate of the B ring is then installed using Fuji's chiral phosphonate or a more hindered chiral BINOL phosphonate, followed by a global deprotection to yield bryostatin 1. In some cases, the exocyclic methyl enoate of the B ring is installed using 3,3'-dimethyl-BINOL phosphonate, which gave a significantly higher Z:E ratio as compared to unsubstituted BINOL phosphonate (e.g. 11:1 vs 3:1 Z:E)

The steps outlined here have been validated, reproduced, and in some cases scaled up to multi-gram quantities. The final product is purified by reverse-phase HPLC to provide >99.5% pure material suitable for subsequent biological evaluation. Additionally, this route is amenable to syntheses of diverse bryostatin analog compound libraries. Many simplified analogs exhibiting superior activity are accessible by this route in significantly fewer steps. Nonpharmacophoric elements in positions such as, but not limited to, C13 (e.g., FIG. 6A, FIG. 6B and FIG. 6C), C12 and/or C14 (FIG. 6C), C20 (e.g., FIG. 9), C21, C26 (e.g., FIGS. 7 and 8), and/or C7 (e.g., FIG. 4) can be readily changed, simply by changing the starting reagents of reactions shown here. Finally, prodrug variants of bryostatin compounds, which can have a wider therapeutic window and reduced systemic toxicity, are also easily accessible via the subject methods using a single step, late-stage modification of the C26 alcohol. In summary, the subject methods provide for a uniquely short, cost effective, and practical synthetic supply of bryostatin 1 and a variety of analogs of bryostatin.

Example 1: Exemplary Synthetic Procedures

Southern Fragment:

1) To a one-neck, 250 mL round-bottom flask equipped with magnetic stir bar was added saturated aqueous $NH_4Cl$ (23 mL) and 0.01 M HCl (1.2 mL) to obtain a pH between 3.5-4. 3,4-Dihydro-2H-pyran (2.35 mL, 25.76 mmol, 1 equiv) was added via syringe over 1 min, during which time the solution became opaque with oily droplets. For the first hour, the pH was monitored and adjusted to maintain a stable pH between 3.5-4 (overall, 0.8 mL of 0.01M HCl were added). The hydrolysis of 3,4-Dihydro-2H-pyran to 2-hydroxy-tetrahydropyran was monitored by TLC and determined to be complete after 18 h (Note 1). The now-homogeneous reaction mixture was cooled with an ice bath (0° C.). THF (20 mL) was added, followed by zinc powder (5.73 g, 88.2 mmol, 3.4 equiv) as a single portion, and a solution of prenyl bromide (5.09 mL, 44.1 mmol, 1.7 equiv) in Et$_2$O (~2 mL) via syringe over ~10 min. After vigorously stirring for 5 min, TLC analysis indicated complete conversion of 2-hydroxy-tetrahydropyran and formation of the desired prenylated diol. The reaction mixture was directly concentrated via rotary evaporator to remove THF. The resulting aqueous mixture was diluted with 10% HCl (100 mL) to hydrolyze any C23-tetrahydropyran-protected product (Note 2). After 1.5 h, the reaction mixture was filtered over a plug of cotton (with copious water washings) to remove zinc. The filtrate was then transferred to a separatory funnel. The aqueous layer was extracted with EtOAc (200 mL, then 10×50 mL) until TLC of the aqueous layer no longer showed product. The combined organic layers were washed with a 1:1 mixture of saturated aqueous NaHCO$_3$ and brine (100 mL). This aqueous layer was then extracted with EtOAc (8×50 mL). The combined organic layers were dried over Na$_2$SO$_4$, filtered, and concentrated. This oil was diluted with CH$_2$Cl$_2$ (10 mL) and re-concentrated (repeated 5× to facilitate EtOAc removal) to afford the crude prenylated diol (4.25 g, 24.4 mmol, 94% yield based on quantitative $^1$H-NMR) as a viscous, cloudy, pale yellow oil. The crude prenylated diol was between 90-94% pure as determined by quantitative $^1$H-NMR using dimethyl phthalate as an internal standard. In practice, this material was sufficiently clean to employ for the subsequent Swern oxidation (step 2); however, the crude prenylated diol may be purified using one of two procedures: (A) purification by distillation (bp 85-95° C. at ~1 mmHg) to yield clear, colorless material with 96% purity (qNMR); (B) purification by silica gel flash column chromatography to yield material with >99% purity (qNMR). Note 1: Data for 2-hydroxy-tetrahydropyran: TLC R$_f$=0.36 (50% EtOAc/Hex), green spot in p-anisaldehyde; $^1$H-NMR (400 MHz, CDCl$_3$) diagnostic peaks δ 4.90 (t, J=5.5, 5.5 Hz, 1H), 4.05-3.95 (m, 1H), 3.58-3.49 (m, 1H). Note 2: On larger-scale (250 mmol) reactions, we have observed small amounts (typically <3%) of the C23-tetrahydropyran-protected diol. Data for C23-tetrahydropyran-protected diol: TLC R$_f$=0.76 in 50% EtOAc/Hex; $^1$H-NMR (400 MHz, CDCl$_3$): diagnostic peaks δ 5.81 (dd, J=17.5, 10.8 Hz, 1H), 5.10-5.01 (m, 2H), 4.59-4.55 (m, 1H).

2) To a flame-dried, three-neck, 2 L round-bottom flask equipped with magnetic stir bar, addition funnel, and internal reaction thermometer was added CH$_2$Cl$_2$ (~800 mL, 0.2M) and oxalyl chloride (40.5 mL, 463 mmol, 3 equiv). The reaction mixture was cooled with a dry ice/acetone bath (−78° C.). A solution of DMSO (43.85 mL, 617 mmol, 4 equiv) in CH$_2$Cl$_2$ (50 mL) was added dropwise via addition funnel (CAUTION: gas evolution), at a rate that maintained the internal temperature below −65° C. (~35 min). After 25 min at −78° C., a solution of prenylated diol from step 1 (26.6 g, 154 mmol, 1 equiv) in CH$_2$Cl$_2$ (100 mL) was added dropwise via addition funnel, at a rate that maintained the internal temperature below −65° C. (~15 min). The solution turned opaque and milky white during the course of this addition. After vigorously stirring for 2 h at −78° C., triethylamine (172 mL, 1.23 mol, 8 equiv) was added dropwise via addition funnel, at a rate that maintained the internal temperature below −65° C. (~25 min). Upon completion of addition, the reaction mixture was removed from the ice bath and stirred until the internal temperature reached −30° C. (~15 min). The reaction mixture was then poured into a separatory funnel containing 1M HCl (1.2 L) and pentane (800 mL). The layers were separated, and the aqueous layer was extracted with pentane (2×500 mL). The combined organic layers were washed with water, brine, dried over MgSO$_4$, filtered, and concentrated to afford an orange oil (87% yield by quantitative $^1$H-NMR using an internal standard, Note 1). Purification was accomplished by silica gel flash column chromatography (25% Et$_2$O/pentane) affording the ketoaldehyde product (20.9 g, 81% yield) as a straw-colored oil (Note 2). Compound purity was established by TLC (one spot) analysis. Note 1: Notwithstanding the appearance of the crude $^1$H-NMR, the crude ketoaldehyde product should be chromatographically purified to remove $^1$H-NMR-silent impurities. Note 2: The crude ketoaldehyde product can also be purified by distillation (bp 73-75° C. at ~3 mmHg), affording the pure ketoaldehyde product in 70% yield (10.0 g scale).

3) To a flame-dried, three-neck, 1 L round-bottom flask equipped with reflux condenser and magnetic stir bar was sequentially added ketoaldehyde from step 2 (3.03 g, 18.0 mmol, 1 equiv), chloroform (180 ml, 0.1 M), Nokami's crotyl transfer reagent (7.58 g, 36.0 mmol, 2 equiv), and p-TsOH—H$_2$O (342 mg, 1.80 mmol, 10 mol %). The crotylation reaction was stirred for 22 h, during which time the solution gradually became dark yellow/orange. After 22 h, TLC analysis indicated complete conversion of ketoaldehyde starting material. 4 Å powdered molecular sieves (27 g) were added in two portions, followed by additional p-TsOH—H$_2$O (342 mg, 1.80 mmol, 10 mol %). The flask was then placed in a 70° C. oil bath. After refluxing for 5 h, the cyclodehydration from the crotylated alcohol to the dihydropyran adduct was complete as determined by TLC (dihydropyran adduct: TLC R$_f$=0.5 in 100% pentane). The reaction mixture was cooled with an ice bath (0° C.), and solid NaHCO$_3$ (3.03 g, 36.0 mmol, 2 equiv) was added in a single portion, followed by methanol (60 mL). MMPP-6H$_2$O (80% pure, 5.02 g, 8.11 mmol, 0.45 equiv) was added in a single portion. After 40 min at 0° C., the reaction mixture was poured into a separatory funnel containing Et$_2$O (1 L) and saturated aqueous NaHCO$_3$ (750 mL) (Note: the molecular sieves settle to the bottom, aqueous layer). The layers were separated, and the aqueous layer was extracted with Et$_2$O (500 mL). The combined organic layers were washed with water (500 mL), brine (500 mL), dried over MgSO$_4$, filtered, and concentrated to afford the crude C20 alcohol (~2:1 dr at C20) as a yellow/orange oil. This crude material was used immediately in the next step without purification, as the C20 alcohol will decompose upon storage.

4) To a flame-dried, three-neck, 500 mL round-bottom flask equipped with magnetic stir bar was added Dess-Martin Periodinane (95% pure, 12.12 g, 27.03 mmol, 1.5 equiv) and CH$_2$Cl$_2$ (140 mL). The resulting clear and colorless solution was cooled with an ice bath (0° C.). Pyridine (14.5 mL, 180 mmol, equiv) was added via syringe, followed by a solution of the crude C20 alcohol from step 3 (assume 18.0 mmol, 1 equiv) in CH$_2$Cl$_2$ (20 mL with two washes, final concentration ~0.1M). The reaction mixture and ice bath were allowed to warm to room temperature. After 19.5 h, TLC analysis indicated complete conversion of the C20 alcohol to the corresponding C20 ketone. The now-orange solution was poured into a separatory funnel containing CH$_2$Cl$_2$ (1 L), saturated aqueous sodium thiosulfate (400 mL), and brine (200 mL). The layers were separated, and the aqueous layer was extracted with CH$_2$Cl$_2$ (500 mL). The combined organic layers were sequentially washed with saturated aqueous NaHCO$_3$ (500 mL) (CAUTION: gas evolution), 1M HCl (500 mL), water (500 mL), and brine (500 mL). The combined organic layers were then dried over MgSO$_4$, filtered, and concentrated. Purification was accomplished by silica gel flash column chromatography (0-10% Et$_2$O/petroleum ether) affording a 4:1 molar ratio of the C20 ketone product and isomenthone (Note 1). This mixture was then placed under vacuum (~1 mmHg) for two days to remove isomenthone, affording a pure sample of the C20 ketone product (3.12 g, 20:1 dr at C19, 69% combined yield over 2 steps) as a yellow oil. Compound purity was established by TLC (one spot) analysis. Note 1: The crotyl transfer reagent is converted into menthone as a result of the crotylation reaction. Some of this menthone then epimerizes to isomenthone, which partially co-elutes with the C20 ketone product.

5) To a flame-dried, one-neck, 100 mL round-bottom flask equipped with magnetic stir bar was added the C20 ketone from step 4 (1.51 g, 5.97 mmol, 1 equiv) and THF (33 mL, 0.18M). Potassium carbonate (4.52 g, 32.7 mmol, 5.5 equiv) was added in a single portion, with vigorous stirring. To the resulting suspension was added methyl glyoxylate (2M THF, 15 mL, 30 mmol, 5 equiv) via syringe (addition time of 1 min), followed by methanol (11 mL) via syringe (addition time of 1 min). The final reaction mixture consisted of a ~0.1M solution of 4.4:1 THF/MeOH. Upon addition of methanol, the suspension turned bright yellow, slowly darkening to orange over the course of the reaction. After 1 h, TLC analysis indicated complete conversion of the C20 ketone. The reaction mixture was poured into a separatory funnel containing saturated aqueous $NH_4Cl$ (250 mL). The layers were separated, and the aqueous layer was extracted with 1:1 $Et_2O$/pentane (3×250 mL). The combined organic layers were dried over $MgSO_4$, filtered, and concentrated to afford a crude, yellow oil. Purification was accomplished by silica gel flash column chromatography (5% EtOAc/pentane) affording the C21 (E)-enoate (1.61 g, 84% yield) as a neon yellow oil. Compound purity was established by TLC (one spot) analysis.

6) To a flame-dried, one-neck, 50 mL round-bottom flask equipped with magnetic stir bar was added the C21 (E)-enoate from step 5 (400 mg, 1.24 mmol, 1 equiv) and methanol (15 mL, 0.08M). The reaction mixture was cooled with an acetonitrile/dry ice bath (−50° C.). $CeCl_3·7H_2O$ (231 mg, 0.62 mmol, 0.5 equiv) was added in a single portion. After 10 min, $NaBH_4$ (94 mg, 2.48 mmol, 2 equiv) was added in a single portion. After an additional 20 min at −50° C., the initially yellow solution turned colorless, and TLC showed complete conversion of the C20 ketone to the C20 alcohol. The reaction mixture was warmed to room temperature by removing the ice bath and poured into a separatory funnel containing $Et_2O$ (30 mL) and a 3:2:1 mixture of saturated aqueous $NH_4Cl$/brine/water (40 mL) (caution: vigorous bubbling). The layers were separated, and the aqueous layer was extracted with $Et_2O$ (3×30 mL). The combined organic layers were washed with water (30 mL) and brine (30 mL), dried over $MgSO_4$, filtered, and concentrated to afford the crude C20 alcohol (400 mg) as a colorless oil.

7) To a flame-dried, 8-dram vial equipped with magnetic stir bar was added the crude C20 alcohol from step 6 (302 mg, 0.93 mmol, 1 equiv), $CH_2Cl_2$ (2.3 mL, 0.4M), and 2-octynoic anhydride (732 mg, 2.79 mmol, 3 equiv). The reaction mixture was cooled to −20° C. A solution of DMAP (113 mg, 0.93 mmol, 1 equiv) in $CH_2Cl_2$ (~500 µL) was added dropwise via syringe over ~3 min, resulting in a dark orange solution. After 1.5 h, the cooling bath had naturally warmed to 0° C., and TLC showed complete conversion of the C20 alcohol and formation of the C20 octynoate. The reaction mixture was quenched at 0° C. by adding saturated aqueous $NH_4Cl$ (5 mL). The layers were separated, and the aqueous layer was extracted with EtOAc (3×5 mL). The combined organic layers were washed with water (5 mL) and brine (5 mL), dried over $MgSO_4$, filtered, and concentrated to afford an orange oil. Purification was accomplished by silica gel flash column chromatography (10-20% $Et_2O$/pentane) affording the C20 octynoate (391 mg, >20:1 dr at C20, 94% yield over 2 steps) as a viscous yellow oil (Note 1). Compound purity was established by TLC (one spot) analysis. Note 1: We have observed that when using non-neutralized $CDCl_3$ for NMR analysis, the C20-ester can decompose. Thus, NMRs were taken in either neutralized $CDCl_3$ or $C_6D_6$.

8) A 500 mL round-bottom flask equipped with magnetic stir bar was sequentially charged with $K_2OsO_2(OH)_4$ (20 mg, 0.054 mmol, 1 mol %), $K_3Fe(CN)_6$ (5.37 g, 16.32 mmol, 3 equiv), $K_2CO_3$ (2.26 g, 16.32 mmol, 3 equiv), $MeSO_2NH_2$ (518 mg, 5.44 mmol, 1 equiv), $(DHQD)_2PHAL$ (212 mg, 0.27 mmol, mol %), and 1:1 $^tBuOH/H_2O$ (110 mL, 0.05M). The reaction mixture was vigorously stirred under nitrogen for 30 min, after which stirring was stopped. Separately, a 500 mL round-bottom flask equipped with magnetic stir bar was charged with the C20 octynoate from step 7 (2.43 g, 5.44 mmol, 1 equiv) and cooled with an ice bath (0° C.). Into the flask containing the C20 octynoate was poured the pre-mixed osmium solution. The resulting biphasic mixture was vigorously stirred at 0° C. and monitored for completion by TLC. After 100 min, the reaction mixture was poured into a separatory funnel containing water (150 mL) and EtOAc (150 mL). The layers were separated, and the aqueous layer was extracted with EtOAc (150 mL). The combined organic layers were washed with a solution of 3% sulfuric acid (w/v) saturated with potassium sulfate (100 mL) (see Note 1), brine (200 mL), dried briefly over $MgSO_4$, filtered, and concentrated to afford the crude C25/C26 diol as a purple/brown oil containing residual osmium. This crude material was used immediately in the next step without purification, as the C25/C26diol will decompose upon storage. Note 1: We found that residual $(DHQD)_2PHAL$ inhibits the subsequent acid-catalyzed ketalization step. Therefore, we employed a brief sulfuric acid/potassium sulfate wash to removed residual ligand from the crude product. However, we note that prolonged exposure to acid will result in the decomposition of the C25/C26 diol.

9) To a flame-dried, 100 mL round-bottom flask equipped with magnetic stir bar was added the crude C25/C26 diol from step 8 (assume 5.44 mmol, 1 equiv) and $CH_2Cl_2$ (55 mL, 0.1M). To the resulting solution was added 2,2-dimethoxypropane (2.7 mL, 21.764 mmol, 4 equiv) followed by PPTS (137 mg, 0.54 mmol, 10 mol %). After 40 min, TLC analysis indicated complete conversion of the C25/C26 diol and formation of the C25/C26 acetonide product. The reaction mixture was poured into a separatory funnel containing saturated aqueous $NaHCO_3$ (100 mL). The layers were separated, and the aqueous layer was extracted with $CH_2Cl_2$ (2×100 mL). The combined organic layers were dried over $MgSO_4$, filtered, and concentrated. Purification was accomplished by silica gel flash column chromatography (15-20% $Et_2O$/pentane) affording 2.03 g (72% yield) of diastereomerically pure C25/C26 acetonide and 464 mg of mixed isomers (1.21:1 dr), overall providing 2.49 g of C25/C26 acetonide (10.9:1 dr, 88% combined yield over 2 steps). Further chromatography provided diastereomerically pure product. Compound purity of the C25/C26 acetonide was established by TLC (one spot) analysis.

10) To a flame-dried, three-neck, 2 L round-bottom flask equipped with 500 mL jacketed addition funnel and magnetic stir bar was added the C25/C26 diol from step 9 (3.65 g, 7.01 mmol, 1 equiv) and $CH_2Cl_2$ (70 mL, 0.1 M). The reaction mixture was cooled with a dry ice/acetone bath (−78° C.). CH$_2$Cl$_2$ (500 mL) was added to the jacketed addition funnel, which was also cooled with dry ice/acetone. A saturated ozone solution (~0.025M CH$_2$Cl$_2$) was prepared by bubbling ozone (~4 LPM, prepared with 70 V) through the CH$_2$Cl$_2$ in the addition funnel until a bright blue color persisted (~10 min), at which point the headspace of the solution was purged with oxygen, and the addition funnel sealed with a septum and kept under a nitrogen atmosphere for the remainder of the reaction. The freshly-prepared ozone solution was then added dropwise to the reaction mixture over ~2 h: the reaction was monitored by TLC upon addition of 0.9 equiv. of ozone and determined to be incomplete; additional ozone was then added in 0.1 equiv portions until all of the starting material was consumed (~1.8 equiv, 500 mL). Subsequently, the reaction mixture was diluted with isopropanol (500 mL) and quenched by adding thiourea (3.34 g, 70.1 mmol, 10 equiv) as a single portion. The reaction mixture was warmed to room temperature by removing the dry ice bath. After 16 h, analysis by peroxide test strips indicated complete reduction of ozonide. The reaction mixture was poured into a separatory funnel containing Et$_2$O (800 mL) and H$_2$O (1.1 L). The layers were separated, and the aqueous layer was extracted with Et$_2$O (2×600 mL). The combined organic layers were washed with brine (1 L), and the combined aqueous layers back-extracted with Et$_2$O (500 mL). The combined organic layers were dried over MgSO$_4$, filtered, and concentrated. Purification was accomplished by silica gel flash column chromatography (10-40% Et$_2$O/pentane) affording the C17 aldehyde product (3.42 g, 93% yield) as a clear, colorless oil. Compound purity was established by TLC (one spot) analysis.

11) To a flame-dried, 8-dram vial equipped with magnetic stir bar was added cis-1-bromo-2-ethoxyethylene (95% pure, 257 µL, 2.30 mmol, 8 equiv) and Et$_2$O (957 µL, 0.3M) under Argon. The reaction mixture was cooled with a dry ice/acetone bath (−78° C.). t-BuLi (1.55M pentane, 2.96 mL, 4.59 mmol, 16 equiv) was added dropwise via syringe down the side of the vial over 1 min. The clear, colorless solution gradually turned into a cloudy, white suspension. After 30 min at −78° C., Me$_2$Zn (0.75M toluene, 3.37 mL, 2.53 mmol, 8.8 equiv) was added via syringe down the side of the vial (3 min). The suspended solids gradually began to aggregate. After 1 h at −78° C., a solution of the C17 aldehyde from the previous step (150 mg, 0.29 mmol, 1 equiv) in Et$_2$O (2.9 mL, 0.1M) was added via syringe down the side of the vial (3 min). The solution turned pale yellow, and the white solids gradually went into solution. After 1.5 h at −78° C., the reaction mixture was quenched by adding 1M HCl (18 mL, 8 equiv with respect to zincate) via syringe over 5 min. The reaction mixture was warmed to room temperature over ~30 min by removing the dry ice bath and vigorously stirred for 18 h, at which point TLC analysis indicated full conversion of the 1,2-addition adduct (TLC R$_f$=0.25, 20% EtOAc/Hex, purple spot in p-anisaldehyde) to the desired enal product. The layers were separated, and the aqueous layer was extracted with Et$_2$O (3×50 mL). The combined organic layers were dried over Na$_2$SO$_4$, filtered, and concentrated. Purification was accomplished via pH 7 buffered silica gel flash column chromatography (30% Et$_2$O/Hex) affording the enal product (122 mg, 78% yield) as an off-white foam. Compound purity was established by TLC (one spot) analysis.

12) To an 8-dram vial equipped with magnetic stir bar was sequentially added the enal from step 11 (54 mg, 0.10 mmol, 1 equiv), 4:1 MeCN/H$_2$O (5 mL, 0.02M), and p-TsOH—H$_2$O (186 mg, 1.0 mmol, 10 equiv) in a single portion. The colorless reaction mixture was stirred at room temperature for 28 h, in a 45° C. oil bath for 45 min, and then at room temperature for an additional 18 h, at which point the reaction mixture was one spot by TLC (Note 1). The reaction mixture was quenched at 0° C. by adding saturated aqueous NaHCO$_3$ (5 mL) via pipette and extracted with EtOAc (4×15 mL) until TLC of the aqueous layer no longer showed product. The combined organic layers were washed with brine (10 mL), dried over Na$_2$SO$_4$, filtered, and concentrated. Purification was accomplished by pH 7 buffered silica gel chromatography (80-100% EtOAc/Hex), affording the desired triol product (42 mg, 88% yield) as a white amorphous solid (Notes 2, 3). Compound purity was established by TLC (one spot) analysis. Note 1: By TLC, the C25/C26 acetonide is hydrolyzed within a few hours at room temperature while the C19-OMe requires extended reaction times: C25/C26 acetonide hydrolysis product with C19—OMe TLC R$_f$=0.38 (80% EtOAc/Hex, UV active, purple spot in p-anisaldehyde); triol product TLC R$_f$=0.24 (80% EtOAc/Hex, UV active, purple spot in p-anisaldehyde). Note 2: Buffered silica gel was prepared by adding 10% weight pH 7 phosphate buffer to silica and rotating for ~12 hrs. The triol product will decompose if exposed to a long column of silica gel. Note 3: The triol product will slowly polymerize over the course of weeks-to-months, even when stored in benzene at −20° C. Therefore, its C26 alcohol should be silyl protected as soon as possible.

13) To a flame-dried, 1-dram vial equipped with magnetic stir bar was added the triol product from step 12 (61 mg, 0.12 mmol, 1 equiv) and DML (650 µL, 0.2 M). Imidazole (22 mg, 0.33 mmol, 2.5 equiv) was added in a single portion, followed by TBS-Cl (29 mg, 0.19 mmol, 1.5 equiv). The reaction mixture was stirred for 1.5 h, at which point TLC analysis indicated complete conversion of starting material. The reaction mixture was poured into a separatory funnel containing saturated aqueous NH$_4$Cl (10 mL) and EtOAc (15 mL). The layers were separated, and the aqueous layer was extracted with EtOAc (10 mL). The combined organic layers were washed with water (2×10 mL) and brine (10 mL). The combined aqueous layers were then back-extracted with EtOAc (2×15 mL). The combined organic layers were dried over Na$_2$SO$_4$, filtered, and concentrated. Purification was accomplished by pH 7 buffered silica gel chromatography (100% pentane to elute TBS silanol, then 40% EtOAc/pentane to elute product), affording the C26 TBS ether product (56 mg, 75% yield) as an off-white foam. Compound purity was established by TLC (one spot) analysis.

Northern Fragment:

1') To a flame-dried, three-necked, 1 L round-bottom flask equipped with addition funnel and magnetic stir bar was added 3,3-dimethyl-2,4-pentanedione (10 g, 78 mmol, 1 equiv) and CH$_2$Cl$_2$ (195 mL, 0.4M). The reaction mixture was cooled with an ice/acetone bath (−10° C.). Triethylamine (25 mL, 179 mmol, 2.3 equiv) was added via syringe over 1 min, followed by TMS-OTf (31.1 mL, 172 mmol, 2.2 equiv) dropwise via addition funnel over 15 min. The reaction mixture and ice bath were allowed to warm to room temperature over 2 h. The solution gradually turned dark orange. After an additional 15 h, aliquot $^1$H-NMR indicated complete conversion of 3,3-dimethyl-2,4-pentanedione to the corresponding bis-enolsilane. $^1$H-NMR (300 MHz, CDCl$_3$): diagnostic peaks, mono-enolsilane of 3,3-dimethyl-2,4-pentanedione δ 4.27 (d, J=2.1 Hz, 1H), 4.15 (d, J=2.1 Hz, 1H); bis-enolsilane of 3,3-dimethyl-2,4-pentanedione δ 4.17 (d, J=1.5 Hz, 1H), 4.02 (d, J=1.5 Hz, 1H). The reaction mixture was cooled with a dry ice/acetone bath (−78° C.).

Triethylorthoformate (15.5 mL, 93.6 mmol, 1.2 equiv) was added via syringe over 1 min, followed by $BF_3$—$OEt_2$ (11.6 mL, 1.2 equiv) dropwise via syringe over 5 min; at this point, the solution turned a brighter yellow/orange. After 1.5 h at −78° C., TLC analysis indicated complete conversion of the bis-enolsilane and formation of the acetal adduct. Absolute ethanol (50 mL) was added via syringe over 5 min, followed by concentrated HCl (~12M, 600 μL). The reaction mixture was stirred at −78° C. for 10 min and then warmed to 0° C. with an ice/water bath. After 10 min at 0° C., TLC analysis indicated complete conversion of the acetal adduct and formation of the desired β-diketone product. The reaction mixture was quenched by adding saturated aqueous $NaHCO_3$ (300 mL) and extracted with $CH_2Cl_2$ (2×400 mL). The combined organic layers were washed with brine (300 mL), dried over $MgSO_4$, filtered, and concentrated to afford a dark orange oil. Purification was accomplished by silica gel flash column chromatography (1.5 L of 10-20% EtOAc/Hex) affording the β-diketone product (14.03 g, 78% yield) as a pale yellow oil. Compound purity of the product was established by TLC (one spot) analysis.

1) To a flame-dried, one-neck, 250 mL round-bottom flask equipped with magnetic stir bar was added diisopropylamine (17.3 mL, 123 mmol, 4.1 equiv) and THF (60 mL, 0.5 M). The reaction mixture was cooled with a dry ice/acetone bath (−78° C.). n-BuLi (2.5M Hex, 48 mL, 121.5 mmol, 4 equiv) was added dropwise via syringe over 10 min. After an additional 15 min at −78° C., t-butyl acetate (17.2 mL, 121.5 mmol, 4.05 equiv) was added via syringe down the side of the flask (10 min). After an additional 45 min at −78° C., ethyl-3,3-diethoxypropionate (5.8 mL, 30 mmol, 1 equiv) was added via syringe down the side of the flask (10 min). The reaction mixture was warmed to room temperature by removing the dry ice bath. After 90 min, the reaction mixture was quenched at 0° C. by adding saturated aqueous $NH_4Cl$ (60 mL) and extracted with $CH_2Cl_2$ (3×60 mL). The combined organic layers were dried over $MgSO_4$, filtered, and concentrated. The crude material was placed under vacuum (~1 mmHg) in a 50° C. oil bath for 12 h to remove t-butyl acetoacetate. The resulting material (8.6 g crude weight; 8:1 molar ratio of the desired β-ketoester product and 3° alcohol byproduct) was divided into two equal portions (4.3 g) for the next step (Noyori).

2) To a flame-dried, one-neck, 50 mL round-bottom flask was added the crude β-ketoester from step 1 (4.3 g, 16.4 mmol, assume 1 equiv) and methanol (16.4 mL, 1.0 M). The solution was degassed by sparging with Argon for 10 min and then transferred via syringe directly to the metal cylinder of a Parr apparatus equipped with magnetic stir bar. (R)-BINAP-$RUCl_2$ (55 mg, 0.06 mmol, 0.4 mol %) was added in one portion. With vigorous stirring, the Parr apparatus was charged to 200 psi with $H_2$ and vented (repeated 5×). The apparatus was then pressurized to 650 psi and placed in a 45° C. oil bath. After 48 h, the apparatus was allowed to cool to room temperature and depressurized. Aliquot $^1$H-NMR indicated full conversion of the β-ketoester starting material. The solution was transferred via syringe to a flame-dried, one-neck, 50 mL round-bottom flask equipped with magnetic stir bar. Concentrated sulfuric acid (66 μL, 1.2 mmol, 7.5 mol %) was added dropwise, and the reaction mixture was placed in a 60° C. oil bath. After 10 h, the trans-esterification to the methyl ester was complete as determined by aliquot $^1$H-NMR. The reaction mixture was quenched at 0° C. by adding saturated aqueous $NaHCO_3$ (60 mL) and extracted with $CH_2Cl_2$ (4×60 mL) until TLC of the aqueous layer no longer showed product. The combined organic layers were dried over $MgSO_4$, filtered, and concentrated to afford crude ß-hydroxy methyl ester. This crude material (3.3 g crude weight) was then divided into two portions for the next step (TBDPS protection).

3) To a flame-dried, two-neck, 50 mL round-bottom flask equipped with internal reaction thermometer and magnetic stir bar was added crude ß-hydroxy methyl ester from step 2 (1.0 g, 5.3 mmol, assume 1 equiv) and $CH_2Cl_2$ (10.6 mL, 0.5M). Imidazole (541 mg, 8.0 mmol, 1.5 equiv) was added in one portion, followed by TBDPS-Cl (1.38 mL, 5.3 mmol, 1 equiv) dropwise via syringe. After 4 h, TLC analysis indicated complete conversion of starting material. The reaction mixture was cooled with an ice bath (0° C.) and quenched by adding water (5.8 mL) followed by trifluoroacetic acid (5.8 mL), at a rate that maintained the internal temperature below 5° C. (~1 min). After 3 h at 0° C., aliquot $^1$H-NMR indicated complete hydrolysis of the C5 acetal. The layers were separated, and the aqueous layer was extracted with $CH_2Cl_2$ (3×10 mL). The combined organic layers were washed with saturated aqueous $NaHCO_3$ (20 mL), dried over $MgSO_4$, filtered, and concentrated. Purification was accomplished by silica gel flash column chromatography (5-10% EtOAc/Hex to elute silanol, then 10-20% EtOAc/Hex to elute product) affording the C5 aldehyde product (1.2 g) as a viscous, colorless oil. The remainder of crude ß-hydroxy methyl ester (2.3 g) was processed identically to afford an additional 2.3 g of the C5 aldehyde (3.5 g combined weight, 55% yield over 3 steps) (Note 1). Compound purity was established by TLC (one spot) analysis. Note 1: We have observed that the C5 aldehyde slowly decomposes, even when stored in a benzene matrix at −20° C. Therefore, the C5 aldehyde was used in the next step (aldol) as soon as possible.

4) Preparation of diethyl boron triflate (hexanes solution): To a flame-dried, one-neck, 200 mL round-bottom flask equipped with magnetic stir bar was added triethylborane (1M Hexanes, 29 mL, 29 mmol, 1 equiv) via syringe over 1 min. Triflic acid (2.55 mL, 29 mmol, 1 equiv) was added dropwise via glass syringe over 1 min. The reaction mixture was stirred for 60 min and immediately used without purification. Note 1: Triflic acid is insoluble in hexanes but over the course of several minutes, gas evolution is observed from the formation of ethane, and the solution becomes homogeneous and pale yellow. Note 2: The aldol crucially depends on the quality of triflic acid and diethyl boron triflate. Aldol: To a flame-dried, two-neck, 500 mL round-bottom flask equipped with magnetic stir bar was added the β-diketone from step 1' (6.8 g, 29.6 mmol, 2 equiv) and $Et_2O$ (59 mL, 0.25M). The reaction mixture was cooled with a dry ice/acetone bath (−78° C.). After 10 min, diethyl boron triflate (freshly-prepared hexanes solution, 29 mmol, 1.95 equiv) was added dropwise via syringe over 10 min. The reaction mixture turned pale yellow. After 10 min, Hunig's base (5.16 mL, 29.6 mmol, 2 equiv) was added dropwise via syringe over 10 min. The reaction mixture gradually turned orange-red. After 40 min at −78° C., $^1$H-NMR analysis from a MeOD quenching experiment indicated quantitative enolization (Note 1). n-Pentane (120 mL) was added via syringe down the side of the flask over 30 min, and the reaction mixture was cooled with a liquid $N_2$/MeOH bath (~95° C., Note 2). After 10 min, a solution of the C5 aldehyde from step 3 (5.7 g, 14.8 mmol, 1 equiv) in n-pentane (20 mL) was added dropwise over 5 min. After 4 h at −95° C., aliquot $^1$H-NMR indicated complete conversion of the C5 aldehyde. The reaction mixture was quenched by adding methanol (74 mL; 5 mL MeOH/1 mmol aldehyde) via pipette (~15 min), at a rate that maintained the internal temperature below −60° C. (at this point, the internal reaction temperature was monitored by placing a thermometer directly into the solution). The reaction mixture was warmed to −20° C. over ~15 min by removing the cooling bath, and then poured into a cooled (0° C.) Erlenmeyer flask containing Et$_2$O (100 mL) and pH 7.4 buffer (100 mL). After stirring for 10 min, the layers were separated, and the aqueous layer was extracted with Et$_2$O (5×200 mL). The combined organic layers were dried over MgSO$_4$, filtered, and concentrated. Purification was accomplished by pH 7 buffered silica gel flash column chromatography (7×13 cm), collecting 30 mL fractions and eluting with CH$_2$Cl$_2$ (1 L) followed by 33-50% Et$_2$O/Hex (1.5 L), affording a mixture of the hydroxy-ketone aldol product and its hemiketal isomer (7.8 g, 2:1 dr at C5, 86% combined yield) (Notes 3, 4). This mixture of open and closed isomers was used in the next step without separation, as they are in equilibrium. The C5 diastereomers were separated at a later stage in the sequence (after C11 silylation). However, a small portion of the material was purified by silica gel chromatography to afford a sample of the hemiketal isomer for characterization. Note 1: A 100 μL aliquot of the reaction mixture was rapidly quenched at −78° C. with MeOD. The resulting mixture was concentrated and analyzed by $^1$H-NMR in CDCl$_3$. Note 2: The diastereoselectivity of the reaction at −78° C. is ~1.6-1.8:1 dr (at C5). Note 3: The hydroxy-ketone aldol product slowly cyclizes to its hemiketal isomer even when stored in a benzene matrix at −20° C. Therefore, the product of this aldol reaction was generally isolated as a mixture of equilibrating isomers and used in the next step without separation. Note 5: Unreacted β-diketone from step 1' and the hemiketal isomer of the aldol product have similar retention factors on silica gel and are difficult to separate by chromatography. However, the mixture may be used together in steps 5 and 6, as the β-diketone is inert under the reaction conditions; afterwards, the compounds are readily separable.

5) Preparation of NaBH(OAc)$_3$ solution: To a flame-dried, one-neck, 250 mL round-bottom flask equipped with magnetic stir bar was added acetone (75 mL) via syringe, followed by acetic acid (75 mL) via syringe. The reaction mixture was cooled with an ice bath (0° C.). Sodium triacetoxyborohydride (23.8 g, 112 mmol, 5 equiv) was added in four portions over 10 min. The reaction mixture was vigorously stirred for 20 min, during which time the solution became homogeneous, and immediately used without purification.

Reduction: To a flame-dried, one-neck, 1 L round-bottom flask equipped with magnetic stir bar was added the aldol product from step 4 (13.8 g, 22.4 mmol, 1 equiv, Note 1). The flask was cooled with an ice bath (0° C.). Acetonitrile (37 mL) was added via syringe, followed by acetic acid (37 mL) via syringe. After 20 min, NaBH(OAc)$_3$ (150 mL of freshly-prepared solution) was added via nitrogen positive pressure cannula down the side of the flask (20 min). The final reaction mixture consisted of a 0.1M solution of 1:2:3 MeCN/acetone/AcOH. The reaction mixture and ice bath were allowed to warm to 15° C. over 2 h. After an additional 6 h, the reaction mixture was cooled with an ice bath and additional NaBH(OAc)$_3$ (9.5 g, 2 equiv) was added, this time as two solid portions over 5 min. The reaction mixture was again allowed to warm to 15° C. over 2 h. After an additional 10 h (total reaction time of 20 h), aliquot $^1$H-NMR indicated complete conversion of starting material. The reaction mixture was cooled with an ice bath (0° C.) and then poured into a cooled (0° C.) 2 L Erlenmeyer flask containing 50% Et$_2$O/petroleum ether (400 mL). The reaction mixture was quenched at 0° C. by adding saturated aqueous Rochelle's salt (250 mL) over 15 min. After vigorously stirring for 10 min, saturated aqueous NaHCO$_3$ (500 mL) was added over 30 min until bubbling ceased (CAUTION: significant amounts of carbon dioxide are generated). The layers were separated, and the aqueous layer was extracted with 80% Et$_2$O/petroleum ether (4×250 mL) until TLC of the aqueous layer showed no remaining product. The combined organic layers were dried over MgSO$_4$, filtered, and concentrated to afford the crude C7 alcohol, which was used in the next step without purification (the equilibrium between open and closed isomers complicated purification and $^1$H-NMR analysis).

6) To a flame-dried, one-neck, 1 L round-bottom flask equipped with magnetic stir bar was added the crude C7 alcohol (assume 22.4 mmol, 1 equiv) and 4:1 MeOH/CH(OMe)$_3$ (125 mL, 0.18M). The flask was cooled with an ice bath (0° C.), and PPTS (5.6 g, 6.2 mmol, 1 equiv) was added in one portion. The reaction mixture and ice bath were allowed to warm to 15° C. over 2 h. After an additional 22 h, aliquot $^1$H-NMR indicated complete conversion of starting material. The reaction mixture was cooled with an ice bath, diluted with cooled (0° C.) 50% Et$_2$O/petroleum ether (500 mL), and then quenched by adding saturated aqueous NaHCO$_3$ (250 mL) over 15 min. The layers were separated, and the aqueous layer was extracted with 80% Et$_2$O/petroleum ether (4×250 mL) until TLC of the aqueous layer showed no remaining product. The combined organic layers were dried over MgSO$_4$, filtered, and concentrated. Purification was accomplished by silica gel flash column chromatography (7×15 cm), collecting 30 mL fractions, and eluting with 10% EtOAc/petroleum ether (500 mL), 15% EtOAc/PE (500 mL), 20% EtOAc/PE (500 mL), 30% EtOAc/PE (500 mL), 40% EtOAc/PE (1 L), affording the C11 acetal product (11.5 g, >15:1 dr at C7, 85% combined yield) as a viscous, colorless oil (Note 1) Note 1: This reaction sequence (steps 5/6) was conducted with the 2:1 mixture of diastereomers obtained from the aldol step; the complete separation of diastereomers was performed following C11 silylation (step 9). However, the front fractions collected from the silica gel column are enriched in the desired aldol adduct. Therefore, this material was re-purified to afford a sample of the C11 acetal product for characterization.

7) To a flame-dried, one-neck, 500 mL round-bottom flask equipped with magnetic stir bar was sequentially added the C11 acetal product from step 6 (10.0 g, 16.6 mmol, 1 equiv, Note 1), CH$_2$Cl$_2$ (166 mL, 0.1M), and DMAP (203 mg, 1.66 mmol, 10 mol %). The reaction mixture was cooled with an acetonitrile/dry ice bath (−40° C.). 2,4,6-collidine (19.7 mL, 149 mmol, 9 equiv) was added via syringe over 5 min, followed by acetic anhydride (1.7 mL, 18.2 mmol, 1.1 equiv) via syringe (addition time of 2 min). After 4 h at −40° C., aliquot $^1$H-NMR indicated complete conversion of C7-alcohol 24 (diagnostic peak C9-OMe). TES-OTf (20.6 mL, 91.2 mmol, 5.5 equiv) was added dropwise via syringe down the side of the flask (addition time of 5 min). The solution gradually turned pink/brown. After 2 h at −40° C., a small reaction aliquot was quenched with H$_2$O and analyzed by $^1$H-NMR, which indicated complete conversion of the C11 acetal to the corresponding aldehyde (diagnostic peak C$_{11}$H). Therefore, the remainder of the reaction mixture was quenched by adding H$_2$O (166 mL) over 10 min. The now-frozen solution was placed in an ice bath (0° C.). After vigorously stirring for 2 h at 0° C., aliquot $^1$H-NMR indicated complete hydrolysis of the C11 acetal. The layers were separated, and the aqueous layer was extracted with CH$_2$Cl$_2$ (3×250 mL). The combined organic layers were dried over MgSO$_4$, filtered, and concentrated to ~100 mL. At this point, 5% EtOAc/Hex (250 mL) was added to precipitate collidine-triflate salts. The resulting suspension was concentrated to ~30 mL. The supernatant was transferred via pipette to the top of a slurry-packed silica gel column (7×18 cm), using several thorough washings (Note 2), which was eluted with 5-40% EtOAc/Hex (2.5 L) to afford the C11 aldehyde product (7.7 g, 78% yield) as a viscous, colorless oil (Note 1). Note 1: This reaction was conducted with the 2:1 mixture of diastereomers obtained from the aldol step; the complete separation of diastereomers was performed following C11 silylation (step 9). However, a small portion was diastereomerically enriched to afford a sample of the C11 aldehyde for characterization. Note 2: The remaining collidine-triflate salts were dissolved in $CH_2Cl_2$ and analyzed by TLC to confirm that all of the crude material was transferred to the silica gel column.

8) Preparation of diaminophenol and DBU solution: To a flame-dried, one-neck, 100 mL round-bottom flask equipped with magnetic stir bar was added diaminophenol (6.17 g, 21.2 mmol, 1.2 equiv) and $CH_2Cl_2$ (30 mL, 0.6 M). The reaction mixture was cooled with an ice bath (0° C.), and DBU (9.53 mL, 63.7 mmol, 3.6 equiv) was added dropwise via syringe over 5 min. The reaction mixture was stirred for 5 min and used immediately.

Allylation: To a flame-dried, one-neck, 250 mL round-bottom flask equipped with magnetic stir bar was added a solution of the trichlorosilane (7.4 g in 40 mL $CH_2Cl_2$, 28.3 mmol, 1.6 equiv). The reaction mixture was cooled with an ice bath (0° C.), and the freshly prepared solution of diaminophenol/DBU was added dropwise via syringe (addition time of 5 min). The reaction mixture was allowed to warm to room temperature by removing the ice bath. After 30 min, the reaction mixture was cooled with a liquid $N_2$/MeOH bath (−95° C., Note 1). A solution of the C11 aldehyde product from step 7 (10.6 g, 17.7 mmol, 1 equiv, Note 2) in $CH_2Cl_2$ (20 mL; final volume 89 mL $CH_2Cl_2$, 0.2M) was added via syringe down the side of the flask (5 min). After 2 h, TLC analysis indicated complete conversion of starting material. The reaction mixture was diluted with hexanes (20 mL) and quenched with TBAF (1M THF, 17.7 mL, 1 equiv) dropwise via syringe (5 min), followed by pH 7.4 buffer (100 mL) over 5 min. The reaction mixture was allowed to warm to 0° C. by removing the cooling bath. After 15 min, the layers were separated, and the aqueous layer was extracted with $CH_2Cl_2$ (5×200 mL) until TLC of the aqueous layer no longer showed product. The combined organic layers were dried over $MgSO_4$, filtered, and concentrated to ~30 mL (the residual solvent enables easy transfer of an otherwise viscous crude reaction mixture). Purification was accomplished by silica gel flash column chromatography (7×15 cm), collecting 30 mL fractions, and eluting with 10% $Et_2O$/petroleum ether (1 L), 20% $Et_2O$/PE (1 L), 30% $Et_2O$/PE (1 L), 40% $Et_2O$/PE (1 L), affording product 28 (10.8 g, 10:1 dr at C11, 84% combined yield) as a colorless oil (Note 2). For recovery of diaminophenol, see Note 3. Note 1: The diastereoselectivity of the reaction at −78° C. is approximately 8:1 dr (at C11).

Note 2: This reaction (step 8) was conducted with the 2:1 mixture of diastereomers obtained from the aldol step; the complete separation of diastereomers was performed following C11 silylation (step 9). However, a small portion was purified to afford a sample of the allylation product for characterization.

Note 3: ~50% of diaminophenol was recovered by (a) flushing the silica gel column with 80-100% EtOAc/Hex and (b) treating the aqueous layer from the reaction workup with 1 M NaOH at 0° C., followed by exhaustive extraction with $CH_2Cl_2$. The combined solids were recrystallized from hot hexanes.

9) To a flame-dried, one-neck, 250 mL round-bottom flask equipped with magnetic stir bar was added the allylation product from step 8 (10 g, 13.8 mmol, 1 equiv, Note 1) and $CH_2Cl_2$ (92 mL, 0.15M). The reaction mixture was cooled with an ice bath (0° C.). Imidazole (5.6 g, 82.5 mmol, 6 equiv) was added in one portion, followed by TES-Cl (3.46 mL, 20.6 mmol, 1.5 equiv) dropwise via syringe over 3 min. After 3 h, TLC analysis indicated full conversion of starting material. The reaction mixture was quenched by adding pH 7.4 buffer (100 mL) dropwise over 10 min. The layers were separated, and the aqueous layer was extracted with $CH_2Cl_2$ (5×150 mL). The combined organic layers were dried over $MgSO_4$, filtered, and concentrated. Purification was accomplished by silica gel flash column chromatography (7.5×15 cm), eluting with 10-20% $Et_2O$/petroleum ether (3 L), affording the C11 TES ether product (11.1 g, 96% yield) as a colorless oil (Note 1). Compound purity was established by TLC (one spot) analysis.

Note 1: This reaction (step 9), as well as ah previous reactions following step 4, were conducted with the 2:1 mixture of diastereomers obtained from the aldol step (step 4). The complete separation of diastereomers was performed following C11 silylation, as the diastereomers were found to be the most readily separable at this stage. Purification of the desired diastereomer was accomplished via silica gel flash column chromatography using a gradient elution (5-10-15-20% $Et_2O$ in petroleum ether). Purification was typically carried out on ~5 grams of material using a 9×40 cm column, affording ~33% of the desired diastereomer, ~50% as a mixture of diastereomers, and ~17% of the undesired diastereomer. Mass recoveries >95% were obtained, and the mixed material was iteratively re-subjected to purification.

10) In a nitrogen-atmosphere glove box, a flame-dried, one-neck, 100 mL round-bottom flask equipped with magnetic stir bar was charged with $Me_3Sn$—OH (2.15 g, 11.90 mmol, 3.5 equiv). The flask was removed from the glove box and placed under an atmosphere of Argon (balloon). A solution of the C11 TES ether from the previous step (2.86 g, 3.40 mmol, 1 equiv) in toluene (30 mL, 0.11M) was added via syringe, and the resulting mixture was placed in an 85° C. oil bath, affording a cloudy solution. After 14 h at 85° C., TLC and aliquot $^1$H-NMR indicated complete conversion of starting material and formation of the C1 acid product (along with ~30% of the C7-des-OAc compound). To re-esterify the C7 des-acetate, the reaction mixture was allowed to cool to room temperature. DMAP (2.49 g, 20.4 mmol, 6 equiv) was added in one portion, and the resulting suspension was cooled with an ice bath (0° C.). Acetic anhydride (1.60 mL, 17.0 mmol, 5 equiv) was added dropwise via syringe. After 15 min at 0° C., saturated aqueous $NaHCO_3$ (30 mL) was added, and the resulting biphasic mixture was allowed to warm to room temperature by removing the ice bath. After 4 h of vigorous stirring, the reaction mixture was poured into a separatory funnel containing saturated aqueous $NH_4Cl$ (200 mL). The layers were separated, and the aqueous layer was extracted with EtOAc (3×100 mL) until TLC of the aqueous layer no longer showed product. The combined organic layers were dried over $MgSO_4$, filtered, and concentrated. Purification was accomplished by silica gel flash column chromatography (2 L of 10-50% $Et_2O$/pentane) affording the C1 acid product (2.48 g, 88% yield) as a white foam (Note 1). Compound purity was established by TLC (one spot) analysis. Note 1: The C1 acid was found to be prone to C9-OMe hydrolysis. Therefore, the compound was either frozen in benzene at −20° C. or used immediately in the next step (Yamaguchi esterification). NMRs were taken in either neutralized $CDCl_3$ or $C_6D_6$.

Endgame:

1) To a flame-dried, 500 mL round bottom flask was added a solution of northern fragment (2.72 g, 3.28 mmol, 1 eq.) in anhydrous toluene (131 mL, 0.025 M). The reaction mixture was cooled with an ice bath (0° C.). Triethylamine (2.75 mL, 19.7 mmol, 6 eq.) was then added dropwise via syringe over 30 seconds, followed by 2,4,6-trichlorobenzoyl chloride (924 µL, 5.91 mmol, 1.8 eq.) dropwise via syringe over 15 seconds. The reaction was stirred at room temperature under nitrogen for 2 hours, after which time the reaction became cloudy with salts. Then, the reaction mixture was re-cooled to 0° C. Separately, a flame-dried, 250 mL round-bottom flask was charged with a solution of southern fragment (2.00 g, 3.28 mmol, 1 eq.) and DMAP (1.20 g, 9.85 mmol, 3 eq.) in toluene (131 mL, 0.025 M). The solution of the southern fragment was sonicated to ensure homogeneity, then transferred to the flask containing the northern fragment via syringe over 10 min. The reaction mixture was warmed to room temperature by removing the ice bath. The solution turned yellow-orange and even cloudier. After 45 min, TLC analysis indicated complete conversion of the southern fragment. The reaction mixture was cooled to 0° C. and quenched by adding $H_2O$ (200 mL) slowly over 5 min. The layers were separated, and the aqueous layer was extracted with 20% EtOAc/Hex (5×100 mL). The combined organic layers were dried with $Na_2SO_4$, filtered, and concentrated. Purification was accomplished by pH 7.0 buffered silica gel flash column chromatography (5.5×10 cm), collecting 20 mL fractions, and eluting with 5% EtOAc/Hex (500 mL), 10% EtOAc/Hex (500 mL), and 20% EtOAc/Hex (500 mL), to yield 3.82 g (82%) of product ester as an off-white foam.

2) The product ester from step 1 (3.82 g, 2.69 mmol, 1 eq.) was added to a flame-dried one-neck, 500 mL round-bottom flask equipped with magnetic stir bar, followed by methanol (135 mL, 0.02 M) and trimethylorthoformate (2.69 mL, 2% of MeOH volume). The reaction mixture was cooled with an ice bath (0° C.) and PPTS (203 mg, 0.81 mmol, 30 mol %) was then added in one portion. The reaction and the ice bath were allowed to warm to room temperature with stirring over 1.5 h. After an additional 20 h, the reaction mixture was cooled with an ice bath (0° C.), diluted with hexanes (100 mL), and quenched with saturated aqueous $NaHCO_3$ (50 mL) followed by water (100 mL). After extraction and separation of the layers, the aqueous layer was then re-extracted with 25% EtOAc/Hex (5×100 mL) until TLC of the aqueous layer no longer showed product. The combined organic layers were dried over $Na_2SO_4$, filtered, and concentrated. The crude oil was then subjected to silica gel column chromatography (5.5×9 cm, 2 L of 10-35% EtOAc/Hex) to yield 2.49 g (76%) of product macrolactone as a white foam, and the C26-des-TBS macrocycle (320 mg, 11%).

3) Preparation of saturated ozone solution (~0.03 M $CH_2Cl_2$): A one-neck, 500 mL round-bottom flask equipped with magnetic stir bar was charged with $CH_2Cl_2$ (~250 mL) and cooled with a dry ice/acetone bath (−78° C.). Ozone (~4 LPM, prepared with 70 V) was bubbled through the solution until a bright blue color persisted (~15 min), at which point the headspace of the solution was purged with $O_2$ and sealed with a septum.

Ozonolysis: To a flame-dried, one-neck, 500 mL round-bottom flask equipped with magnetic stir bar was added the macrolactone product from step 2 (1.26 g, 1.04 mmol, 1 equiv) and methanol (83 mL, 0.0125M). After stirring for 5 min, the homogeneous reaction mixture was cooled with a dry ice/acetone bath (−78° C.). The solution turned slightly cloudy. Ozone (~0.03M $CH_2Cl_2$, 3 mL, 0.09 equiv) was added slowly via syringe down the side of the flask (addition time of ~1 min). After 5 min, the reaction was monitored by TLC and determined to be incomplete (Note 1). Additional ozone was then added in 3 mL (0.09 equiv) portions until starting material could no longer visualized by UV (Note 2). The total amount of ozone solution added was 66 mL (~1.9 equiv); the total time required to add this solution was ~3 h. The reaction mixture was quenched by adding triphenylphosphine (545 mg, 2.08 mmol, 2 equiv) as a single portion. After 5 min, the reaction mixture was warmed to room temperature by removing the dry ice bath. After 80 min, both TLC and peroxide test strips indicated complete conversion of the intermediate peroxide (Note 1). The reaction mixture was concentrated to ~10 mL (Note 3) and directly purified by pH 7.0 buffered silica gel flash column chromatography (5.5×11.5 cm, 2 L of 5-40% EtOAc/Hex) affording unreacted alkene (141 mg) and the C13-ketone product (1.01 g, 80% yield, 90% brsm) as a white foam (Note 4).

Note 1: TLC eluent of 25% EtOAc/Hex with residual $MeOH/CH_2C_{1-2}$ from TLC capillary tube Starting material: $R_f$=0.74 (UV active, dark purple spot in p-anisaldehyde)

intermediate peroxide: $R_f$=0.52 (UV active, yellow spot in p-anisaldehyde)

C13-ketone product: $R_f$=0.63 (UV active, yellow spot in p-anisaldehyde)

Note 2: To minimize over-oxidation products, this reaction was only run to partial conversion. Specifically, ozone was only added if the macrolactone starting material could be visualized by UV (TLC); however, starting material was still present when the TLC plate was treated with p-anisaldehyde stain and heated.

Note 3: The crude reaction mixture should not be fully concentrated as this action may promote byproduct formation arising from conjugate addition of triphenylphosphine. Similarly, the crude mixture should be purified as soon as possible to remove triphenylphosphine.

Note 4: All endgame intermediates (i.e. post-Yamaguchi esterification) were found to be prone to C9-OMe hydrolysis. Therefore, NMRs were taken in either neutralized $CDCl_3$ or $C_6D_6$.

4) The C13 ketone from step 3 (2.0 g, 1.65 mmol, 1 eq.) was added to a flame-dried, one-neck, 100 mL round-bottom flask equipped with magnetic stir bar in benzene (16.5 mL, 0.1M). The flask was cooled with an ice bath (0° C.). Triphenylphosphine (2.16 g, 8.23 mmol, 5 eq.) and 2,4,6-trimethylphenol (1.12 g, 8.23 mmol, 5 eq.) were sequentially added as single portions. The reaction mixture and the ice bath were allowed to warm to room temperature over 1 hour. After stirring at room temperature for an additional 18 hours, TLC analysis indicated complete conversion of the starting material. The entire reaction mixture was then loaded directly onto a pH 7.0 buffered silica gel column (5×8 cm, 500 mL of 5% EtOAc/Hex to elute triphenylphosphine and 2,4,6-trimethylphenol, then 1.5 L of 10-35% EtOAc/Hex) affording a mixture of cis-trans-dienoate (114 mg, 6%) and a trans-trans-dienoate (1.8 g, 90%) as white foams (Note 4 above). Further chromatography provided isomerically pure product.

5) To a flame-dried, one-neck, 250 mL round-bottom flask equipped with magnetic stir bar was added the chiral phosphonate reagent (6.05 g, 14 mmol, 14 eq.) in THF (25 mL, 0.04M). The reaction mixture was cooled to −78° C. To this solution, NaHMDS (13 mL, 1M solution in THF, 13 mmol, 13 eq.) was added dropwise via syringe over 1 min. The reaction mixture was stirred at −78° C. for 30 minutes, then a solution of C13-ketone from step 4 (1.22 g, 1 mmol, 1 eq.) in THF (12 mL, final volume 50 mL THF, 0.02M) was added dropwise via syringe over 1 min. After 5 min at −78° C., the flask was transferred to a 4° C. cold room. The solution gradually turned yellow/orange. After 70 hours at 4° C. (note 5), the reaction mixture was quenched at 4° C. by adding saturated aqueous $NH_4Cl$ (10 mL) and diluting with $Et_2O$ (100 mL). The phases were separated, and the aqueous layer was extracted with $Et_2O$ (5×50 mL). The combined organic layers were dried over $Na_2SO_4$, filtered, and concentrated to about 15 mL (note 6). Crude product was purified via silica gel flash column chromatography (2 L of 25-35% $Et_2O$/Hex to elute product, then 750 mL EtOAc to elute unreacted phosphonate) affording the C13 enoate product (1.17 g, 92% yield as a 11.6:1 Z:E mixture at C13) and unreacted phosphonate (3.72 g, 66% recovered yield) (note 7). Further chromatography gives the product enoate in greater than 30:1 Z:E ratio. Note 5: Shorter reaction times (e.g. 36-48 h) can be obtained by increasing the eq. of the chiral phosphonate reagent, however, a slight drop in selectivity accompanies this change (e.g. using NaHMDS (15.5 eq.) and chiral phosphonate reagent (17 eq.) affords the enoate product in 8.5:1 Z:E, 90% combined yield on 500 mg scale).

Note 6: Residual THF enables easy transfer of unreacted phosphonate. Additionally, a small amount of DCM may be used to fully transfer the crude product onto the silica gel column if required. Alternatively, the reaction mixture may be "dry loaded" by (a) dissolving the crude moisture in EtOAc and adding about 10× its weight in silica gel; (b) concentrating the resulting solution via rotary evaporator, with a cotton plug in the bump trap to minimize silica gel loss; and (c) transferring the compound adsorbed silica onto the top of a slurry-packed column with 25% $Et_2O$/Hex.

Note 7: On some larger scale reactions, full conversion the $C_{1-3}$-ketone from step 4 is not achieved (typically, 2-3% of unreacted starting material remains). In these cases, the back fractions collected from the column contain both starting material and product. Rather than separate this mixture via chromatography, it may be more convenient to pool samples from several reactions together and re-subject the combined mixture to the reaction conditions for step 5 a second time.

Retention factors; TLC eluent of 25% EtOAc/Hex
  C13 ketone from step 4: $R_f$=0.29 (UV active, yellow/brown spot in p-anisaldehyde).
  (Z)-enoate product of step 5: $R_f$=0.35 (UV active, dark purple spot in p-anisaldehyde).

6) To a 50 mL polypropylene Falcon tube equipped with magnetic stir bar was added a solution of C13 enoate from step 5 (170 mg, 30:1 Z:E at C13, 0.134 mmol, 1 eq.) in THF (7.1 mL). The reaction mixture was cooled with an ice bath (0° C.). HF·Pyr (3.55 mL, 30% HF, 70% Pyr) was added via a plastic Luer Lock syringe down the side of the tube over about 1.5 min, affording a 0.0075M solution of 1:2:2 HF-pyr/THF/pyridine mixture. The reaction mixture was placed in a 40° C. oil bath. After 19.5 h at 40° C., TLC analysis indicated full conversion of the starting material. Water (3.55 mL) was then added via syringe down the side of the tube over about 1 min. After an additional 2.5 h at 40° C. (note 8), the reaction mixture was allowed to cool to room temperature and quenched by slowly syringing the solution directly into the aqueous layer in a separatory funnel containing saturated aqueous $NaHCO_3$ (130 mL, chilled on ice before use) and EtOAc (50 mL). The falcon tube was washed with additional saturated aqueous $NaHCO_3$ (10 mL) and EtOAc (3×10 mL). After bubbling ceased, the layers were separated, and the aqueous layer was extracted with EtOAc (2×50 mL). The combined organic layers were washed with 1M HCl (110 mL, chilled on ice before use) to remove pyridine, brine (50 mL), dried over $Na_2SO_4$, filtered and concentrated. The crude material was purified by silica gel flash column chromatography (loaded with DCM then 10-35-45% EtOAc/pentane) to yield 96.2 mg (80%) of Bryostatin 1, still as a mixture of Z:E isomers at C13(18:1 Z:E). This mixture was then purified by reverse-phase HPLC to yield bryostatin 1.

Procedure in PFA round-bottom flask: A 100 mL PFA round-bottom flask (Chemglass LifeSciences) equipped with magnetic stir bar was charged with C13 enoate from step 5 (552 mg, 9.2:1 Z:E at C13, 0.434 mmol, 1 equiv), THF (23 mL), and pyridine (23 mL). The reaction mixture was cooled with an ice bath (0° C.). HF-pyridine (11.5 mL) was added via a plastic Luer Lock syringe down the side of the flask (addition time of ~1.5 min), affording a ~0.0075M solution of 1:2:2 HF-pyr/THF/pyridine. The reaction mixture was placed in a 40° C. oil bath. After 20 h at 40° C., TLC analysis indicated full conversion of the C13 enoate from step 5. Water (11.5 mL) was added via syringe down the side of the flask (~1 min). After an additional 2.5 h at 40° C. (note 8), the reaction mixture was allowed to cool to room temperature and quenched by slowly syringing the solution directly into the aqueous layer in a separatory funnel containing saturated aqueous $NaHCO_3$ (410 mL, chilled on ice before use) and EtOAc (150 mL) (CAUTION: significant amounts of carbon dioxide are generated). The flask was washed with additional saturated aqueous $NaHCO_3$ (30 mL) and EtOAc (3×20 mL). After bubbling ceased, the layers were separated, and the aqueous layer was extracted with EtOAc (2×150 mL). The combined organic layers were washed with 1M HCl (340 mL, chilled on ice before use) to remove pyridine, additional saturated aqueous $NaHCO_3$ (50 mL), and brine (100 mL). The combined organic layers were then dried over $Na_2SO_4$, filtered, and concentrated. Purification was accomplished by silica gel flash column chromatography (10-35-45% EtOAc/pentane) affording bryostatin 1 (304 mg, 8.7:1 Z:E at C13, 77% combined yield) as a white solid.

Note 8: A C9-F intermediate is initially formed, which is hydrolyzed upon stirring with water for 2.5 h at 40° C. $^{19}$FNMR showed no peaks corresponding to the C9-F intermediate after flash column chromatography: 19F-NMR (377 MHz, $CDCl_3$) δ −128.0.

Figure 11A:
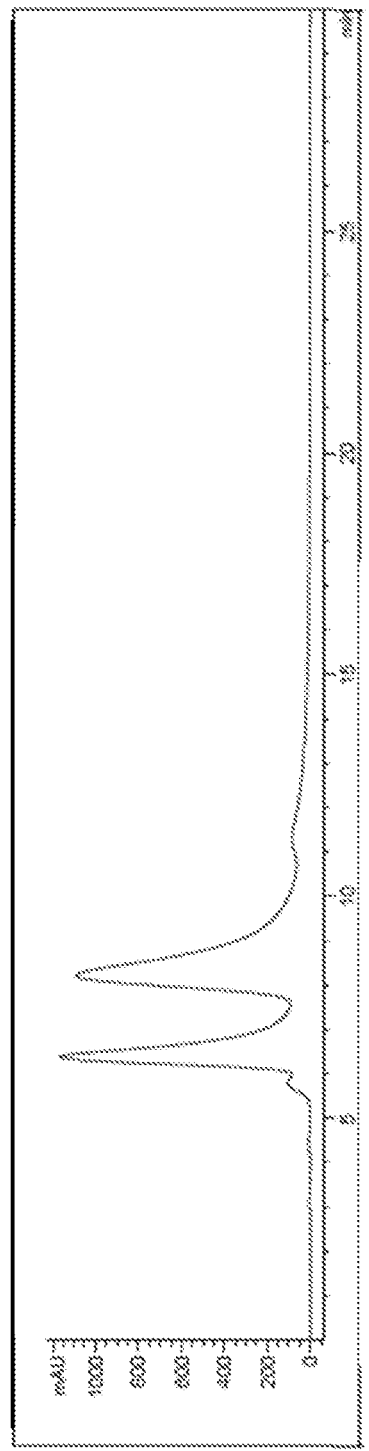
FIG. 11A shows Synthetic bryostatin 1 along with the E enoate isomer.
Figure 11B:
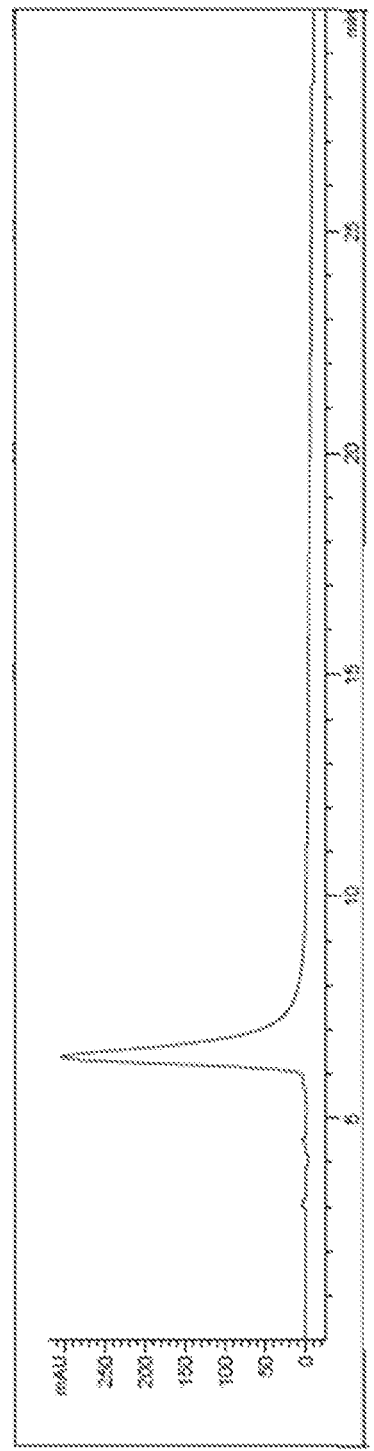
FIG. 11B shows the trace for HPLC purified synthetic bryostatin 1.
Figure 11C:
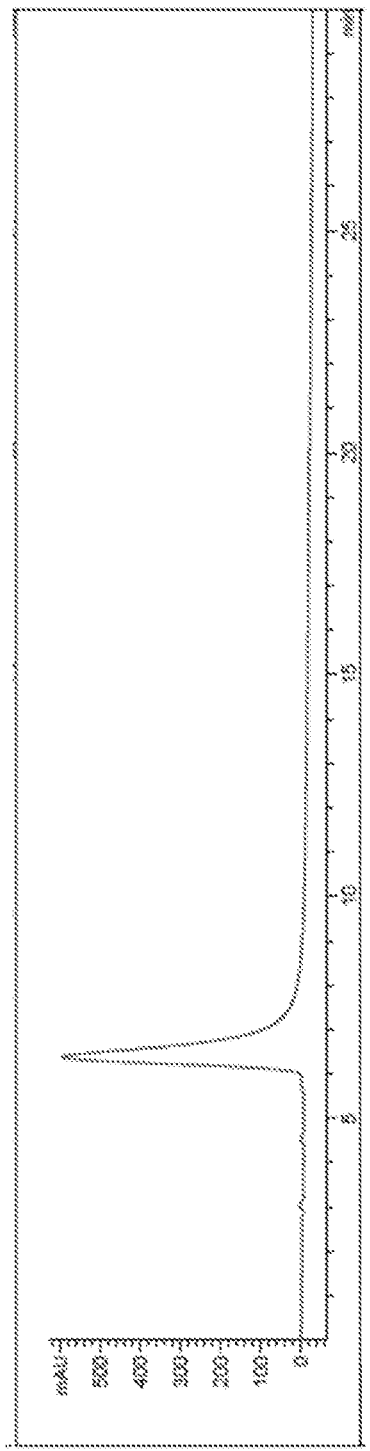
FIG. 11C shows the trace for the NCI sample of bryostatin 1.

Preparative HPLC: Bryostatin 1 (as a ~10:1 Z:E mixture of C13 enoate isomers) was further purified by preparative HPLC using a Varian ProStar 210 Solvent Delivery System with an Agilent ProStar 325 detector set to detect at 256 nm and 214 nm. Separations were performed using a Grace Alltima C18 reverse-phase column (10 μm particle size, 280 mm×22 mm). The mobile phase was a gradient elution from 75% MeCN/$H_2O$ to 95% MeCN/$H_2O$ over 30 min, followed by 100% MeCN for 10 min (flow rate of 12 mL/min). The sample was dissolved in 2:1 MeCN/MeOH (final concentration 50 mg/mL). ~50 mg (1 mL) of material were loaded on the column per run, each run producing ~40 mg of bryostatin 1, with the C13 enoate isomers separated. The fractions were concentrated, first by rotary evaporation then by lyophilization, to yield bryostatin 1 as a white, airy powder in >99.5% purity. Representative HPLC chromatograms are shown in FIG. 11A, FIG. 11B and FIG. 11C. With reference to these figures, FIG. 11A shows Synthetic bryostatin 1 along with the E enoate isomer. FIG. 11B shows the trace for HPLC purified synthetic bryostatin 1. FIG. 11C shows the trace for the NCI sample of bryostatin 1.

Crystallization and X-Ray Crystallography Procedure

Single crystals of $C_{47}H_{68}O_{17}\cdot MeOH_{1.55}$ (bryostatin 1 methanol solvate) were prepared by dissolving a sample in dichloromethane (~23 mg/ml), carefully layering an equal volume of methanol on top of the solution, and allowing the solvent to slowly evaporate over the course of multiple days. Crystals were very fragile and sensitive to mechanical stress. Rapid solvent loss was observed upon removal from mother liquor. A suitable needle-shaped crystal was selected without further cutting and mounted in ParatoneN on a D8Venture diffractometer. The X-ray beam was focused on the tip of the needle. The crystal was kept at 100.0 K during data collection. Upon removal of the crystal, severe radiation damage was visible. SADABS-2016/2 was used for absorption correction. The ratio of minimum to maximum transmission was 0.7333, wR2(int) was 0.1645 before and 0.0906 after correction, and the B-value was refined with linear dependence on frame number to allow for crystal decomposition. Using the Apex3 suite (Bruker-AXS (2016). APEX3. Version 2016.9-0. Madison, Wis.), the structure was solved with the ShelXT (G. Sheldrick, SHELXT—Integrated space-group and crystal-structure determination. *Acta Cryst.* A71, 3-8 (2015).) structure solution program using 'Intrinsic Phasing.' Using Olex2 (O. V. Dolomanov, L. J. Bourhis, R. J. Gildea, J. A. K. Howard, H. Puschmann, OLEX2: a complete structure solution, refinement and analysis program. *J. Appl. Cryst.* 42, 339-341 (2009)), the structure was refined with the XL (G. Sheldrick, A short history of SHELX. *Acta Cryst.* A64, 112-122 (2008)) refinement package using least squares minimization. Flack parameter x=0.11(4) was determined using 3386 quotients [(I+)−(I−)]/[(I+)+(I−)] (S. Parsons, H. D. Flack, T. Wagner, Use of intensity quotients and differences in absolute structure refinement. *Acta Cryst.* B69, 249-259 (2013)). Hooft parameter (R. W. W. Hooft, L. H. Straver, A. L. Spek, Determination of absolute structure using Bayesian statistics on Bijvoet differences. *J. Appl. Cryst.* 41, 96-103 (2008)) y=0.09(5) was determined using Platon (A. Spek, Structure validation in chemical crystallography. *Acta Cryst.* D65, 148-155 (2009)) Bijvoet-Pair analysis.

Figure 13:
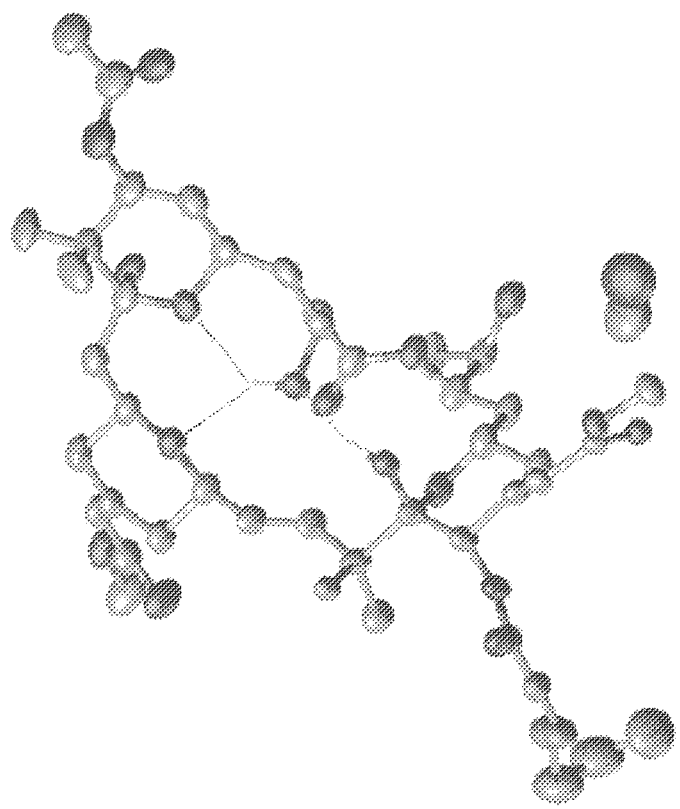
FIG. 13 shows a crystal structure of synthetic bryostatin 1, prepared by the subject methods, determined by x-ray diffraction (proton atoms omitted for clarity).

In all analytical respects, including NMR, IR, optical rotation and high-resolution mass spectrometry, synthetic bryostatin 1 prepared by the methods described herein was identical to an authentic sample of natural bryostatin 1 supplied by the NCI (National Cancer Institute). ¹HNMR traces comparing the synthetic bryostation 1 prepared by the subject methods and the natural bryostatin are illustrated in FIG. 12A (synthetic) and FIG. 12B (natural). An X-ray crystal structure of synthetic bryostatin 1 is depicted in FIG. 13 (noting that protons have been omitted for clarity).

Example 2: Exemplary Synthetic Procedure for C13 Analog

FIG. 6A to FIG. 6C illustrate exemplary synthetic schemes for preparation of C13 substituted analogs of bryostatin compounds. One such compound 6B1, wherein

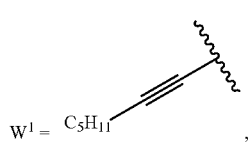

was prepared according to the procedure that follows.

Preparation of Compound 6B1: To a 15 mL polypropylene falcon tube equipped with magnetic stir bar was added compound 6B (15 mg, 0.0124 mmol, 1 equiv) and 3:1 THF/H₂O (1 mL). The falcon tube was transferred to a 4° C. cold room. HF-pyridine (0.32 mL) was added (final concentration ~0.01M). After 96 h, the reaction mixture was warmed to room temperature. After an additional 64 h (~6.5 days in total), the reaction mixture was quenched by slowly syringing the solution into a separatory funnel containing saturated aqueous NaHCO₃ (20 mL) and EtOAc (20 mL). The layers were separated, and the aqueous layer was extracted with EtOAc (4×20 mL). The combined organic layers were washed with 0.5M HCl (10 mL) to remove pyridine, and aqueous layer back-extracted with EtOAc (2×20 mL). The combined organic layers were dried over Na₂SO₄, filtered, and concentrated. Purification was accomplished by silica gel flash column chromatography (25-65% EtOAc/Hex) affording analog 6B1 (6.6 mg, 63% yield) as a white solid. Compound purity was established by TLC (one spot) analysis.

Example 3: PKC Binding Assay Protocol

The protein kinase C (PKC) affinity of bryostatin 1 and compounds 34 and 35 was performed via competition with ³H-phorbol-12,13-dibutyrate (³H-PDBu) as described below.

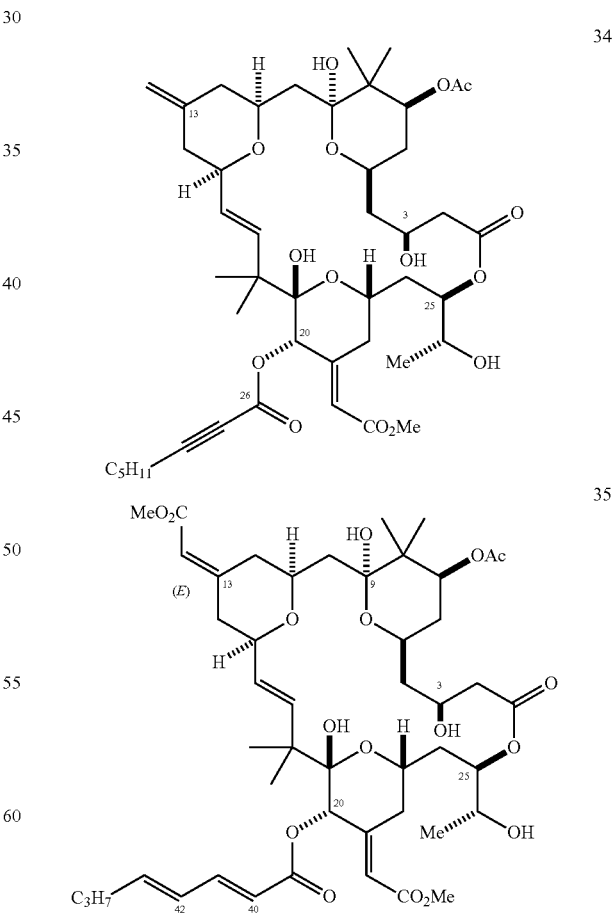

This procedure entails a glass-fiber filtration method to determine bound radioligand. PKC-beta-I and PKC-delta were selected for preliminary evaluation. The former is a member of the conventional PKC subfamily while the latter is a member of the novel PKC sub-family (A. C. Newton. Protein Kinase C: Structure, Function, and Regulation. *J. Biol. Chem.* 270, 28495-28498 (1995)).

Preparation of PKC Binding Assay Buffer

To a 50 mL polypropylene tube was added Tris-HCl (pH 7.4, 1 M, 1 mL), KCl (1 M, 2 mL), $CaCl_2$ (0.1 M, 30 μL), and bovine serum albumin (40 mg, Sigma-Aldrich). This mixture was diluted to 20 mL with deionized $H_2O$ and mixed gently. The buffer was stored on ice until use. The final concentration of these constituents is shown in the following table:

| Constituent | Stock concentration | Quantity | Final Concentration |
|---|---|---|---|
| pH 7.4 Tris-HCl | 1.0 M | 1.0 mL | 50 mM |
| KCl | 1.0 M | 2.0 mL | 100 mM |
| $CaCl_2$ | 0.10 M | 30 μL | 0.15 mM |
| Bovine Serum Albumin | — | 40 mg | 2 mg/mL |
| Deionized $H_2O$ | — | Final vol of 20 mL | — |

Preparation of Phosphatidylserine (PS) Vesicles Solution

For every two assays, 3.5 mg phosphatidylserine (Avanti Polar Lipids, porcine, 25 mg/mL $CHCl_3$ solution) was concentrated by removing chloroform under a stream of nitrogen followed by reduced pressure. The solid PS was suspended as vesicles in freshly prepared PKC binding assay buffer (3.5 mL) by sonicating six times for 30 sec, with a 30 sec rest between sonications (Branson Sonifier 250, power=2, 50% duty cycle). The resulting milky cloudy mixture (1 mg/mL) was stored on ice until use.

Preparation of PKC Isoform Solution

Assay PKC was prepared by dissolving a 4 μg aliquot of the indicated recombinant human PKC isoform (Invitrogen) into 11.6 mL of PKC binding assay buffer (this amount is sufficient for two assays). The diluted PKC was stored on ice for immediate use.

Preparation of 3H-PDBu Solution $^3$H-PDBu (American Radiolabeled Chemicals, Inc.; 1 mCi/mL acetone solution; specific activity: 20 μCi/mmol) was diluted 10-fold with DMSO. The resulting 500 nM stock solution was further diluted with DMSO to 30 nM.

Preparation of Analog Compound Dilutions

Compound dilutions were prepared by serially diluting from a chosen "high" concentration by factors of 3 or 4. For each analog compound, seven concentrations were used to define the inhibition curve (i.e. for exocyclic alkene 34, the analog concentrations used were 3000 nM, 750 nM, 188 nM, 46.9 nM, 11.7 nM, 2.93 nM, and 0.73 nM).

"MasterMix" Solution

To a polypropylene tube was added 3.3 mL of 1 mg/mL PS vesicles solution, 11 mL of PKC isoform solution, and 1.1 mL of 30 nM $^3$H-PDBu solution were added. The resulting solution was vortexed to mix and stored on ice.

PKC Binding Assay Protocol

Materials:
Glass-fiber filters (Whatman GF/B) were prepared by soaking them in a solution of aqueous polyethyleneimine (10% by vol, 18 mL) in deionized water (600 mL) for ≥1 h.
500 mL "rinsing buffer" of 20 mM Tris, pH 7.4 was cooled on ice for the duration of the incubation period and for the remainder of the assay.

Triplicate data points were obtained for each analog concentration. For each data point, 280 μL of "Master Mix" Solution and 20 μL of analog compound at a specified concentration were added to a polypropylene tube. Non-specific $^3$H-PDBu binding was assessed in triplicate by substitution of the analog compound with unlabeled PDBu (20 μL of a 75 μM stock, assay concentration: 5 μM). Maximal $^3$H-PDBu binding was assessed in triplicate by substitution of the analog compound with 20 μL DMSO. The solutions were vortexed to mix, incubated at 37° C. for 10 min, and incubated on ice for at least 30 min prior to filtration. Using a Brandel Harvester, the assay contents from each polypropylene tube were vacuum-filtered through polyethylenimine-soaked filters, washing with rinsing buffer (3×) and drying first under vacuum for 5 min and then under ambient conditions for ≥2 h. The resulting filters had circular perforations for each data point, which were removed with forceps and placed in a scintillation vial. Scintillation vials were filled with Bio-Safe II scintillation fluid (5 mL) and measured for radioactivity using a Beckman LS 6000SC scintillation counter. Counts per minute (cpm) were averaged for each triplicate dilution. The data were plotted—cpm vs. log(concentration)—using Prism® by GraphPad Software and an $IC_{50}$ was determined using that program's built-in one-site competition least squares regression function. $K_i$ values were calculated using the equation: $K_i=IC_{50}/(1+([^3H-PDBu]/Kd))$. The Kd of $^3$H-PDBu was measured via saturation binding under identical conditions and found to be 8.8 nM for PKC beta-I and 4.5 nM for PKC delta. Using this method, 34 was found to bind PKC beta-1 with a $K_i$ of 3.9 (2.7-5.9) nM and PKC delta with a $K_i$ of 0.76 (0.53-1.1) nM (note, error ranges presented in parentheses indicate 95% confidence intervals from nonlinear regression analysis). Similarly, 35 was found to bind PKC beta-1 with a $K_i$ of 12 (8.4-17) nM and PKC delta with a $K_i$ of 1.4 (1.0-2.0) nM. As a control, bryostatin 1 was found to bind PKC beta-1 with a $K_i$ of 1.6 (1.1-2.3) nM and PKC delta with a $K_i$ of 2.4 (1.5-3.6) nM.

Binding data for bryostatin 1 and analogs 34 and 35 is shown in the table below:

| | PKC $K_i$ (nM) | |
|---|---|---|
| compound | beta-I | delta |
| bryostatin 1 | 16.1 (1.1-2.3) | 2.4 (1.5-36) |
| alkene 34 | 3.9 (2.7-5.9) | 0.76 (0.53-1.1) |
| (E)-enoate 35 | 12 (8.4-1.7) | 1.4 (10-2.0) |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the following.

Notwithstanding the appended claims, the disclosure set forth herein is also described by the following clauses.

Clause 1. A method of preparing a bryostatin compound, wherein the method comprises:

(a) preparing a compound of formula (X) from a starting material of formula (I) or a synthon thereof or a synthetic equivalent thereof:

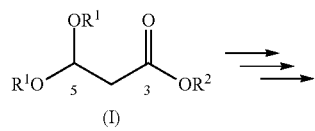

(I)

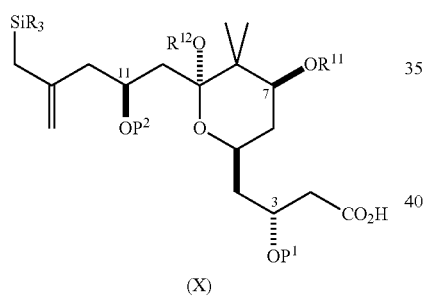

(X)

wherein:

$P^1$ and $P^2$ are independently a hydroxyl protecting group or synthetic equivalent thereof;

each R and $R^1$-$R^2$ is independently an alkyl or a substituted alkyl;

$R^{12}$ is an alkyl or a substituted alkyl; and $R^{11}$ is an acyl, a substituted acyl, an alkyl, a substituted alkyl, —CO-aryl, —CO(substituted aryl), —CO-heteroaryl, or —CO(substituted heteroaryl); and (b) preparing a compound of formula (XX) from a starting material of formula (XI) or a synthon thereof or a synthetic equivalent thereof:

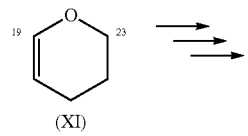

(XI)

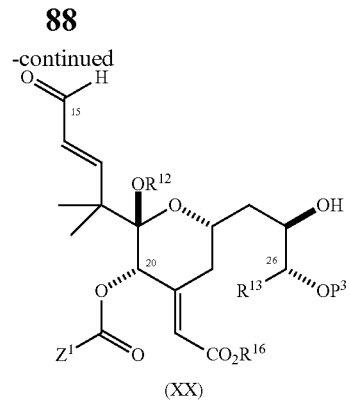

(XX)

wherein:

$Z^1$ is an alkynyl, a substituted alkynyl, an allenyl, a substituted allenyl an alkyl or a substituted alkyl (e.g., including one or more O or N atoms in the carbon chain, or substituted with a cycloalkyl, substituted cycloalkyl, cyclic alkenyl, substituted cyclic alkenyl, aryl, substituted aryl, heteroaryl, or substituted heteroaryl);

$R^{12}$, $R^{13}$ and $R^{16}$ are independently an alkyl or a substituted alkyl; and $P^3$ is H or a hydroxyl protecting group.

Clause 2. The method of clause 1, wherein step (a) comprises 10 synthetic steps or fewer.

Clause 3. The method of any one of clauses 1-2, wherein step (b) comprises 13 synthetic steps or fewer; and the starting material of formula (XI) or a synthon thereof or a synthetic equivalent thereof is selected from one of the following:

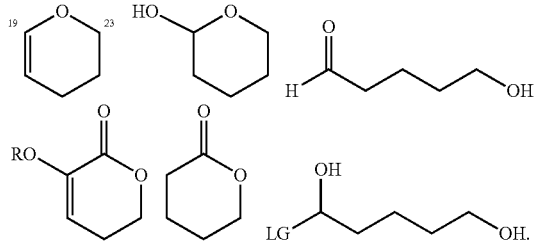

Clause 4. The method of any one of clauses 1-3, wherein $Z^1$ comprises 4-10 carbons.

Clause 5. The method of clause 4, wherein $Z^1$ is:

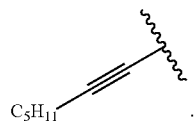

Clause 6. The method of any one of clauses 1-5, further comprising:

(c) coupling the compound of formula (X) and the compound of formula (XX) via esterification and macrocyclization (or vice versa) to produce a macrocyclic compound; and (d) preparing a compound of formula (XXII) from the macrocyclic compound (e.g., via an oxidative cleavage, such as an osmylation/diol cleavage, or an ozonolysis reaction):

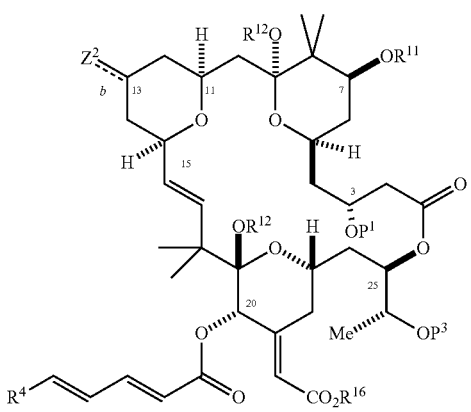

(XXII)

wherein:

R⁴ is an alkyl or a substituted alkyl;

Z² is =CR⁵R⁶ or =NR⁷ when the covalent bond designated "b" is a double bond;

Z² is —OR⁸ or —N(R⁷)₂ when the covalent bond designated "b" is a single bond; and R⁵, R⁶, R⁷ and R⁸ are each independently H, alkyloxycarbonyl, substituted alkyloxycarbonyl, alkyl or substituted alkyl;

P¹ and P³ are independently H or a hydroxyl protecting group;

R¹¹ is H, an acyl, a substituted acyl, an alkyl or a substituted alkyl;

R¹² is H, an alkyl or a substituted alkyl; and

R¹⁶ is H, an alkyl or a substituted alkyl.

Clause 7. The method of clause 6, further comprising deprotecting a protected hydroxy group to produce a bryostatin compound having a free hydroxyl group.

Clause 8. The method of clause 7, further comprising preparing a prodrug of the bryostatin compound.

Clause 9. The method of clause 6, wherein the macrocyclic compound is of formula (XXI):

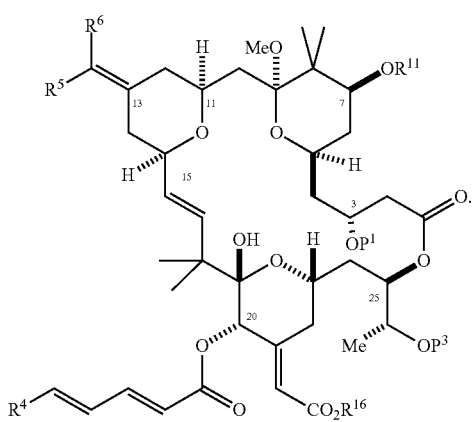

(XXI)

Clause 10. The method of any one of clauses 6-9, wherein the bryostatin compound has the structure of formula (XXIII);

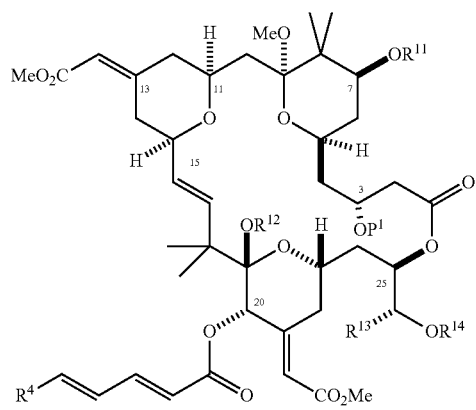

(XXIII)

wherein:

R¹³ is an alkyl or a substituted alkyl; and

R¹⁴ is H, a hydroxyl protecting group or a promoiety.

Clause 11. The method of any one of clauses 6-9, wherein the bryostatin compound has the structure of formula (XXXII):

(XXXII)

wherein:

R¹³ is an alkyl or a substituted alkyl; and

R¹⁴ is H, a hydroxyl protecting group or a promoiety.

Clause 12. The method of any one of clauses 1-10, wherein step (a) comprises a method of preparing the compound of formula (X) from a compound of formula (III):

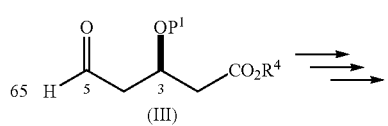

(III)

-continued

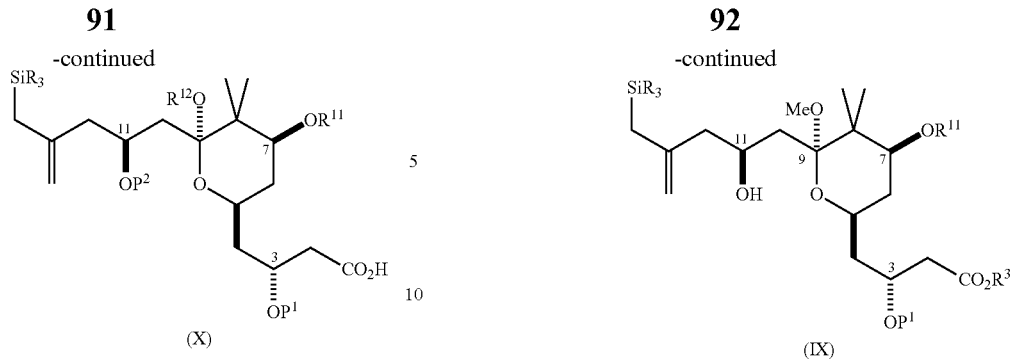

(X)

wherein:

$P^1$ and $P^2$ are independently H or a hydroxyl protecting group;

$R^4$ is H, an alkyl or a substituted alkyl; each R and $R^{12}$ is an alkyl or a substituted alkyl; and $R^{11}$ is an acyl, a substituted acyl, an alkyl or a substituted alkyl.

Clause 13. The method of any one of clauses 1-11, wherein step (a) comprises preparing a compound of formula (VII) from a compound of formula (VI):

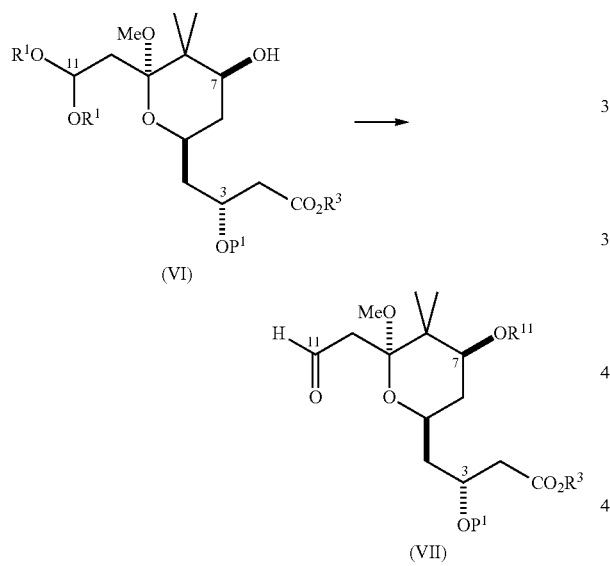

wherein $R^3$ is H, an alkyl or a substituted alkyl.

Clause 14. The method of any one of clauses 1-13, wherein step (a) comprises reacting a compound of formula (VII) with a compound of formula (VIII) to stereoselectively produce a compound of formula (IX):

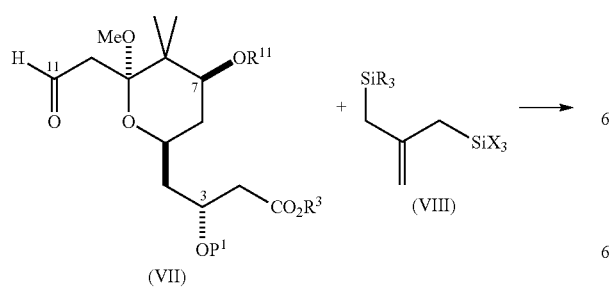

-continued (IX)

wherein:

each R and $R^3$ is alkyl or a substituted alkyl; and each X is a leaving group.

Clause 15. The method of clause 14, wherein the compound of formula (IX) is prepared under conditions sufficient to produce a 9:1 or greater ratio of (11S)- to (11R)-diastereoisomer of the compound of formula (IX).

Clause 16. The method of clause 15, wherein the compound of formula (IX) is prepared under conditions sufficient to obtain a 70% or greater yield from the compound of formula (VII).

Clause 17. The method of any one of clauses 1-16, wherein step (b) comprises preparing a compound of formula (XIVb) from compounds of formula (XII) and (XIII) via intermediate (XIVa):

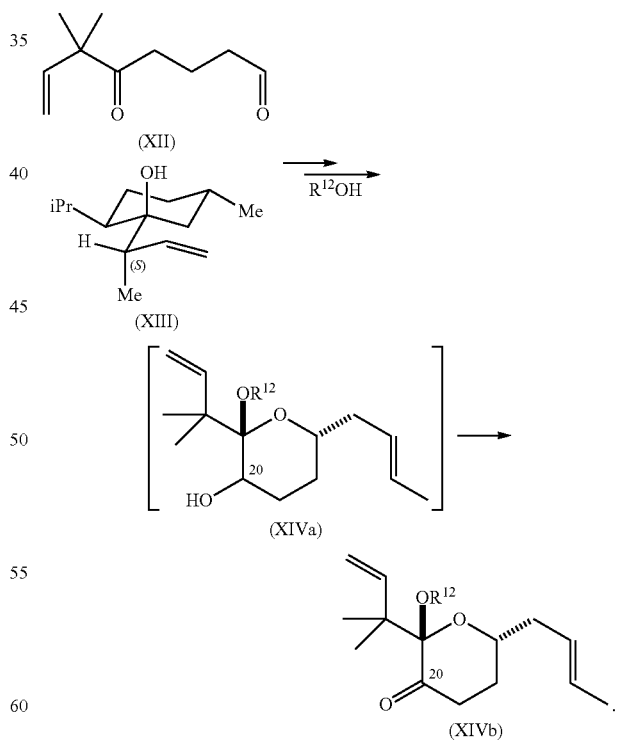

Clause 18. The method of any one of clauses 1-17, wherein step (b) comprises preparing a compound of formula (XIV) from a compound of formula (XIVb) via a metathesis reaction:

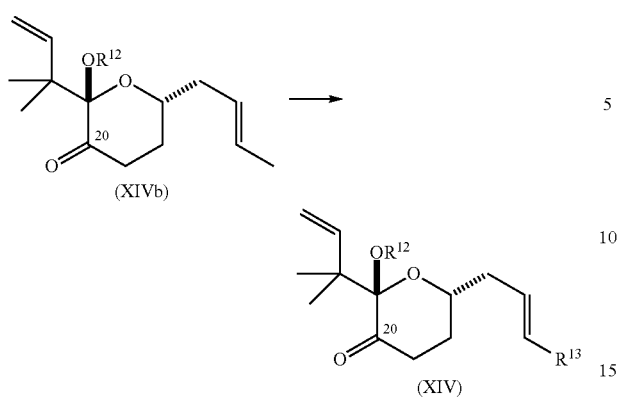

(XIVb) → (XIV)

wherein R[13] is an alkyl comprising at least two carbons or a substituted alkyl.

Clause 19. A method of preparing a bryostatin compound, according to any one of FIG. 1 to FIG. 9.

Clause 20. The method of any one of clauses 1-19, wherein the bryostatin compound is bryostatin 1.

Clause 21. A bryostatin analog having the formula (XXXI):

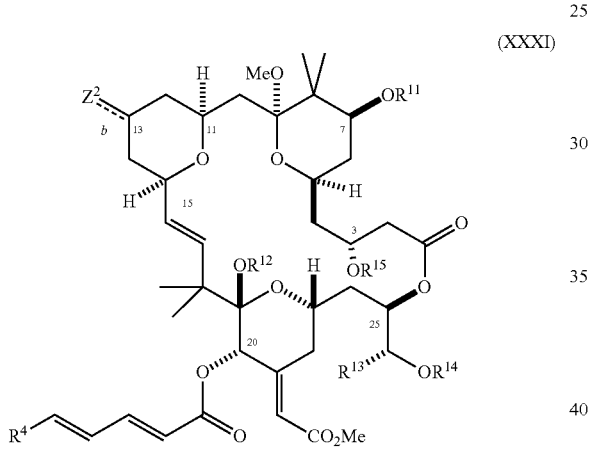

(XXXI)

wherein:
$R^4$ is an alkyl or a substituted alkyl;
$Z^2$ is $CR^5R^6$ or $NR^7$ when the covalent bond designated "b" is a double bond;
$Z^2$ is $OR^8$ or $N(R^7)_2$ when the covalent bond designated "b" is a single bond;
$R^5$, $R^6$, $R^7$ and $R^8$ are each independently H, alkyloxycarbonyl, substituted alkyloxycarbonyl, alkyl or substituted alkyl;
$R^{11}$ is an acyl, a substituted acyl, an alkyl or a substituted alkyl;
$R^{12}$ is H, an alkyl or a substituted alkyl;
$R^{13}$ is H, an alkyl or a substituted alkyl; and
$R^{14}$ and $R^{15}$ are independently H, a hydroxyl protecting group or a promoiety;
or a solvate, hydrate or prodrug form thereof and/or a salt thereof.

Clause 22. The bryostatin analog of clause 21, wherein $R^4$ is propyl.

Clause 23. The bryostatin analog of any one of clauses 19-22, wherein $R^{11}$ is an acyl or a substituted acyl.

Clause 24. The bryostatin analog of any one of clauses 19-23, wherein $R^{12}$ is an alkyl or a substituted alkyl.

Clause 25. The bryostatin analog of any one of clauses 20-24, wherein the covalent bond designated "b" is a double bond and $Z^2$ is $NR^7$ wherein $R^7$ is H, alkyloxycarbonyl, substituted alkyloxycarbonyl, alkyl or substituted alkyl.

Clause 26. The bryostatin analog of any one of clauses 20-25, wherein the covalent bond designated "b" is a single bond and $Z^2$ is $OR^8$ or $N(R^7)_2$, wherein $R^7$ and $R^8$ are each independently H, alkyloxycarbonyl (e.g., —$CO_2Me$), substituted alkyloxycarbonyl, alkyl or substituted alkyl.

Clause 27. The bryostatin analog of any one of clauses 20-26, wherein $R^{13}$ is an alkyl comprising at least 2 carbons or a substituted alkyl.

Clause 28. The bryostatin analog of any one of clauses 20-27, wherein $R^4$ is a substituted alkyl.

Clause 29. The bryostatin analog of any one of clauses 20-28, wherein $R^{14}$ is a promoiety.

Clause 30. A bryostatin analog having the formula (XXXIV):

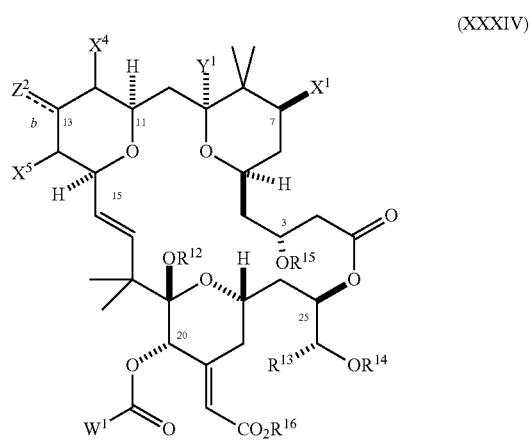

(XXXIV)

wherein:
$W^1$ is an alkenyl, a substituted alkenyl, an alkynyl, a substituted alkynyl, an allenyl, a substituted allenyl, an alkyl, a substituted alkyl, an aryl, a substituted aryl, a heteroaryl, a substituted heteroaryl, heteroalkyl, substituted heteroalkyl, heterocycle, substituted heterocycle, or a carbon chain containing oxygen or nitrogen atoms, and/or rings and substituted rings included cycloalkyl, cycloalkenyl and the like (e.g., a PEG or modified PEG group);
$Z^2$ is $CR^5R^6$ or $NR^7$ when the covalent bond designated "b" is a double bond;
$Z^2$ is $OR^8$, a phosphate, a phosphoryl, a thio group, a sulfate, a sulfonyl, an organoselenium group, or $N(R^7)_2$ when the covalent bond designated "b" is a single bond;
$R^5$, $R^6$, $R^7$ and $R^8$ are each independently H, halogen, alkyloxycarbonyl, substituted alkyloxycarbonyl, alkyl or substituted alkyl;
$X^1$ is H or $OR^{11}$;
$X^4$ and $X^5$ are independently selected from H, halogen, alkyl, substituted alkyl, alkoxy, amine, substituted amine, amide, substituted amide, acyl, hydroxyl, heteroalkyl, heteroaryl, substituted heteroalkyl, substituted heteroaryl, phosphate, organoselenium, thio, substituted thio;
$Y^1$ is H or $OR^{12}$;
$R^{12}$ is H, an alkyl or a substituted alkyl;
$R^{13}$ is H, an alkyl or a substituted alkyl; and
$R^{16}$ is H, an alkyl or a substituted alkyl,
$R^{14}$ and $R^{15}$ are independently H, a hydroxyl protecting group or a promoiety;
or a solvate, hydrate or prodrug form thereof and/or a salt thereof.

Clause 31. The bryostatin compound of clause 30, wherein the structure of XXXIV is:

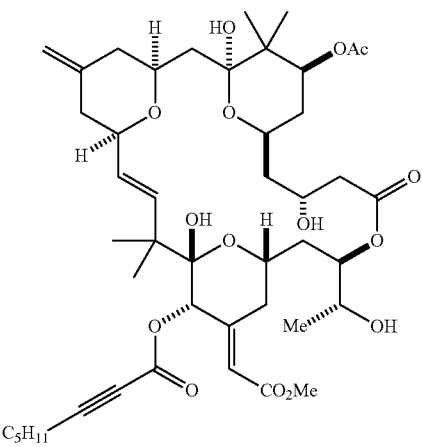

Clause 32. A bryostatin analog having the formula (XXXIII):

(XXXIII)

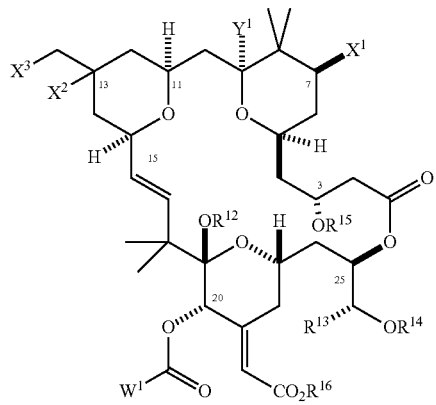

wherein:
$W^1$ is an alkenyl, a substituted alkenyl, an alkynyl, a substituted alkynyl, an allenyl, a substituted allenyl, an alkyl, a substituted alkyl, an aryl, a substituted aryl, a heteroaryl, a substituted heteroaryl, heteroalkyl, substituted heteroalkyl, heterocycle, substituted heterocycle, or a carbon chain containing oxygen or nitrogen atoms, and/or rings and substituted rings included cycloalkyl, cycloalkenyl and the like (e.g., a PEG or modified PEG group);

$X^1$ is H or $OR^{11}$;

$X^2$ and $X^3$ are independently selected from H, halogen, alkyl, substituted alkyl, alkoxy, amine, substituted amine, amide, substituted amide, acyl, hydroxyl, heteroalkyl, heteroaryl, substituted heteroalkyl, substituted heteroaryl, phosphate, organoselenium, thio, substituted thio, or $X^2$ and $X^3$ combine to form a carbocyclic ring or a heterocyclic ring e.g. a cyclopropane, an epoxide, an aziridine, a thiirane, a 4-membered spirocycle, a 5-membered spirocycle or a 6 membered spirocycle;

$Y^1$ is H or $OR^{12}$;

$R^{12}$ is H, an alkyl or a substituted alkyl;

$R^{13}$ is H, an alkyl or a substituted alkyl;

$R^{16}$ is H, an alkyl or a substituted alkyl; and $R^{14}$ and $R^{15}$ are independently H, a hydroxyl protecting group or a promoiety; or a solvate, hydrate or prodrug form thereof and/or a salt thereof.

Clause 33. A bryostatin analog of clause 30, having the formula (XXXV):

(XXXV)

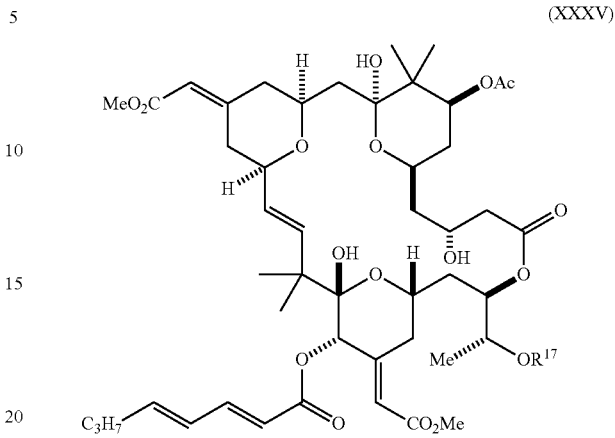

wherein $R^{17}$ is selected from an ester, a carbonate, a carbamate and an ether, and the $R^{17}$ group is optionally substituted with a group selected from alkyl, alkenyl, alkynyl, amines, hydroxyl groups, guanidinium groups, carbocycles, and heterocycles.

Clause 34. The bryostatin analog of clause 33, wherein the acetate group at C7 is replaced with a group selected from a H atom, an ester, a carbonate, a carbamate and an ether, all of which can be optionally substituted with one or more groups selected from, an alkyl, an alkenyl, an alkynyl, an amine, a hydroxyl, a disulfide, a guanidinium, a carbocycle, and a heterocycle.

Clause 35. A pharmaceutical composition comprising a therapeutically effective amount of a bryostatin analog of any one of clauses 20-34 and a pharmaceutically acceptable vehicle.

Clause 36. A pharmaceutical composition comprising a therapeutically effective amount of a bryostatin analog of any one of clauses 20-34, a pharmaceutically acceptable vehicle, and one or more agents selected from the group consisting of chemotherapeutic agents, antibiotics, alkylating agents, antimetabolites, hormones, antagonists, protein kinase C modulators of other classes, microtubule stabilizers, radioisotopes, antibodies, other natural products, HDAC inhibitors, bromodomain inhibitors and combinations thereof.

Clause 37. The pharmaceutical composition of clause 36, wherein one or more agents is selected from ara-C, taxol, cisplatin and vincristine.

Clause 38. The pharmaceutical composition of clause 35, wherein one or more agents is selected from disulfiram, JQ1, panobinostat, romidepsin, vorinostat, bryostatin, prostratin and acetritin.

Clause 39. A method of treating cancer, the method comprising administering a therapeutically effective amount of the pharmaceutical composition of any one of clauses 35-38 to an individual in need thereof.

Clause 40. The method of clause 39, wherein the cancer is selected from the group consisting of melanoma, myeloma, chronic lymphocytic leukemia (CLL), AIDS-related lymphoma, non-Hodgkin's lymphoma, colorectal cancer, renal cancer, prostate cancer, cancers of the head, neck, stomach, esophagus, anus, or cervix, ovarian cancer, breast cancer, peritoneal cancer, and non-small cell lung cancer.

Clause 41. A method of strengthening the immune system, the method comprising administering a therapeutically effective amount of the pharmaceutical composition of clause 35-38 to an individual in need thereof.

Clause 42. A method of treating a disorder of associative memory storage, the method comprising administering a therapeutically effective amount of the pharmaceutical composition of clause 35-38 to an individual in need thereof.

Clause 43. The method of clause 42, wherein the disorder of associative memory storage is selected from the group consisting of Alzheimer's disease and depression.

Clause 44. A method of treating a viral infection, the method comprising administering a therapeutically effective amount of the pharmaceutical composition of clause 35-38 to an individual in need thereof.

Clause 45. The method of clause 44, wherein the viral infection is selected from the group consisting of Epstein Barr Virus, HIV and HSV.

What is claimed is:

1. A bryostatin analog having the formula (XXXI):

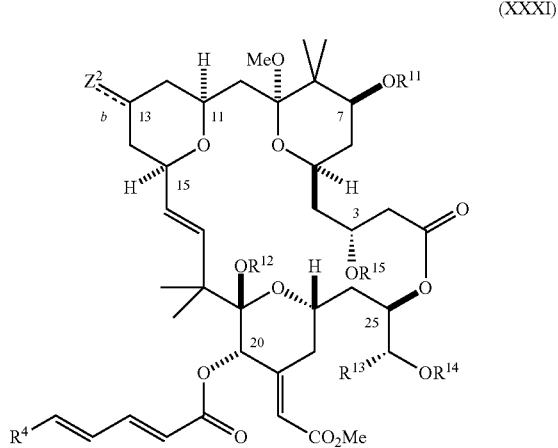

(XXXI)

wherein:

$R^4$ is an alkyl or a substituted alkyl;

$Z^2$ is $CR^5R^6$ or $NR^7$ when the covalent bond designated "b" is a double bond;

$Z^2$ is $OR^8$ or $N(R^7)_2$ when the covalent bond designated "b" is a single bond;

$R^5$ is alkyloxycarbonyl, substituted alkyloxycarbonyl, alkyl or substituted alkyl;

$R^6$, $R^7$ and $R^8$ are each independently H, alkyloxycarbonyl, substituted alkyloxycarbonyl, alkyl or substituted alkyl;

$R^{11}$ is a substituted acyl, an alkyl or a substituted alkyl;

$R^{12}$ is H, an alkyl or a substituted alkyl;

$R^{13}$ is H, an alkyl or a substituted alkyl; and $R^{14}$ and $R^{15}$ are independently H, a hydroxyl protecting group or a promoiety;

or a solvate, hydrate or prodrug form thereof and/or a salt thereof.

2. The bryostatin analog of claim 1, wherein $R^{14}$ is a promoiety.

3. A pharmaceutical composition comprising a therapeutically effective amount of a bryostatin analog of claim 1 and a pharmaceutically acceptable vehicle.

* * * * *